(12) United States Patent
    Takulapalli

(10) Patent No.: US 11,977,069 B2
(45) Date of Patent: May 7, 2024

(54) NANOPORE SENSOR, STRUCTURE AND DEVICE INCLUDING THE SENSOR, AND METHODS OF FORMING AND USING SAME

(71) Applicant: Bharath Takulapalli, Chandler, AZ (US)

(72) Inventor: Bharath Takulapalli, Chandler, AZ (US)

( * ) Notice: Subject to any disclaimer, the term of this patent is extended or adjusted under 35 U.S.C. 154(b) by 61 days.

(21) Appl. No.: 16/095,245

(22) PCT Filed: Apr. 19, 2017

(86) PCT No.: PCT/US2017/028468
    § 371 (c)(1),
    (2) Date: Oct. 19, 2018

(87) PCT Pub. No.: WO2017/184790
    PCT Pub. Date: Oct. 26, 2017

(65) Prior Publication Data
    US 2019/0145950 A1    May 16, 2019

Related U.S. Application Data

(60) Provisional application No. 62/324,352, filed on Apr. 19, 2016.

(51) Int. Cl.
    *G01N 33/487*    (2006.01)
    *B01L 3/00*    (2006.01)
    *G01N 27/447*    (2006.01)

(52) U.S. Cl.
    CPC ...... *G01N 33/48721* (2013.01); *B01L 3/5027* (2013.01); *G01N 27/44791* (2013.01); *B01L 3/502707* (2013.01)

(58) Field of Classification Search
    CPC ....... G01N 33/48721; G01N 27/44791; G01N 27/4146; B01L 3/5027; B01L 3/502707
    See application file for complete search history.

(56) References Cited

U.S. PATENT DOCUMENTS 5,234,566 A    8/1993    Osman et al.
5,264,395 A    11/1993    Bindal et al.
(Continued)

FOREIGN PATENT DOCUMENTS

CN    1774799 A    5/2006
CN    101668866    3/2010
(Continued)

OTHER PUBLICATIONS

Abe et la., "Electrochemically Controlled Layer-by-Layer Deposition of Metal-Cluster Molecular Multilayers on Gold," Angewandte Chemie International Edition, vol. 42(25), pp. 2912-2915, (2003).
(Continued)

*Primary Examiner* — Joshua L Allen
(74) *Attorney, Agent, or Firm* — Snell & Wilmer L.L.P.

(57) ABSTRACT

The present disclosure provides an improved device that can be used to sense and characterize a variety of materials. The device may be used for a variety of applications, including genome sequencing, protein sequencing, biomolecular sequencing, and detection of ions, molecules, chemicals, biomolecules, metal atoms, polymers, nanoparticles and the like.

20 Claims, 43 Drawing Sheets

(56) References Cited

U.S. PATENT DOCUMENTS

| | | | |
|---|---|---|---|
| 5,334,281 A | 8/1994 | Doerre et al. | |
| 5,431,883 A | 7/1995 | Barraud | |
| 5,683,569 A | 11/1997 | Chung et al. | |
| 6,111,280 A | 8/2000 | Gardner et al. | |
| 6,355,532 B1 | 3/2002 | Seliskar et al. | |
| 6,433,356 B1 | 8/2002 | Cahen et al. | |
| 6,437,404 B1 | 8/2002 | Xiang et al. | |
| 6,458,547 B1 | 10/2002 | Bryan et al. | |
| 6,753,200 B2 | 6/2004 | Craighead et al. | |
| 7,091,069 B2 | 8/2006 | Doris et al. | |
| 7,235,440 B2 | 6/2007 | O'Meara et al. | |
| 7,247,887 B2 | 7/2007 | King et al. | |
| 7,622,934 B2 | 11/2009 | Hibbs et al. | |
| 7,947,485 B2 | 5/2011 | Wu et al. | |
| 7,994,593 B2 | 8/2011 | Takulapalli et al. | |
| 8,154,093 B2 | 4/2012 | Bradley et al. | |
| 8,383,369 B2 | 2/2013 | Maxham et al. | |
| 8,426,900 B2 | 4/2013 | Ahn et al. | |
| 9,170,228 B2 | 10/2015 | Takulapalli | |
| 9,341,592 B2 | 5/2016 | Takulapalli | |
| 2002/0117659 A1 | 8/2002 | Lieber et al. | |
| 2003/0231531 A1* | 12/2003 | Baxter | B82Y 10/00 365/200 |
| 2004/0043527 A1 | 3/2004 | Bradley et al. | |
| 2004/0079636 A1 | 4/2004 | Hsia et al. | |
| 2004/0132070 A1 | 7/2004 | Star et al. | |
| 2004/0144985 A1 | 7/2004 | Zhang et al. | |
| 2004/0173812 A1* | 9/2004 | Currie | H01L 21/76224 257/103 |
| 2004/0195563 A1 | 10/2004 | Bao et al. | |
| 2004/0238379 A1 | 12/2004 | Lindsay et al. | |
| 2005/0026453 A1 | 2/2005 | O'Meara et al. | |
| 2005/0056892 A1 | 3/2005 | Seliskar | |
| 2005/0263790 A1 | 12/2005 | Moon et al. | |
| 2006/0113603 A1 | 6/2006 | Currie | |
| 2006/0154399 A1* | 7/2006 | Sauer | C12Q 1/6869 438/48 |
| 2006/0243969 A1 | 11/2006 | Bao et al. | |
| 2006/0263255 A1 | 11/2006 | Han et al. | |
| 2006/0267051 A1 | 11/2006 | Gstrein et al. | |
| 2007/0063304 A1 | 3/2007 | Matsumoto et al. | |
| 2007/0108052 A1 | 5/2007 | Luongo et al. | |
| 2007/0132043 A1* | 6/2007 | Bradley | G01N 27/4146 257/414 |
| 2008/0063566 A1 | 3/2008 | Matsumoto et al. | |
| 2008/0081769 A1 | 4/2008 | Hassibi | |
| 2008/0094051 A1 | 4/2008 | Williams et al. | |
| 2008/0220530 A1 | 9/2008 | Bahn et al. | |
| 2008/0283875 A1 | 11/2008 | Mukasa et al. | |
| 2009/0014757 A1 | 1/2009 | Takulapalli et al. | |
| 2009/0273356 A1 | 11/2009 | Pampin et al. | |
| 2010/0066348 A1* | 3/2010 | Merz | C12Q 1/6869 324/71.1 |
| 2010/0133107 A1 | 6/2010 | Fishelson et al. | |
| 2010/0237992 A1 | 9/2010 | Liautaud | |
| 2010/0297608 A1 | 11/2010 | Stern et al. | |
| 2010/0327255 A1* | 12/2010 | Peng | G01N 27/4148 257/9 |
| 2011/0024771 A1 | 2/2011 | Hajj-Hassan et al. | |
| 2011/0088466 A1 | 4/2011 | Frerichs | |
| 2011/0278258 A1 | 11/2011 | Kavusi et al. | |
| 2011/0279125 A1 | 11/2011 | Bedell et al. | |
| 2012/0021204 A1 | 1/2012 | Pei et al. | |
| 2012/0045844 A1 | 2/2012 | Rothberg et al. | |
| 2012/0055236 A1 | 3/2012 | Takulapalli | |
| 2012/0094852 A1 | 4/2012 | Berman et al. | |
| 2012/0190989 A1 | 7/2012 | Kaiser et al. | |
| 2012/0193237 A1* | 8/2012 | Afzali-Ardakani | B82Y 15/00 204/627 |
| 2012/0131403 A1 | 10/2012 | Cash et al. | |
| 2012/0286330 A1 | 11/2012 | Kellam | |
| 2014/0327446 A1* | 11/2014 | Bedell | G01N 27/02 324/444 |
| 2015/0014752 A1* | 1/2015 | D'Emic | G01N 27/4146 257/253 |
| 2015/0060952 A1 | 3/2015 | Takulapalli et al. | |
| 2015/0376692 A1 | 12/2015 | Esfandyarpour et al. | |
| 2016/0041155 A1 | 2/2016 | Takulapalli | |
| 2016/0041159 A1 | 2/2016 | Labaer et al. | |
| 2016/0258941 A1 | 9/2016 | Takulapalli | |
| 2016/0313278 A1* | 10/2016 | Knickerbocker | G01N 33/48721 |

FOREIGN PATENT DOCUMENTS

| | | |
|---|---|---|
| CN | 101896814 | 11/2010 |
| CN | 102242062 | 11/2011 |
| CN | 104769424 A | 7/2015 |
| EP | 2836828 | 2/2015 |
| EP | 2973456 | 1/2016 |
| GB | 2389424 | 11/2004 |
| GB | 2416210 | 1/2006 |
| JP | 07333182 | 12/1995 |
| JP | 2004-309483 | 11/2004 |
| JP | 2005-061960 | 3/2005 |
| JP | 2014190891 A | 10/2014 |
| WO | 2004081982 A2 | 9/2004 |
| WO | 2005015193 | 2/2005 |
| WO | 2006134942 | 12/2006 |
| WO | 2009017882 | 2/2009 |
| WO | 2010026488 | 3/2010 |
| WO | 2011017077 | 2/2011 |
| WO | 2012075445 | 6/2012 |
| WO | 2012131403 | 10/2012 |
| WO | 2013063126 | 5/2013 |
| WO | 2013155116 | 10/2013 |
| WO | WO-2013155116 A1 * | 10/2013 ......... H01L 29/0692 |
| WO | 2014143954 | 9/2014 |
| WO | 2014146020 | 9/2014 |
| WO | 2017184790 | 10/2017 |

OTHER PUBLICATIONS

Baird et al., "Blood-Based Proteomic Biomarkers of Alzheimer's Disease Pathology," Frontiers in Neurology, vol. 6, Article 236, 16 Pages, (2015).

Barizuddin et al., "Plasmonic Sensors for Disease Detection—A Review," Journal of Nanomedicine & Nanotechnology, vol. 7(3), 1000373(10 Pages), (2016).

Bischoff et al., "Amino Acids: Chemistry, Functionality and Selected Non-Enzymatic Post-Translational Modifications" Journal of Proteomics, vol. 75(8), pp. 2275-2296, (2012).

Breiling et al., "Epigenetic Regulatory Functions of DNA Modifications: 5-Methylcytosine and Beyond," Epigenetics & Chromatin, vol. 8(24), 9 Pages, (2015).

Clark et al., "Advances in Blood-Based Protein Biomarkers for Alzheimer's Disease," Alzheimer's Research & Therapy, vol. 5(18), 8 Pages, (2013).

Feinberg et al., "Epigenetic Modulators, Modifiers and Mediators in Cancer Aetiology and Progression," Nature Reviews Genetics, vol. 17, pp. 284-299, (2016).

Kulkarni et al., "Detection Beyond the Debye Screening Length in a High-Frequency Nanoelectronic Biosensor," Nano Letters, vol. 12(2), pp. 719-723, (2012).

Liu et al., "Super-Selective Cryogenic Etching for Sub-10 NM Features," Nanotechnology, vol. 24(1), (2013).

Miles et al., "Single Molecule Sensing with Solid-State Nanopores: Novel Materials, Methods, and Applications," Chemical Reviews, vol. 42(1), pp. 15-28, (2013).

Phan et al., "Molecular Self-Assembly at Metal-Electrolyte Interfaces," International Journal of Molecular Sciences, vol. 14(3), pp. 4498-4524, (2013).

Reiner et al., "Disease Detection and Management via Single Nanopore-Based Sensors," Chemical Reviews, vol. 112(12), pp. 6431-6451, (2012).

Rothbart et al., "Interpreting the Language of Histone and DMA Modification," Biochim Biophys Acta, vol. 1839(8), pp. 627-643, (2014).

(56) References Cited

OTHER PUBLICATIONS

Storm et al., "Electron-Beam-Induced Deformations of SiO2 Nanostructures," Journal of Applied Physics, vol. 98, 014307 (8 Pages), (2005).
Takulapalli et al., "Electrical Detection of Amine Ligation to a Metalloporphyrin via a Hybrid SOI-MOSFET," Journal of the American Chemical Society, vol. 130, pp. 2226-2233, (2008).
Takulapalli, "Molecular Sensing Using Monolayer Floating Gate, Fully Depleted SOI MOSFET Acting as an Exponential Transducer," ACS Nano, vol. 4, pp. 999-1011, (2010).
Venkatesan et al., "Nanopore Sensors for Nucleic Acid Analysis," Nature Nanotechnology, vol. 6, pp. 615-624, (2011).
Zheng et al., "Frequency Domain Detection of Biomolecules Using Silicon Nanowire Biosensors," Nano Letters, vol. 10(8), pp. 3179-3183, (2010).
ThermoFisher, "Overview of Post-Translational Modifications (PTMs)," https://www.thermofisher.com/us/en/home/life-science/protein-biology/protein-biology-learning-center/protein-biology-resource-library/pierce-protein-methods/overview-post-translational-modification.html, 7 Pages.
Robertson, "What is DNA Methylation?" News Medical Life Sciences, http://www.news-medical.net/life-sciences/What-is-DNA-Methylation.aspx.
"Histone Modifications: A Guide," abcam, http://www.abcam.com/epigenetics/histone-modification-a-guide, 8 Pages.
PCT; International Preliminary Report on Patentability dated Oct. 23, 2018 in International Application No. PCT/US2017/028468.
PCT; International Search Report dated Sep. 5, 2017 in International Application No. PCT/US2017/028468.
PCT; Written Opinion of the International Searching Authority dated Sep. 5, 2017 in International Application No. PCT/US2017/028468.
USPTO; Non-Final Office Action dated Sep. 13, 2010 in U.S. Appl. No. 12/135,940.
USPTO; Notice of Allowance dated Mar. 31, 2011 in U.S. Appl. No. 12/135,940.
USPTO; Non-Final Office Action dated Oct. 3, 2013 in U.S. Appl. No. 12/663,666.
USPTO; Non-Final Office Action dated Apr. 8, 2014 in U.S. Appl. No. 12/663,666.
USPTO; Notice of Allowance dated Jan. 22, 2015 in U.S. Appl. No. 12/663,666.
USPTO; Non-Final Office Action dated May 27, 2015 in U.S. Appl. No. 14/391,661.
USPTO; Notice of Allowance dated Jun. 3, 2015 in U.S. Appl. No. 12/663,666.
USPTO; Notice of Allowance dated Feb. 18, 2016 in U.S. Appl. No. 14/391,661.
USPTO; Non-Final Office Action dated Mar. 28, 2017 in U.S. Appl. No. 15/156,213.
USPTO; Final Office Action dated Jan. 26, 2018 in U.S. Appl. No. 15/156,213.
USPTO; Requirement for Restriction dated May 24, 2018 in U.S. Appl. No. 14/777,425.
USPTO; Non-Final Office Action dated Sep. 7, 2018 in U.S. Appl. No. 14/777,425.
USPTO; Non-Final Office Action dated Dec. 27, 2018 in U.S. Appl. No. 15/156,213.
PCT; International Search Report dated May 3, 2009 in International Application No. PCT/US2008/066190.
PCT; Written Opinion of the International Searching Authority dated May 3, 2009 in International Application No. PCT/US2008/066190.
PCT; International Preliminary Report on Patentability dated Dec. 11, 2009 in International Application No. PCT/US2008/066190.
PCT; International Search Report dated Jul. 2, 2013 in International Application No. PCT/US2013/035852.
PCT; Written Opinion of the International Searching Authority dated Jul. 2, 2013 in International Application No. PCT/US2013/035852.
PCT; International Preliminary Report on Patentability dated Oct. 14, 2014 in International Application No. PCT/US2013/035852.
PCT; International Search Report dated Nov. 12, 2014 in International Application No. PCT/US2014/030891.
PCT; Written Opinion of the International Searching Authority dated Nov. 12, 2014 in International Application No. PCT/US2014/030891.
PCT; International Preliminary Report on Patentability dated Sep. 15, 2015 in International Application No. PCT/US2014/030891.
PCT; International Search Report dated Feb. 15, 2019 in International Application PCT/US2018/063170.
PCT; Written Opinion of the International Searching Authority dated Feb. 15, 2019 in International Application No. PCT/US2018/063170.
JPO; Examination Report dated Jun. 6, 2013 in Japanese Application No. 2010-511384.
JPO; Examination Report dated Jan. 15, 2014 in Japanese Application No. 2010-511384.
JPO; Final Examination Report dated Oct. 3, 2014 in Japanese Application No. 2010-511384.
CIPO; Examination Report dated Apr. 14, 2016 in Chinese Application No. 201380030209.6.
CIPO; Examination Report dated Feb. 27, 2017 in Chinese Application No. 201380030209.6.
CIPO; Notice of Allowance dated Aug. 2, 2017 in Chinese Application No. 201380030209.6.
CIPO; Examination Report dated Jul. 4, 2018 in Chinese Application No. 201480027713.5.
EPO; Extended European Search Report dated Oct. 19, 2016 in European Application No. 14762408.4.
EPO; Supplementary Search Report dated Nov. 7, 2016 in European Application No. 14762408.4.
EPO; Examination Report dated Dec. 7, 2018 in European Application No. 14762408.4.
EPO; Examination Report dated Jan. 27, 2017 in European Application No. 08826782.8.
EPO; 2nd Examination Report dated Oct. 23, 2017 in European Application No. 08826782.8.
INPO; Examination Report dated Jun. 29, 2018 in Indian Application No. 9382/DELNP/2014.
Yang et al., "Molecular Control of the Drain Current in a Buried Channel MOSFET," Arizona State University, Department of Electrical Engineering et al., 4 Pages, (Sep. 2002).
Langmuir-Blodgett, "Porphyrin Molecules for Sensing Applications," Deposition, (Abstract Only).
Bouvet, "Phthalocyanine-Based Filed-Effect Transistors as Gas Sensors," Analytical and Bioanalytical Chemistry, vol. 384, pp. 366-373, (2006).
Yang et al., "Molecular Control of the Threshold Voltage of an NMOS Inversion Layer," Microelectronic Engineering, vol. 63, pp. 135-139, (2002).
Laws, "Drain Current Control in a Hybrid Molecular/MOSFET Device," Physica E: Low-Dimensional Systems and Nanostructures, vol. 17, pp. 659-663, (2003).
Yang et al., "Controlling the Threshold Voltage of a Metal-Oxide-Semiconductor Field Effect Transistor by Molecular Protonation of the Si: $SiSiO_2$ Interface," Journal of Vacuum Science & Technology B, vol. 20(4), (Jul./Aug. 2002).
Takulapalli, "Molecular Sensing Using Monolayer Gate Fully Depleted Silicon on Insulator Nano MOSFETS," ProQuest Dissertations and Theses; Thesis (Ph.D.) Arizona State University, (Aug. 2006).
Shepherd et al., "Weak Inversion ISFETs for Ultra-Low Power Biochemical Sensing and Real-Time Analysis," Sensors and Actuators B. Elsevier Sequoia S.A., Lausanne, vol. 107(1), pp. 468-473, (May 2005).
Martinoia et al., "A Behavioral Macromodel of the ISFET in SPICE," Sensors and Actuators B, Elsevier Sequoia S. A., Lausanne, vol. 62(3), pp. 182-189, (Mar. 2000).
Takulapalli, "Detection of Pyridine using Zn TCPP SAM Coated SOI Mosfet Devices," (Jun. 9, 2006).
Ashcroft et al., "Calibration of a PH Sensitive Buried Channel Silicon-On-Insulator MOSFET for Sensor Applications," Physica Status Solidi, vol. 241(10), pp. 2291-2296, (2004).

(56) References Cited

OTHER PUBLICATIONS

Takulapalli et al., "The pH Response of a Silicon-On-Insulator MOSFET with an Integrated Nanofluidic Cell," In SOI Conference, 2003, IEEE International, pp. 114-116, (2003).
Hall et al., "GMR Biosensor Arrays: A System Perspective, Biosensors and Bioelectronics," vol. 25(9), pp. 2051-2057, (May 2010).
Ouisse et al., "Influence of Series Resistances and Interface Coupling on the Transconductance of Fully-Depleted-Silicon-On-Insulator MOSFETs," Solid-State Electronic, vol. 35(2), pp. 141-149, (1992).
Suk et al., "ZnO Nanorod Biosensor for Highly Sensitive Detection of Specific Protein Binding," Journal of the Korean Physical Society, vol. 49(4), pp. 1635-1639, (Oct. 2006).
Ishikawa et al., "Fabrication of [110]-Aligned Si Quantum Wires Embedded in SiO2 by Low-Energy Oxygen Implantation," Nuclear Instruments and Methods in Physics Research, vol. 147, pp. 304-309, (1999).
Sano et al., "Immuno-PCR: Very Sensitive Antigen Detection by Means of Specific Antibody-DNA Conjugates," Science, vol. 258(5079), pp. 120-122, (1992).
Nam et al., "Nanoparticle-Based Bio-Bar Codes for the Ultrasensitive Detection of Proteins," Science, vol. 301(5641), pp. 1884-1886, (Sep. 2003).
Niemeyer et al., "Self-Assembly of DNA-Streptavidin Nanostructures and Their Use as Reagents in Immuno-PCR," Nucleic Acids Research, vol. 27(23), pp. 4553-4561, (1999).
Zhou et al., "Universal Immuno-PCR for Ultra-Sensitive Target Protein Detection," Nucleic Acids Research, vol. 21(25), pp. 6038-6039, (Dec. 1993).
Niemeyer et al., "Immuno-PCR: High Sensitivity Detection of Proteins by Nucleic Acid Amplification," Trends in Biotechnology, vol. 23(4), pp. 208-216, (Apr. 2005).
Crowther, "Enzyme Linked Immunosorbent Assay (ELISA)," Molecular Biomethods Handbook, Chapter 37, pp. 657-682, (2008).
Chang et al., "Immuno-PCR: An Ultrasensitive Immunoassay for Biomolecular Detection," Analytica Chimica Acta, vol. 910, pp. 12-24, (Mar. 2016).
Takulapalli et al., "High Density Diffusion-Free Nanowell Arrays," Journal of Proteome Research, vol. 11, pp. 4382-4391, (2012).
Heath et al., "Single Cell Analytic Tools for Drug Discovery and Development," Nature Reviews Drug Discovery, vol. 15(3), pp. 204-216, (Mar. 2016).
Oberleitner, "Thesis: Label-Free and Multi-Parametric Monitoring of Cell-Based Assays with Substrate-Embedded Sensors," Dissertation, University of Regensburg, (2015).
EPO; Extended European Search Report dated Dec. 11, 2019 in Application No. 17786594.6.
EPO; Examination Report dated Mar. 24, 2022 in Application No. 17786594.6.
CNIPA; Office Action dated Dec. 3, 2021 in Application No. 201780037937.8.

* cited by examiner

Nanopore array fabrication: Buffer / acid stop feedback etching of nanopores in KOH/TMAH or other chemicals wet etchants

When nanopore is formed, KOH/TMAH etchant comes in contact (mixes with) the Buffer/acid material placed on the other side of the wafer sample. This leads to neutralization of the wet etchant, in this case KOH/TMAH. This may be extended to other semiconductor materials with other wet etching and complementary etch-neutralization chemistries.

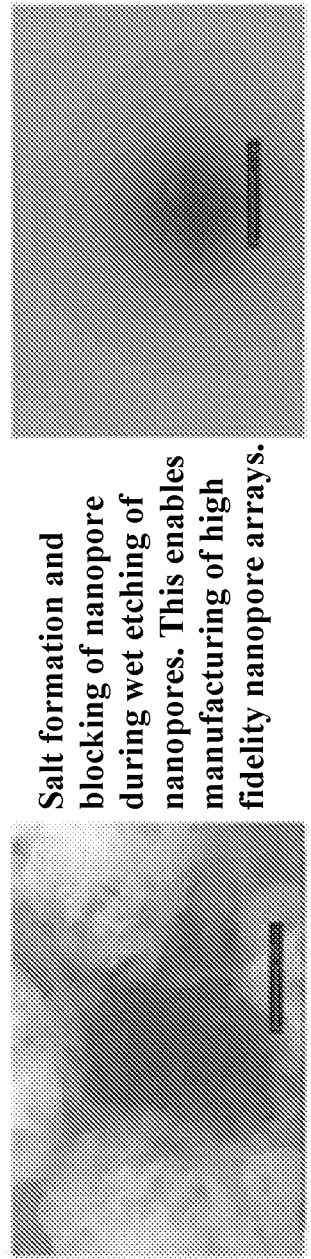

Salt formation and blocking of nanopore during wet etching of nanopores. This enables manufacturing of high fidelity nanopore arrays.

When wet etchant comes in contact with buffer/acid solution, neutralization may lead to formation of salt, instantly formed at the nanopore location. Composition and chemistry of salt formed can be designed, predetermined by selecting specific chemicals, polymers/monomers in buffers/acids and TMAH/KOH. Salt formed may be polymer material or organic or inorganic material or rubbery material. Salt formed at the naopore then physically prevents further etching of the nanopore, by stopping opening of the pore. This can be used to produce arrays of nanopores with good control of pore diameter and shape.

FIG. 47

NANOPORE SENSOR, STRUCTURE AND DEVICE INCLUDING THE SENSOR, AND METHODS OF FORMING AND USING SAME

CROSS-REFERENCE TO RELATED APPLICATIONS

This application is a U.S. National Phase filing under 35 U.S.C. § 371 of PCT Application Serial No. PCT/US2017/028468, which claims the benefit of U.S. Provisional Patent Application Ser. No. 62/324,352, entitled METHODS OF MAKING AND USING FIELD EFFECT NANOPORE TRANSISTOR FOR SENSING AND BIOPOLYMER SEQUENCING, and filed Apr. 19, 2016, the disclosures of which are incorporated herein by reference to the extent such disclosures do not conflict with the present disclosure.

FIELD OF THE INVENTION

The present disclosure generally relates to structures and devices for characterizing chemical and biological compounds. More particularly, the disclosure relates to sensors and devices suitable for detection and/or characterization of various materials and to methods of forming and using the sensors and devices.

BACKGROUND OF THE INVENTION

Various sensors can be used to detect and/or characterize materials, such as biological, chemical, and/or radiological materials. For example, nanopore or nanochannel sensors have been developed to detects and characterize (e.g., sequence) biological materials, such as DNA.

A DNA sequence is the linear sequence of the bases, from one end to the other, of a DNA strand. The simplest and most direct way to read this linear information chain is to probe/read it at a single point along the chain, one base at a time, successively, from end to end. Biological or solid-state nanopores aim to do this by threading DNA through a pore and reading (detecting) bases one-at-a-time as the DNA passes through the nanopore. Generally, nanopore sequencing requires neither DNA amplification nor other time consuming and costly steps used in current NGS sequencers.

A majority of nanopore sequencing technologies currently under commercialization are based on ion-current blockade sequencing and protein nanopore platforms. Other nanopore sequencing approaches being developed include: ion-current blockade approach with solid-state nanopores, graphene nanopores; tunneling-current based sequencing, optical dye based nanopore sequencing, and the like.

Almost all current nanopore sequencing approaches suffer from certain fundamental technical limitations. These include the following.

(1) Low Sequencing Accuracy:

A major advantage of nanopore sequencing is the localization of DNA sequence information at the nanopore aperture, i.e., complete sequence information available at the nanopore, as DNA passes through the nanopore. However, current nanopore sequencing methods cannot effectively sense and discriminate the passing DNA bases, due to low sensitivity of available nanopore base-sensing technologies. As a result, current nanopore sequencing methods yield low amplitude base signals measured against high background noise (or low signal-to-noise readouts), thereby introducing significant sequencing errors of 5% or more.

(2) Low Sequencing Speed:

A second major advantage of nanopore sequencing is that DNA naturally passes (translocates) through nanopores at speeds of million bases per second. If we can sense and readout DNA bases at such high megabase-per-second speeds, we can readily sequence whole genome (2×3 giga bases) in under 15 minutes using an array of just thousand nanopores. However, current nanopore sequencing methods fail to detect bases at such high speeds, and therefore use methods (such as using polymerase ratcheting) to slow-down the DNA to ten—few hundred bases per second. This effectively increases system complexity, sequencing time and introduces need for ~million nanopore arrays for whole genome sequencing.

(3) Complex Manufacturing:

Integrating solid state pores, lipid bilayer-like membranes, protein nanopores, polymerases (for ratcheting and slowing-down DNA), at scales of a hundred thousand to a million nanopores—is a technological and manufacturing challenge. Given the novelty of these nanopore sequencing platforms, it has not been feasible to achieve ultra-high fidelity device manufacturing, which in turns limits sequencing accuracy.

(4) Bio Fouling & Vibration Damage:

Protein nanopore based sequencers often require cold-chain and have shelf life issues due to potential for bio-fouling, and further are prone to vibration damage during shipping and handling.

These are likely the reasons for reported high error rates (>5%) of ion-current blockade based sequencers currently entering the market. Similarly, graphene nanopore and tunneling current based nanopore sequencing approaches suffer from low sensitivity, $1/f$ & $f^2$ noise and need for high-fidelity sub 2-nm manufacturing, which does not exist today.

A low cost, high quality solution for rapid sequencing and/or characterizing is therefore desirable. Such a technology at low cost could lead to true personalized diagnostics and personalized therapeutics, as well as to a better understanding of diseases and their causes. Accordingly, a device and method where the total cost, cumulative of devices, instrumentation, reagents, time-cost and other resources, is relatively low, i.e., a desktop sequencer that will enable monitoring of mutations over a period of time, and avails genome sequencing even to poorer countries, are desired.

SUMMARY OF THE INVENTION

The present invention provides improved devices and sensors that can be used to sense and characterize a variety of materials. The devices and sensors can be used for a variety of applications, including genome sequencing, protein sequencing, biomolecular sequencing, and detection of ions, molecules, chemicals, biomolecules, metal atoms, polymers, nanoparticles and the like. For example, the device can be used for detecting un-modified proteins, DNA and other biomolecules or proteins, DNA, biomolecules that have been modified with chemical tags or metal atom tags, nanoparticle tags, hybridization markers, or the like. Such detecting and characterizing can, in turn, be used to diagnose diseases.

In accordance with various embodiments of the disclosure, a method of forming a device includes providing a substrate comprising a semiconductor layer, etching a portion of the substrate to form a substrate etch region, forming a source region using a first portion of the semiconductor layer, forming a drain region using a second portion of the semiconductor layer, forming a channel using a third portion of the semiconductor layer, and forming one or more nanopores within the semiconductor layer. In accordance with exemplary aspects of these embodiments, the step of providing a substrate includes providing a substrate comprising semiconductor material, such as silicon, silicon on insulator, silicon on sapphire, silicon on silicon carbide, silicon on diamond, gallium nitride (GaN), GaN on insulator, gallium arsenide (GaAs), GaAs on insulator, germanium or germanium on insulator, or other semiconductor on insulator material, such as multi-layered semiconductor (e.g., silicon or others noted above) on insulator material. In accordance with further aspects of these embodiments, the method further comprises forming one or more etch regions in another semiconductor layer. In accordance with further aspects, the method includes forming a self-aligned structure overlying and aligned with the etch region within the semiconductor layer. Exemplary methods also include steps of forming doped regions—e.g., for forming source and drain regions of the device. In accordance with further exemplary aspects, spacers are formed about the self-aligned structures. And, in accordance with further examples of the disclosure, a moat is formed within the semiconductor layer surrounding the self-aligned structures. Exemplary methods can further include forming a gate oxide (that can include vertical and/or horizontal sections). Exemplary methods can further include forming a gate layer, which may be further patterned. Exemplary methods can further include a step of encapsulating a portion (e.g., a gate region) of the device. The method can further include forming gate contacts, source contacts, and drain contacts. Exemplary methods further comprise a step of forming a (e.g., self-aligned) nanopore. In accordance with yet further exemplary aspects of these embodiments, a method includes forming nano or microchannels. And, in accordance with yet further aspects, multiple devices can be formed about the one or more nanopores. In accordance with yet further aspects of these embodiments, the one or more nanopores are formed using a wet etchant, wherein nanopore formation is controlled by one or more of: (1) electric current feedback monitoring (2) capacitance measurement monitoring (3) chemical-stop etching, wherein etchant-chemical mixes with another chemical, such as a buffer or an acidic solution, upon nanopore formation and loses etching activity and (4) formation of a material-aggregate such as salt or polymer when etchant-chemical mixes with another chemical upon nanopore formation, wherein the material-aggregate physically stops further nanopore formation. In accordance with further aspects, during formation of the one or more nanopores, etching is stopped before the formation of the one or more nanopores based on a measurement of one or more of: electrical current measurement, capacitive measurement, resistance measurement, conductance measurement, or by monitoring transmission and/or absorption and/or reflection of light, ion beam, UV light, infra-red light, electron beam in the residual film.

In accordance with additional embodiments of the disclosure, a device includes a substrate, an etch region formed within a portion of the substrate, an insulating layer proximate the etch region, a semiconductor layer formed overlying the insulating layer, a source region formed using a first portion of the semiconductor layer, a drain region formed using a second portion of the semiconductor layer, a channel formed using a third portion of the semiconductor layer, wherein the channel spans between the source region and the drain region, and one or more nanopores formed within the semiconductor layer. In accordance with further aspects, the substrate is selected from the group consisting of silicon, silicon on insulator, silicon on sapphire, silicon on silicon carbide, silicon on diamond, GaN, GaN on insulator, gallium arsenide (GaAs), GaAs on insulator, germanium or germanium on insulator or other semiconductor on insulator material, such as multi-layered semiconductor (e.g., silicon or others noted above) on insulator material. In accordance with various aspects of these embodiments, the channel surrounds the one or more nanopores. In accordance with further aspects, two or more (e.g., all three) of a source contact, a drain contact, and a gate contact are formed on the same surface of the substrate. In accordance with further aspects, the device includes a gate oxide layer adjacent the channel. The gate oxide layer can include vertical and/or horizontal sections and/or C-shaped or V-shaped sections. The device can further include one or more sensitive layers and/or thin films coated on and overlying the channel, the one or more sensitive layers and/or thin films comprising one or more materials selected from the group consisting of: a chemical or biochemical or protein nanopore, an organic material, an inorganic material, a dielectric material, a metal, a semiconductor, graphene, and molybdenum disulfide ($MoS_2$) or similar other 2D material. Exemplary device can further include an encapsulant to encapsulate the device. The encapsulant can include one or more openings to allow material to come into contact with the device. In accordance with further aspects, the device includes one or more nano or micro fluidic channels formed on one or more surfaces of the device. And, in accordance with yet further examples of these embodiments, multiple devices are formed by stacking the device over another device—e.g., using 3D device technology, as an example by transferring one manufactured device layer over another device layer. In accordance with further exemplary embodiments of the disclosure, methods include forming semiconducting channel in contact with gate layer, without a gate oxide, forming MESFET like devices, enabling control of semiconductor channel using the gate layer and using these devices for biopolymer characterization or sequencing.

In accordance with further exemplary embodiments of the disclosure, a sensor device includes a substrate, a nanopore formed within the substrate, a plurality of devices surrounding the nanopore, wherein the each of the plurality devices produces a signal (e.g., mechanical, electrical, and/or optical) in response to detecting one or one or more ions, atoms, molecules, or particles traveling through the nanopore. The plurality of devices can be between 2 and 100, between 2 and 12, between 2 and 8 device, or between 4 and 8 devices. Each of the plurality of devices can be a field effect sensor, plasmonic sensor, interferometric sensor, wave-guide sensor, laser based sensor, cantilever sensor, acoustic sensor, QCM sensor, ultrasonic sensor, mechanical sensor, thermal sensor, fluorimetric sensor, optical dye based sensor, calorimetric sensor, luminometric sensor, quantum dot sensor, quantum-well sensor, graphene sensor, $MoS_2$ sensor, 2D material sensor, nanotube sensor, nanowire sensor, enzymatic sensor, electrochemical sensor, potentiometric sensor, and conductometric sensor or capacitive sensors or electron-spin sensor. In one embodiment, one or more of the plurality of sensors are Plasmonic sensors. Accordingly, an array of discrete islands or patterns of gold or silver or other Plasmonic materials are formed surrounding the nanopore, and used for biopolymer characterization and/or sequencing using methods known to those familiar with the field of art, such as but not limited to that described in: Plasmonic Sensors for Disease Detection—A Review, Barizuddin S, Bok S, and Gangopadhyay S, J Nanomed Nanotechnol 2016, 7:3 http://dx.doi.org/10.4172/2157-7439.1000373, In one embodiment, one or more of the plurality of devices can be a field effect sensor and include a channel region proximate the nanopore, a source region and a drain region, wherein the source region is formed proximate a first surface of a layer comprising the nanopore and the drain region is formed proximate a second surface of the layer comprising the nanopore. One or more of the plurality of devices can include a vertical and/or C-shaped (concave or convex) and/or V-shape and/or horizontal gate structure. Two or more (e.g., all three) of a source contact, a drain contact, and a gate contact are formed on the same surface of the substrate. Double stranded DNA and/or RNA forms a helical structure with known rise, twist and pitch. Single stranded DNA and/or RNA also form helical structures in specific solutions conditions. In addition, DNA and/or RNA are known to form triple-strands and quadraplex strands, with known parameters. As DNA passes through nanopore surrounded by plurality of sensor devices, the rise and twist of the DNA and/or RNA can be detected using successive sensor devices as the DNA rotates and passes through the nanopore. A given device in the plurality of the devices surrounding the nanopore interacts with one side/part/edge/base of the DNA and/or RNA approximately once every time the DNA travels by distance equal to the pitch. This increased sensor interaction distance from base to base provides increased resolution of base detection and sequencing, for higher accuracy.

The plurality of devices can be used to detect or sequence one or more of molecules, biopolymers, DNA, RNA, polypeptides, proteins, and lipids, or detect rotation of single strand DNA or double strand DNA or multi-strand DNA or protein or polypeptide or modified protein, or sequence single stranded DNA/RNA or double strand DNA/RNA or sequence multi-strand DNA or sequence protein or polypeptide or modified protein, or to detect potential or charge or workfunction or dipole moment on molecules or chemical substances or biopolymers or DNA or Protein or RNA or double stranded DNA, for sequencing or biomarker detection or diagnostic purposes, or characterize or sequence double stranded DNA by sensing successive DNA bases or modifiers of DNA bases as the double stranded DNA rotates and passes through one or more nanopores, wherein the base to base distance on any given side/angle of double stranded DNA is approximately 3.5 nm, increased base-to-base separation on one side/angle providing for discriminated detection of bases for characterization or sequencing.

In accordance with additional embodiments, a method includes providing one or more of the devices (including sensor devices) as described herein, passing the biological or chemical substance through one of the one or more nanopores, and, using the one or more devices, detecting a signal as the substance passes through one of the one or more nanopores. In accordance with various aspects of these embodiments, the substance is selected from one or more of: a biological, chemical, organic, or inorganic substance, a particle, or ion. In accordance with further aspects, the characterizing includes sequencing. The sequencing can be, for example, sequencing one or more of DNA, RNA, proteins, polypeptides, glycans, lipids, and other biopolymers. In accordance with further aspects, characterizing includes one or more of detecting epigenetic markers or epigenetic factors such as but not limited to DNA methylation, acetylation, histone modifications, detecting post-translational-modifications on proteins and/or protein mutations, detecting transport of ions or small chemical or biomolecules, extending a fully folded 3D protein or protein fragment into a continuous amino acid string, from n to c terminus, which are then sequenced, fragmenting a full protein into parts or polypeptides and then sequencing few or all of the fragmented parts or polypeptides, fragmenting a full protein into parts or polypeptides, modifying the full protein or the fragments and then detecting the modifiers on protein or the fragmented parts.

In accordance with additional exemplary embodiments of the disclosure, a method of diagnosing a disease includes using any of the methods, devices, or sensors described herein. In accordance with various aspects of these embodiments, the disease includes cancer. In accordance with various aspects of these embodiments, the disease includes autoimmune diseases. In accordance with various aspects of these embodiments, the disease includes infectious diseases. In accordance with various aspects of these embodiments, the disease includes cardiovascular diseases. In accordance with various aspects of these embodiments, the disease includes Alzheimer's or other neurodegenerative disease(s). When the disease includes Alzheimer's or other neurodegenerative disease(s), the method can include characterizing PTMs or mutations or sequencing one or more of, but not limited to, Tau protein, amyloid protein, alpha-synucleic.

In accordance with yet further embodiments, an apparatus includes one or more pumps to pump an etchant to a surface of a substrate, a plurality of tubes coupled to the pump to provide etchant to the surface, and at least one tube to remove etchant from the surface, wherein the plurality of tubes provide the etchant to a portion of the surface. The apparatus can include a positioning system to move the plurality of tubes, and/or an automated system and/or a robotic systems, and the at least one tube from one array area to another array area. The array area can include 1 to 10,000 nanopores. The plurality of tubes can surround the at least one tube.

BRIEF DESCRIPTION OF THE DRAWING FIGURES

The exemplary embodiments of the present invention will be described in connection with the appended drawing figures.

FIG. 47 illustrate salt formation during a nanopore formation process device in accordance with additional exemplary embodiments of the disclosure.

Figure 1:
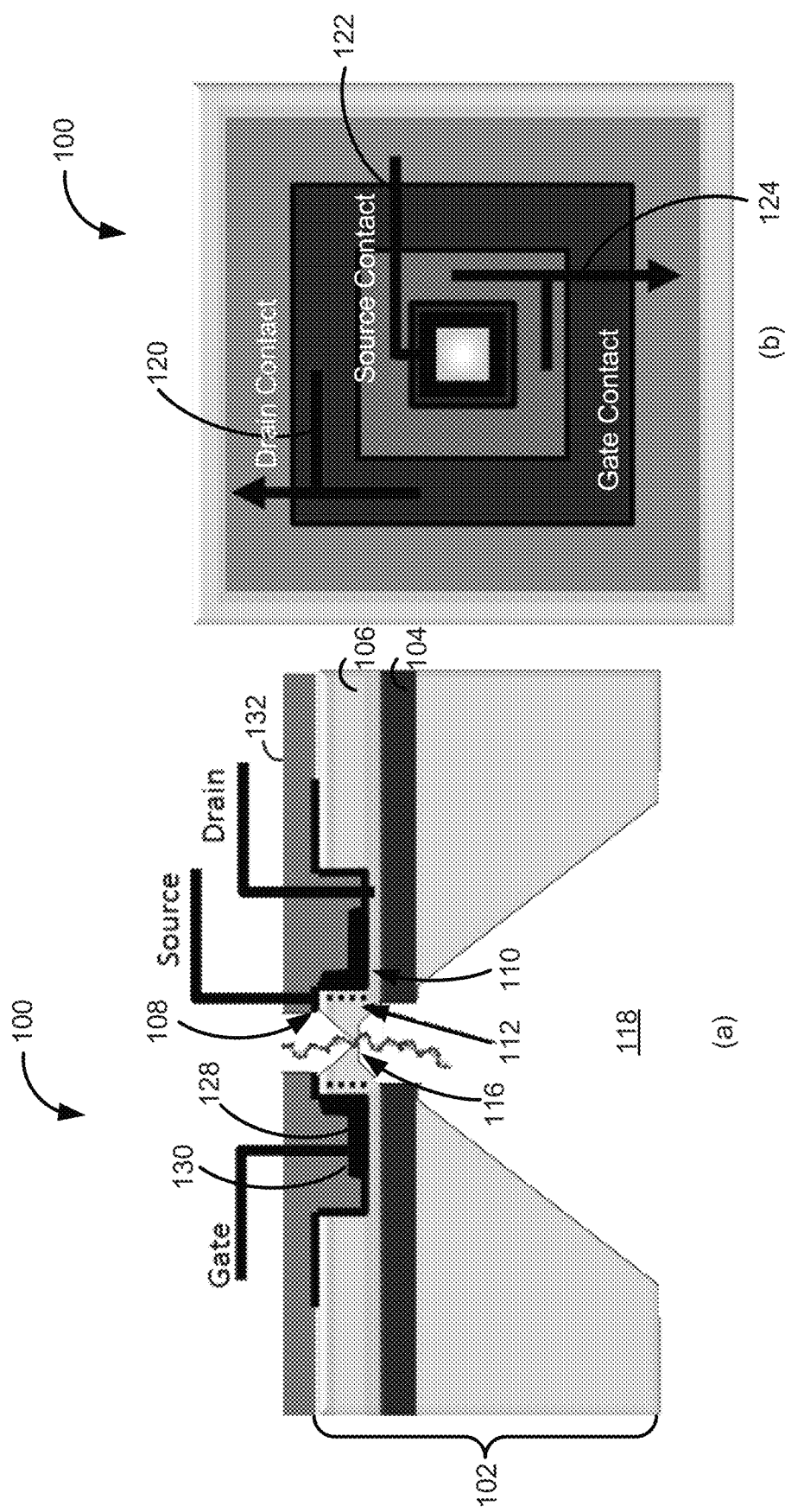
FIG. 1 illustrates (a) a cross-sectional view and (b) a top view a device in accordance with exemplary embodiments of the disclosure.

It will be appreciated that the figures are not necessarily drawn to scale. For example, the dimensions of some of the elements in the figures may be exaggerated relative to other elements to help to improve understanding of illustrated embodiments of the present invention.

DETAILED DESCRIPTION OF PREFERRED EMBODIMENTS OF THE INVENTION

The description of exemplary embodiments of the present disclosure provided below is merely exemplary and is intended for purposes of illustration only; the following description is not intended to limit the scope of the invention disclosed herein. Moreover, recitation of multiple embodiments having stated features is not intended to exclude other embodiments having additional features or other embodiments incorporating different combinations of the stated features.

As set forth in more detail below, various embodiments of the disclosure provide devices and sensors capable of rapidly sequencing or otherwise characterizing and/or detecting various materials. In accordance with some aspects of the disclosure, rather than slowing down the DNA or other material to be characterized, ultrasensitive and ultrafast sensors and devices can rapidly characterize the materials as the material passes through a nanopore at high speeds (e.g., in the case of DNA and the like, it is thought that about million bases per second with mega base read lengths can be characterized). An exemplary novel nanopore sensor, termed Field Effect Nanopore Transistor (FENT), combines the advantages of nanopore sequencing with the high detection sensitivity and gigahertz switching speeds of, for example, semiconductor field effect transistor sensor technology. Since FENT can be based on CMOS chip manufacturing, systems-on-chip integration (SOC) with ASICs, signal processors, memory and other components can be integrated to enable an ultra-compact whole genome sequencing platform that is relatively inexpensive. Additionally or alternatively, multiple devices can be formed about one or more nanopores through which that material passes. In these cases, rotational, rise, twist, pitch and other information can be gathered, and multi-stranded DNA, as well as other materials can be characterized.

In accordance with various embodiments of the disclosure, devices and sensors described herein can be used to integrate nanopore sequencing approach with field effect transistor sensing. A nano-scale fully-depleted field effect transistor (FET) sensor can be fabricated surrounding one or more nanopores at the center. This can be visualized as an ultra-sensitive three dimensional (3D) nanowire transistor sensor wrapped around a nanopore. Electron inversion channel current can be established in the transistor by applying voltage to the buried transistor gate. In another embodiment, inversion channel can be established in the transistor without applying any gate voltage. Once established, this inversion channel current is extremely sensitive to biomolecular electrostatic interactions occurring at the nanopore aperture. Biomolecular electrostatic interactions (minute charge or potential variations) occurring at the nanopore aperture scatter or perturb the electron inversion channel to modulate the measured transistor current, thus enabling ultra-sensitive biomolecular detection.

In exemplary devices and sensors described herein, electrostatic interactions at the nanopore aperture can be amplified twice to result in ultra-high sensitivity signal detection. Firstly, in fully-depleted FET sensors small variations in charge or potential or workfunction at the surface of the sensor are amplified up to an order of magnitude by the fully depleted device structure. Secondly, in a FENT nanopore transistor, electric field focusing occurs at the sharp nanopore edge and any electrostatic interactions/variations at the nanopore aperture are 'edge-field amplified' by up to an order of magnitude. This compounded double amplification confers ultra-high sensitivity to FENT nanopore transistor device. Furthermore, noise in transistor devices reduces drastically with increasing operational frequency. Since FENT will be operated close to or above 100 MHz speeds, noise amplitudes will be in nano amperes or sub-nano amperes or tens of pico-amperes or less. FENT ultra-high detection sensitivity combined with low noise results in high signal-to-noise ratio base readouts, enabling high accuracy sequencing and characterization of biopolymers such as DNA, RNA, lipids, glycans and poly-peptides.

As set forth in more detail below, the devices can be used to characterize various substances. In the case of DNA, DNA naturally passes through nanopores at speeds of up to and above million bases per second, depending on nanopore substrate and specific conditions, under electrophoresis. However in 'ion current blockade' based sequencing methods fundamental physics of ion transport in aqueous solutions limits sensitivity and sequencing speed. In 'ion current blockade' sequencing, DNA bases (or strands) differentially block a ~2 nm nanopore aperture and the ions slipping past the blocked-nanopore are measured using electrodes on either side of the nanopore. The essential idea is that, as different bases sterically block the nanopore aperture to different extents, ions slipping past the nanopore aperture constitute an ion current signature unique to the blocking-base (or strand), enabling base readout. Ions therefore are the carriers of base-specific information from nanopore-aperture to the ion sensing electrodes. However, ions in aqueous solutions follow Brownian dynamics owing to continuous collisions resulting in very low mobilities on the order of 0.001 cm$^2$/(V·s). Speed or velocity of ion transport is directly dependent on ion mobilities. As a result of these ultra-low ion mobilities, ion current blockade method is limited to sequencing speeds of ten to hundred bases per second. Consequently, researchers had to develop techniques such as polymerase ratcheting to slow the DNA translocation through nanopores, to be able to sequence using ion-current blockade method.

In a FENT nanopore transistor, device, 'electrons' (or holes) can be carriers of DNA base information. Base-specific electrostatic interactions at the nanopore aperture scatter or perturb inversion electron current in the transistor device, and the measured transistor current is analyzed to discriminate and detect DNA bases for sequencing. Electrons are wave-particles that travel through silicon crystal lattice without significant scattering, and have carrier mobilities on the scale of 1000 cm$^2$/(V·s). These high electron mobilities are the fundamental reason silicon chip processors in computers and mobile phones function at gigahertz speeds (giga hertz is $10^9$ cycles per second). Therefore, electrons in FENT nanopore transistor have $10^6$ or million times higher mobilities than ions in ion-current-blockade method. This implies, FENT nanopore transistor device should be able to sequence DNA with up to million times higher speeds compared to ion-current-blockade method. Consequently a FENT nanopore transistor device can be operated at 100 mega-hertz to gigahertz speeds, to sequence the DNA at speeds of $10^5$ to million bases per second. Due to these reasons, FENT nanopore transistor sequencer will enable ultra-fast sequencing of whole genome within 15 minutes, at a very lost cost (not possible with known other technologies)—effectively revolutionizing healthcare.

DNA bases (A, G, C, and T) are organic molecules with minor variations in molecular structure from one base to another, which confers unique properties to each of the bases. These molecular differences between bases manifest as unique base-specific electrostatic surface potentials (voltage on surface of base molecules), which can conversely be thought of in terms of base-specific electrostatic surface charges (partial) or corresponding base-specific dipole moments. Surface potentials of bases are known to differ from one other by up to 50 micro-volts ($\mu V$) or more. Hence, discriminated detection of base-specific electrostatic surface potential differences will enable direct sequencing of un-modified single strand DNA. However, this will require incorporating an ultra-sensitive sensor surrounding the nanopore aperture that is capable of detecting base-specific electrostatic variations—which is elegantly enabled by ultra-sensitive FENT nanopore transistor device structure.

As single stranded DNA to be sequenced passes through the FENT nanopore aperture, bases successively present themselves at the nanopore-aperture and sequentially interact with the ultra-sharp nanopore edge (atomic scale thin nanopore edge). FENT nanopore transistor sensor will detect the surface potential differences or surface charges or dipole moments of successive bases passing through the nanopore, to discriminate between the bases and sequence the DNA strand. In FENT structure, base-specific electrostatic surface potentials are first edge-field amplified at nanopore edge and resulting amplified base-potentials 'gate' the inversion current established in the fully-depleted strongly coupled FENT device—resulting in doubly-amplified modulation of measured transistor device current. A, G, C and T base-specific surface potentials 'gate' the transistor conductivity, to produce corresponding four different current levels, which are processed using advanced digital signal processing algorithms, enabling high-accuracy sequencing of DNA.

Ion-current-blockade sequencing with protein nanopores or solid state nanopores is one of the most popular nanopore sequencing approaches (as it mimics the very familiar cell membrane protein nanopores and patch clamp measurements). However, ion-current method lacks the sensitivity to detect and discriminate minute base-specific variations in atomic configuration or charge/potential. To address this fundamental issue special chemical and enzymatic methods have been developed to modify DNA bases with tags, where each base is modified with a unique atomic scale tag. Distinguishing features of labeling tags can be tag size or chemical properties or electronic properties or steric configuration; in other words, any feature that magnifies the distinction between the bases (molecular tags, fluorescent tags, metal ion tags, and the like). Kilo-base length DNA single strands can readily be tagged using polymerase enzyme, using commercially available kits. The ultra-sensitive FENT nanopore transistor sensor can readout the tagged bases with ultra-high accuracy, in a few seconds or less. This FENT tag sequencing approach can instantly be used for genomic biomarker detection, in diagnostic applications, and the like.

Although portions of this disclosure describe FENT devices and DNA sequencing, unless otherwise noted, the disclosure or claims are not limited to such examples. For example, as set forth in more detail below, sensor device can include one or more other forms of devices (other than a field-effect transistor) that surround one or more nanopores.

Exemplary Device Structures

FIG. 1 illustrates (a) a cross-sectional view and (b) a top view of a device 100 in accordance with various exemplary embodiments of the disclosure. Device 100 includes a substrate 102, an etch region 118 formed within a portion of substrate 102, an insulating layer 104 proximate etch region 118, a semiconductor layer 106 formed overlying insulating layer 104, a source region 108 formed using a first portion of the semiconductor layer 106, a drain region 110 formed using a second portion of the semiconductor layer 106, a channel 112 formed using a third portion of semiconductor layer 106, wherein channel 112 spans between source region 108 and the drain region 110, and one or more nanopores 116. As illustrated, channel 112 surrounds one or more nanopores 116. Device 100 can also include a encapsulant 132. Device 100 may additionally include additional insulating, semiconductive, and conductive layers, such as those described in more detail below.

Device 100 can operate in inversion mode, fully depletion mode, partial depletion mode, depletion mode, or in accumulation mode. As illustrated in FIG. 1(*a*), an inversion channel 112 may be formed within a portion of layer 106 proximate nanopore 116 by controlling a voltage bias applied to gate contact 124, or by biasing the solution, or both. It is also possible that the inversion channel is formed in layer 106 with no external bias applied to device 100, depending on a doping level in layer 106, thickness of layer 106, other such variables, and, for example, a fixed oxide charge density and interface trap states density at its boundaries. A thickness of layer 106 can be from, for example, about 1 nm to 50 microns (e.g., about 200 nm, 1 micron), depending on the material (e.g., semiconductor material) and its doping density.

As used herein, unless stated otherwise, overlying is not restricted to meaning that a layer overlying another layer must be immediately adjacent the other layer. Various layers may be interposed between a substrate or layer and another layer overlying the substrate or layer. Further, as used herein, a first surface and a second surface are not on a same side (e.g., top or bottom) of a structure or device or layer, and in the illustrated examples are on opposite sides—top and bottom—of a substrate/device.

Substrate 102 may be formed of a variety of materials. For example, substrate 102 may include buried insulating material, semiconductor material and/or a buried metal layer. By way of examples, substrate 102 includes one or more semiconductive layers and one or more buried insulating (e.g., oxide layers). Examples of substrate 102 semiconductor-on-insulator substrates, include one or more semiconductive layers and one or more insulating layers. Exemplary substrates are discussed in more detail below. Further examples of substrate 102 materials include, but are not limited to, semiconductors and metals, including silicon, germanium, graphene, diamond, tin or compound semiconductors like silicon carbide, silicon germanium, diamond, graphite, binary materials like aluminium antimonide (AlSb), aluminium arsenide (AlAs), aluminium nitride (AlN), aluminium phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cuprous chloride (CuCl), lead selenide (PbSe), lead sulfide (PbS), lead telluride (PbTe), tin sulfide (SnS), tin telluride (SnTe), bismuth telluride (Bi2Te3), cadmium phosphide (Cd3P2), cadmium arsenide (Cd3As2), cadmium antimonide (Cd3Sb2), zinc phosphide (Zn3P2), zinc arsenide (Zn3As2), zinc antimonide (Zn3Sb2), other binary materials like lead(II) iodide (PbI2), molybdenum disulfide (MoS2), gallium Selenide (GaSe), tin sulfide (SnS), bismuth Sulfide (Bi2S3), platinum silicide (PtSi), bismuth(III) iodide (BiI3), mercury(II) iodide (HgI2), thallium(I) bromide (TlBr), semiconducting oxides like zinc oxide, titanium dioxide (TiO2), copper(I) oxide (Cu2O), copper(II) oxide (CuO), uranium dioxide (UO2), uranium trioxide (UO3), 6.1 A materials, or ternary materials like aluminium gallium arsenide (AlGaAs, AlxGa1−xAs), indium gallium arsenide (InGaAs, InxGa1-xAs), aluminium indium arsenide (AlInAs), aluminium indium antimonide (AlInSb), gallium arsenide nitride (GaAsN), gallium arsenide phosphide (GaAsP), aluminium gallium nitride (AlGaN), aluminium gallium phosphide (AlGaP), indium gallium nitride (InGaN), indium arsenide antimonide (InAsSb), indium gallium antimonide (InGaSb), cadmium zinc telluride (CdZnTe, CZT), mercury cadmium telluride (HgCdTe), mercury zinc telluride (HgZnTe), mercury zinc selenide (HgZnSe), lead tin telluride (PbSnTe), thallium tin telluride (Tl2SnTe5), thallium germanium telluride (Tl2GeTe5) and quaternary like aluminium gallium indium phosphide (AlGaInP, InGaP, InGaAlP, AlInGaP), aluminium gallium arsenide phosphide (AlGaAsP), indium gallium arsenide phosphide (InGaAsP), aluminium indium arsenide phosphide (AlInAsP), aluminium gallium arsenide nitride (AlGaAsN), indium gallium arsenide nitride (InGaAsN), indium aluminium arsenide nitride (InAlAsN), copper indium gallium selenide (CIGS), or quinary materials like gallium indium nitride arsenide antimonide (GaInNAsSb), Mg, Al, Sc, Ti, V, Cr, Mn, Fe, Co, Ni, Cu, Zn, Ga, Y, Zr, Nb, Mo, Ru, Rh, Pd, Ag, La, Hf, Ta, W, Re, Os, Ir, Pt, Au, TaTi, Ru, HfN, TiN, and the like. Substrate 102 may include inorganic or organic semiconducting material as described in more detail below in connection with layer 106. In flexible devices this layer includes a flexible substrate, such as, for example an organic material like pentacene.

Insulating layer 104 may be formed of any suitable insulating material. In accordance with exemplary aspects of various exemplary embodiments of the disclosure, insulating layer 104 is buried insulating layer that can form part of a semiconductor-on-insulator substrate. In other words, insulating layer can be a buried insulating or oxide layer. Insulating layer 104 can be made of any suitable organic or inorganic insulating material. Examples include, but are not limited to, silicon dioxide, silicon nitride, hafnium oxide, alumina, magnesium oxide, zirconium oxide, zirconium silicate, calcium oxide, tantalum oxide, lanthanum oxide, titanium oxide, yttrium oxide, titanium nitride, and the like. By way of one example, insulating layer 104 is a buried oxide layer in silicon-on-insulator substrate. The thickness of this layer can be from, for example, about 1 nm to 100 microns or be about 200 nm.

In the illustrated example, source region 108, drain region 110, and channel 112 are formed using semiconductor layer 106. Semiconductor layer 106 can form part of substrate 102—e.g., when substrate 102 includes a semiconductor on insulator substrate. By way of one example, semiconductor layer 106 includes crystalline silicon film. Layer 106 may include, for example, crystalline or amorphous inorganic semiconductor material, such as those used in the regular MOS technologies. Exemplary semiconductor materials include, but are not limited to, elemental semiconductors like silicon, germanium, graphene, diamond, tin or compound semiconductors like silicon carbide, silicon germanium, diamond, graphite, binary materials like aluminium antimonide (AlSb), aluminium arsenide (AlAs), aluminium nitride (AlN), aluminium phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cuprous chloride (CuCl), lead selenide (PbSe), lead sulfide (PbS), lead telluride (PbTe), tin sulfide (SnS), tin telluride (SnTe), bismuth telluride (Bi2Te3), cadmium phosphide (Cd3P2), cadmium arsenide (Cd3As2), cadmium antimonide (Cd3Sb2), zinc phosphide (Zn3P2), zinc arsenide (Zn3As2), zinc antimonide (Zn3Sb2), other binary materials like lead(II) iodide (PbI2), molybdenum disulfide (MoS2), gallium Selenide (GaSe), tin sulfide (SnS), bismuth Sulfide (Bi2S3), platinum silicide (PtSi), bismuth(III) iodide (BiI3), mercury(II) iodide (HgI2), thallium(I) bromide (TlBr), semiconducting oxides like zinc oxide, titanium dioxide (TiO2), copper(I) oxide (Cu2O), copper(II) oxide (CuO), uranium dioxide (UO2), uranium trioxide (UO3), 6.1 A materials, or ternary materials like aluminium gallium arsenide (AlGaAs, AlxGa1−xAs), indium gallium arsenide (InGaAs, InxGa1−xAs), aluminium indium arsenide (AlInAs), aluminium indium antimonide (AlInSb), gallium arsenide nitride (GaAsN), gallium arsenide phosphide (GaAsP), aluminium gallium nitride (AlGaN), aluminium gallium phosphide (AlGaP), indium gallium nitride (InGaN), indium arsenide antimonide (InAsSb), indium gallium antimonide (InGaSb), cadmium zinc telluride (CdZnTe, CZT), mercury cadmium telluride (HgCdTe), mercury zinc telluride (HgZnTe), mercury zinc selenide (HgZnSe), lead tin telluride (PbSnTe), thallium tin telluride (Tl2SnTe5), thallium germanium telluride (Tl2GeTe5) and quaternary like aluminium gallium indium phosphide (AlGaInP, InAlGaP, InGaAlP, AlInGaP), aluminium gallium arsenide phosphide (AlGaAsP), indium gallium arsenide phosphide (InGaAsP), aluminium indium arsenide phosphide (AlInAsP), aluminium gallium arsenide nitride (AlGaAsN), indium gallium arsenide nitride (InGaAsN), indium aluminium arsenide nitride (InAlAsN), copper indium gallium selenide (CIGS), or quinary materials like gallium indium nitride arsenide antimonide (GaInNAsSb), and the like.

Semiconductor layer 106 can also be made of organic semiconducting materials. Examples of such materials include, but are not limited to, polyacetylene, polypyrrole, polyaniline, Rubrene, Phthalocyanine, Poly(3-hexylthiophene, Poly(3-alkylthiophene), α-ω-hexathiophene, Pentacene, α-ω-di-hexyl-hexathiophene, α-ω-dihexyl-hexathiophene, Poly(3-hexylthiophene), Bis(dithienothiophene, α-ω-dihexyl-quaterthiophene, Dihexyl-anthradithiophene, n-decapentafluoroheptylmethylnaphthalene-1,4,5,8-tetracarboxylic diimide, α-ω-dihexyl-quinquethiophene, N,N'-dioctyl-3,4,9,10-perylene tetracarbozylic, CuPc, Methanofullerene, [6,6]-phenyl-C61-butyric acid methyl ester (PCBM), C60, 3',4'-dibutyl-5-5bis(dicyanomethylene)-5,5'-dihydro-2,2':5',2"terthiophene (DCMT), PTCDI-C5, P3HT, Poly(3,3"-dialkyl-terthiophene), C60-fused N-methylpyrrolidine-meta-C12 phenyl (C60MC12), Thieno[2,3-b]thiophene, PVT, QM3T, DFH-nT, DFHCO-4TCO, BBB, FTTTTF, PPy, DPI-CN, NTCDI, F8T2-poly[9,9' dioctylfluorene-co-bithiophene], MDMO-PPV-poly[2-methoxy-5-(3,7-dimethyloctyloxy)]-1,4-phenylenevinylene, P3HT-regioregular poly [3-hexylthiophene]; PTAA, polytriarylamine, PVT-poly-[2,5-thienylene vinylene], DH-5T-α,ω-Dihexylquinquethiophene, DH-6T-α,ω-dihexylsexithiophene, phthalocyanine, α-6T-α-sexithiophene, NDI, naphthalenediimide, F16CuPc-perfluorocopperphthalocyanine, perylene, PTCDA-3,4,9,10-perylene-tetracarboxylic dianhydrid and its derivates, PDI-N,N'-dimethyl 3,4,9,10-perylene tetracarboxylicdiimide, and the like.

Semiconductor layer 106 can include topological insulator materials such as bismuth antimonide, pure antimony, bismuth selenide, bismuth telluride, antimony telluride, or alternate topological insulator materials known to those familiar with the field of invention. Alternately topological material thin films can be formed on layer 106.

Semiconductor layer 106 can include intrinsic or p-type or n-type doped material; correspondingly device 100 can be an n-channel device or a p-channel device, respectively. One exemplary layer 106 includes 1 E14 doped p-type silicon layer of thickness between about 10 nm and about 1000 nm.

As discussed in more detail below, source region 108 and drain region 110 can be formed by doping regions of semiconductor layer 106. A gate region, including a gate oxide 128 and a gate metal 130 can be formed adjacent portions of semiconductor layer 106, as described in more detail below. As further described below, gate oxide 128 and/or gate metal 130 can include vertical and/or horizontal and/or C-shaped and/or V-shaped sections as illustrated in FIG. 1. The source, drain, and/or gate can all have contacts 120, 122, and 124 that are formed on the same surface of substrate 102. Alternatively, at least two of the contacts 120, 122, and 124 are formed on the same surface/side of substrate 102.

Figure 2:
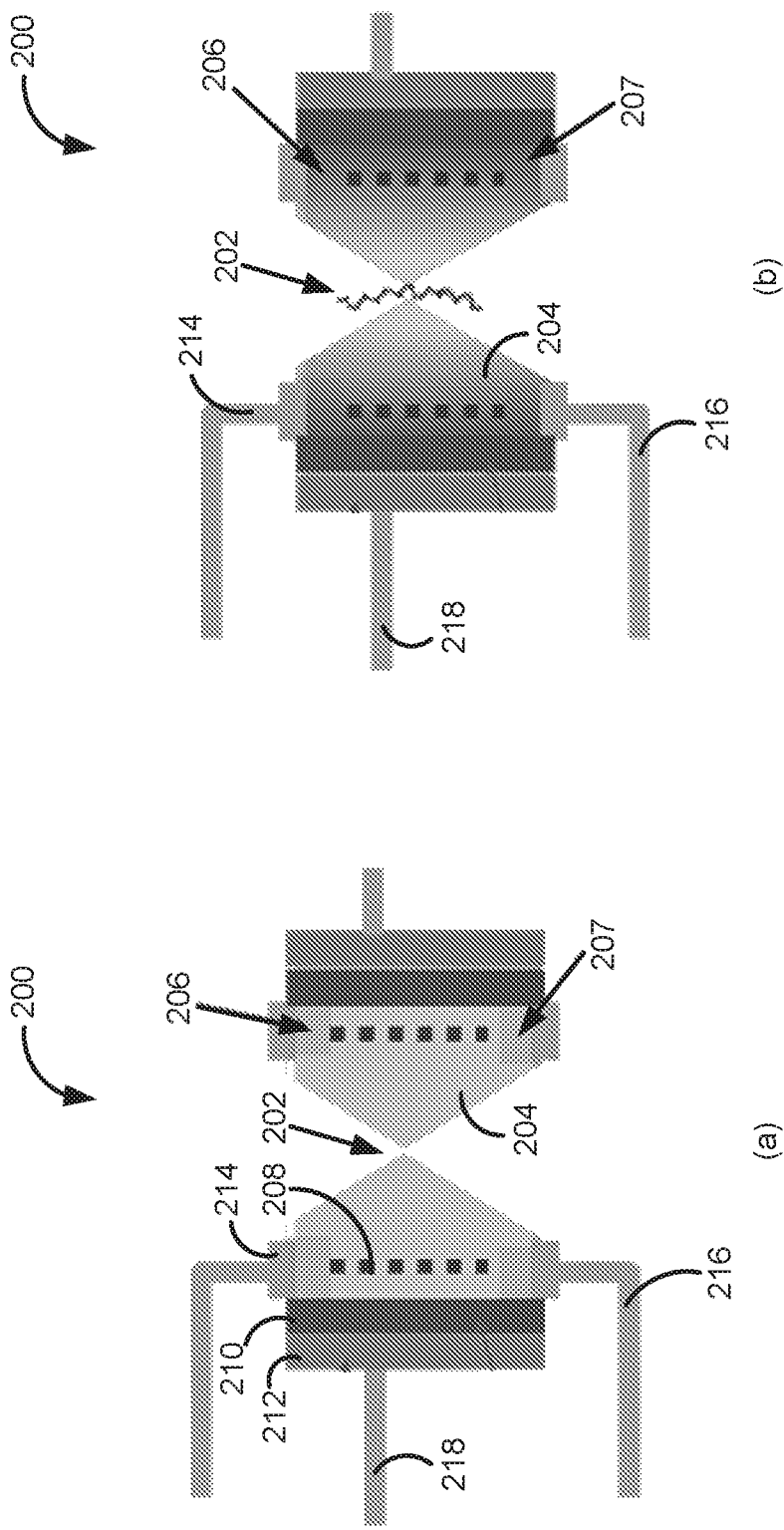
FIG. 2 illustrates (a) a simplified view of a device in accordance with exemplary embodiments of the disclosure (b) an illustration of the device in operation.
Figure 3:
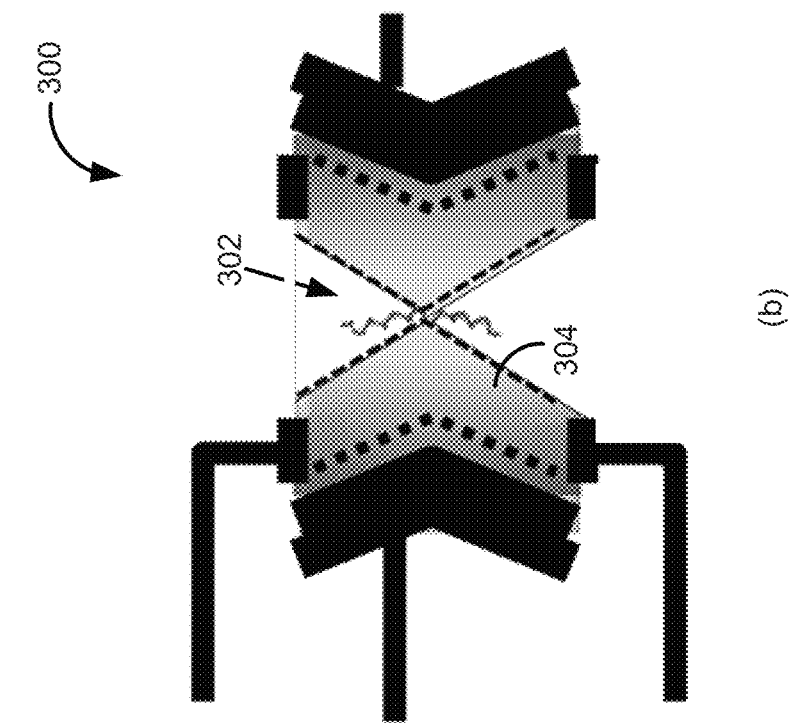
FIG. 3 illustrates (a) another simplified view of a device in accordance with exemplary embodiments of the disclosure (b) an illustration of the device in operation.
Figure 3:
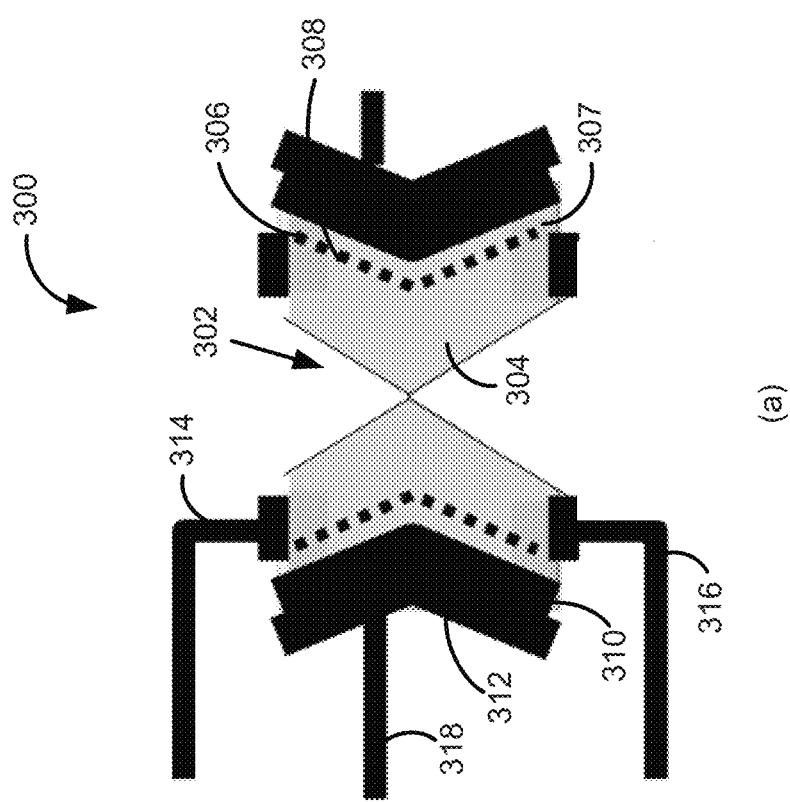

FIGS. 2 and 3 illustrate cross-sectional views of devices 200 and 300 in simplified form in accordance with exemplary embodiments of the disclosure. Device 200 can be the same or similar as device 100, but is illustrated in simplified form. Device 300 is similar to devices 100 and 200, except device 300 includes a C-shaped or a V-shaped channel and gate regions.

Referring now to FIGS. 2(a) and (b), device 200 includes a nanopore 202 formed within a semiconductor layer 204, a source region 206 formed on one side of semiconductor layer 204, a drain region 207 formed on the other side of semiconductor layer 204, a channel 208 formed between the source and drain regions, a gate oxide 210 formed adjacent channel region 208, and a gate metal 212 formed adjacent gate oxide 210. Device 200 also includes source contact 214, drain contact 216, and gate contact 218. In the illustrated example, gate oxide 210 and gate metal 212 include vertical sections. The various layers and regions of device 200 can be the same or similar to those of device 100 described above.

FIG. 2(b) illustrates device 200 during operation, in which material (e.g. a DNA strand) is being characterized (e.g., sequenced). During operation, device 200 can operate as a fully-depleted FENT device by electrostatic scattering of inversion/accumulation current by base-specific surface potentials.

FIGS. 3(a) and (b) illustrate device 300 is accordance with additional examples of the disclosure. Device 300 includes a nanopore 302 formed within a semiconductor layer 304, a source region 306 formed on one side of semiconductor layer 304, a drain region 307 formed on the other side of semiconductor layer 304, a channel 308 formed between the source and drain regions, a gate oxide 310 formed adjacent channel region 308, and a gate metal 312 formed adjacent gate oxide 310. Device 300 also includes source contact 314, drain contact 316, and gate contact 318. The various layers and regions of device 300 can be the same or similar to those of device 100 described above. As noted above, device 300 is similar to device 200, except for the shape of the gate structure that includes gate oxide 310 and gate metal 312. Although illustrated with a V-shape, devices in accordance with various embodiments of the disclosure can include gate structures that are C-shaped (convex or concave). Techniques to form the shaped gate structure are described below.

FIG. 3(b) illustrates device 300 during operation, in which material (e.g. a DNA strand) is being characterized (e.g., sequenced). During operation, device 300 can operate as a fully-depleted FENT device by electrostatic scattering of inversion/accumulation current by base-specific surface potentials.

Although not illustrated, devices 100-300 can include one or more additional layers overlying the channel (e.g., channel 112). The additional layer can include material to additionally functionalize devices 100-300. The additional layers can be, for example, a thin film that is of thickness between 2 angstroms and 100 nm. The additional layer can include, for example, monolayer or multilayer of organic molecules or biomolecules; thin films of semiconducting materials, metals, semi metals, insulators, dielectric materials, metamaterials, or the like that may be additionally used to functionalize the device.

The additional layer(s) can include multilayers, where first layer is a thin film of one or more materials described above, and a second layer that is made with biological nano or micro pore molecules such as protein nanopore, alpha hemolysin, beta barrel, or DNA base nanopores or other biological or organic molecule based nanopore or micro pores. The additional layer(s) can include at least one lipid bilayer overlaying a nanopore or chemical nanopore material. By way of examples, the additional layers can include one or more sensitive layers coated on and overlying the channel, the one or more sensitive layers including one or more materials selected from the group consisting of: a chemical or biochemical or protein nanopore, an organic material, an inorganic material, a dielectric material, a metal, a semiconductor, graphene, and molybdenum disulfide ($MoS_2$). Additionally or alternatively, devices described herein can include one or more thin films coated on and overlying the channel, the one or more thin films comprising one or more materials selected from the group consisting of: a chemical or biochemical or protein nanopore, an organic material, an inorganic material, a dielectric material, a metal, a semiconductor, graphene, and $MoS_2$.

The additional layers can be deposited using any of the thin film fabrication techniques, such as electrolytic deposition, electrochemical deposition, sputtering, chemical vapor deposition, physical vapor deposition, epitaxy, atomic layer deposition (ALD), molecular beam epitaxy, e-beam thermal deposition, thermal deposition of other kinds, or any other deposition techniques for thin films or chemical deposition methods of single molecule monolayers or multilayers.

Figure 46:
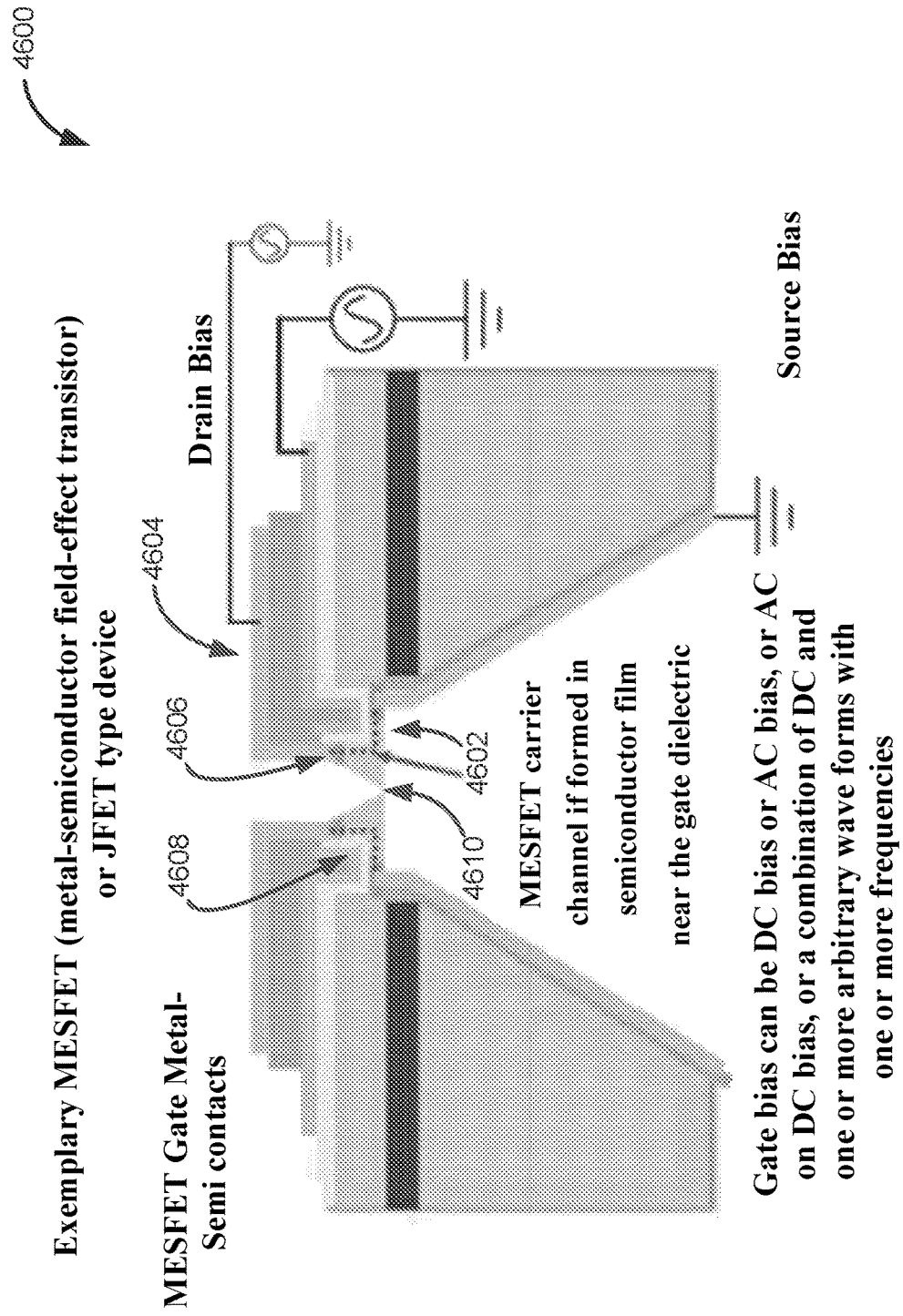
FIG. 46 illustrates another device (e.g., a MESFET) in accordance with additional exemplary embodiments of the disclosure.

FIG. 46 illustrates another device 4600 in accordance with exemplary embodiments of the disclosure. Device 4600 is similar to device 100, except device 4600 is a metal-semiconductor FET (MESFET). Alternatively, device 4600 could be a JFET device. Device 4600 includes a source region 4602, a drain region 4604, a channel 4606, and a gate structure 4608, wherein channel 4606 surrounds one or more nanopores 4610.

Exemplary Methods of Fabrication:

Turning now to FIGS. 4-28, a method of forming a device, such as device 100 is illustrated. The materials and dimensions in the figures are for exemplary purposes only and are not meant to restrict the scope of the patent.

Figure 4:
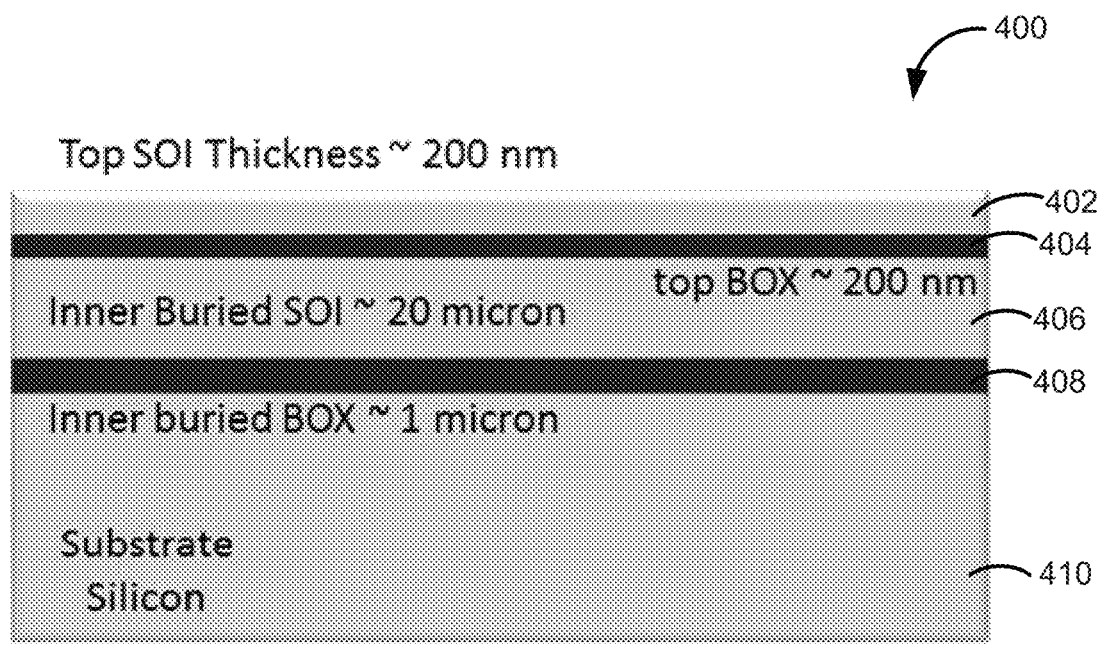
FIGS. 4-23, 25-26 illustrate steps of forming a device in accordance with exemplary embodiments of the disclosure.

FIG. 4 illustrates an exemplary substrate 400 suitable as starting material for use as substrate 102. Substrate 400 is a semiconductor on insulator substrate that includes a top semiconductor layer 402 (suitable for semiconductor layer 106), a first buried insulating layer 404, an inner buried semiconductor layer 406, a second buried insulating layer 408, and bulk material 410. A thickness of semiconductor layer 402 can range from about 10 nm to about 50 microns, about 50 nm to about 5 micron, or about 50 nm to about 1 micron. A thickness of first buried insulating layer 404 can range from about 1 nm to about 20 microns, about 10 nm to about 1 micron, or about 50 nm to about 500 nm. A thickness of inner buried semiconductor layer 406 can range from about 1 nm to about 200 micron, about 50 nm to about 50 micron, or about 5 micron to about 25 micron. A thickness of second buried insulating layer 408 can range from about 1 nm to about 20 microns, about 10 nm to about 1 micron, or about 50 nm to about 500 nm.

Figure 5:
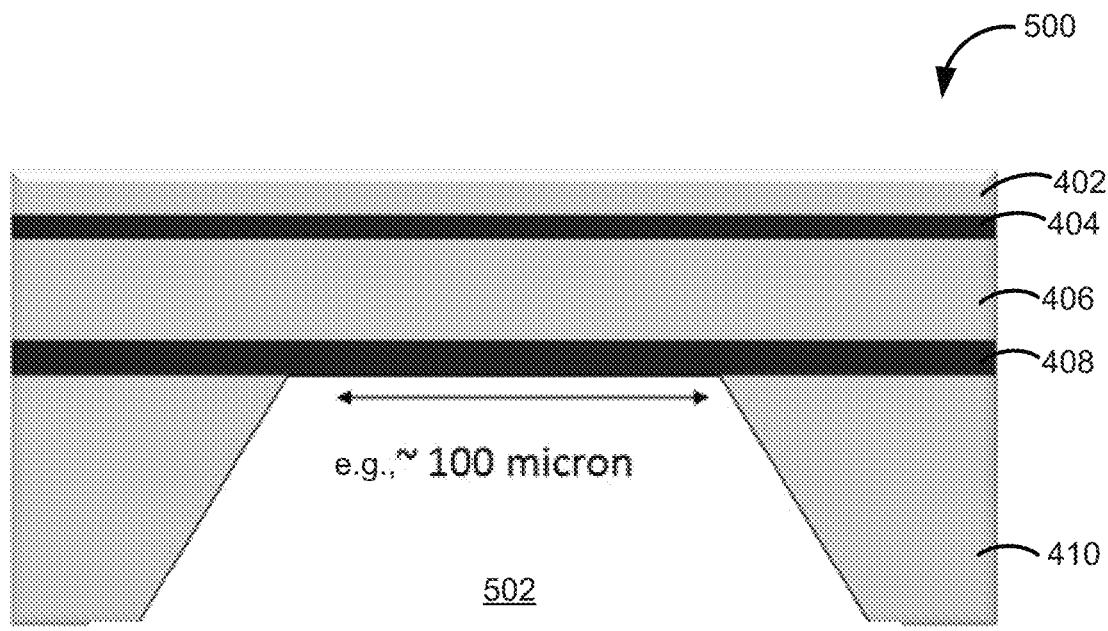

FIG. 5 illustrates a structure 500, including an etch region 502 formed within bulk material 410. Etch region 502 can be formed by, for example etching along a crystalline plane of the substrate using, for example, a wet chemical etch, such as tetramethylammonium hydroxide (TMAH) or KOH. Such etching may be self-limiting.

Figure 6:
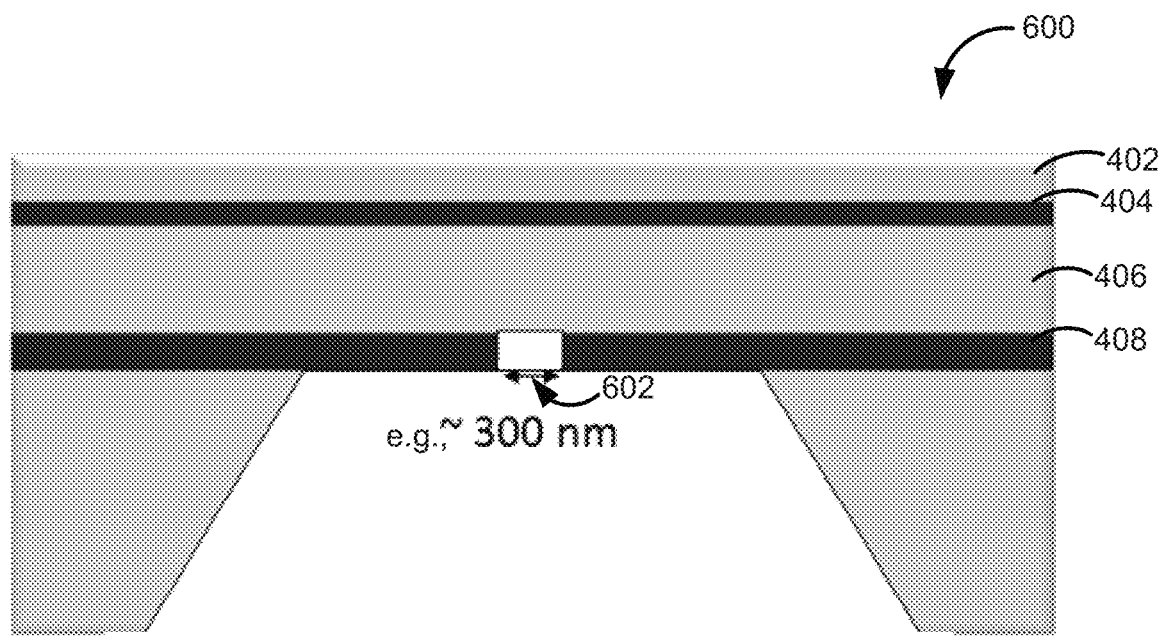

Next, structure 600, illustrated in FIG. 6, can be formed by forming an opening in second buried insulating layer 408. By way of example, opening 602 can be formed by spin coating PMMA or other suitable material and patterning the material using, for example, electron beam lithography (EBL). Once patterned, second buried insulating layer 408 can be etched using, for example reactive ion etching (RIE). Opening 602 can then be used as an etch mask.

Figure 7:
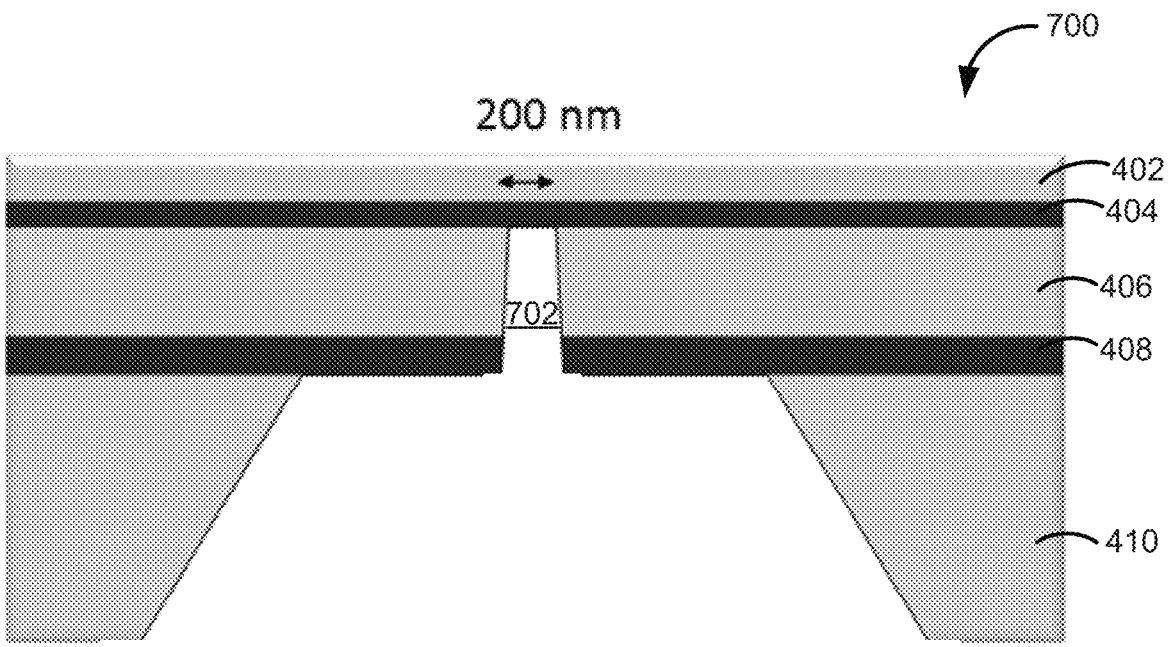

FIG. 7 illustrates structure 700, which includes via 702 formed within inner buried semiconductor layer 406. Via 702 can be formed by using opening 602 as an etch mask and using, for example, wet etching or a deep reactive ion etch (DRIE) process to form via 702 through inner buried semiconductor layer 406.

Figure 8:
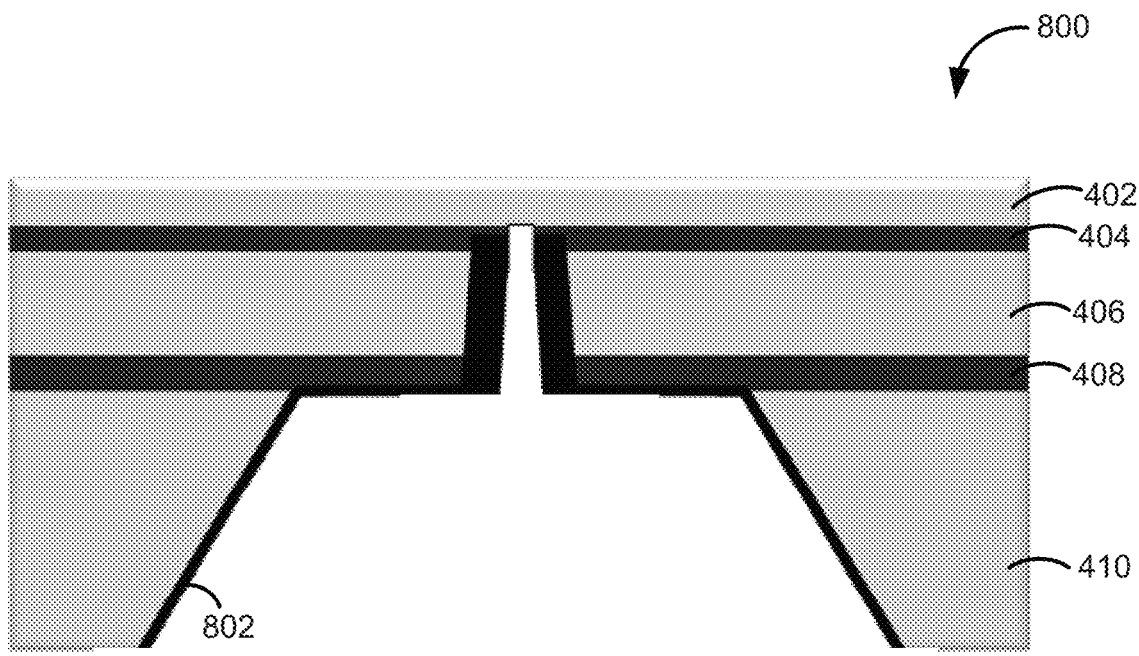

Next, a layer of insulating or dielectric material 802, such as silicon nitride can be deposited using, for example, low-pressure chemical vapor deposition to form structure 800, and a portion of 802 and first buried insulating layer 404 can be patterned using EBL (not shown) and etched, e.g., using reactive ion etching or wet etching, as illustrated in FIG. 8.

Figure 9:
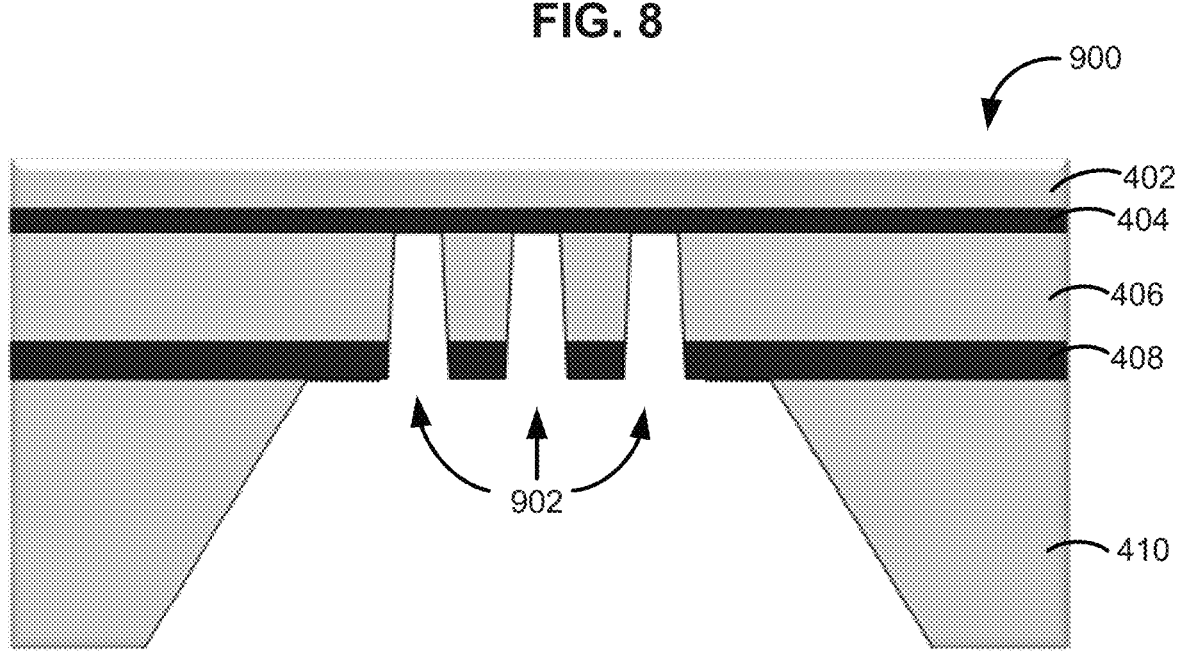

FIG. 9 illustrates an alternative example structure 900, in which a plurality of vias 902 is formed within second buried insulating layer 408 and inner buried semiconductor layer 406. Fabrication of devices using structure 900 can proceed in accordance with the description of FIGS. 4-8 and 10-28.

Figure 10:
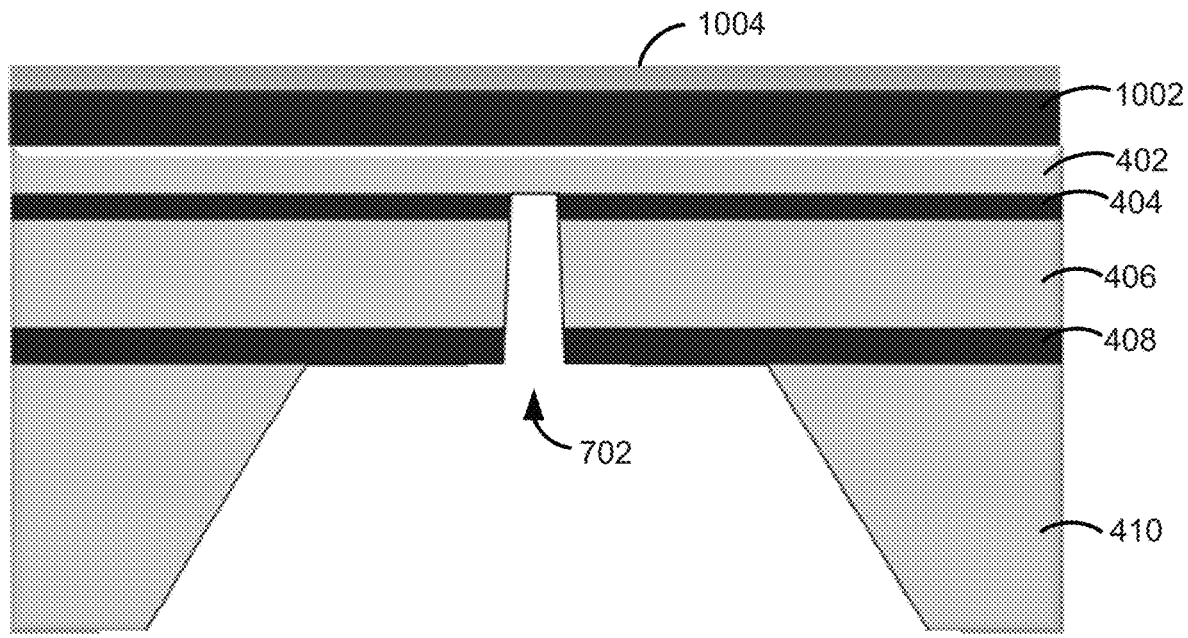
Figure 11:
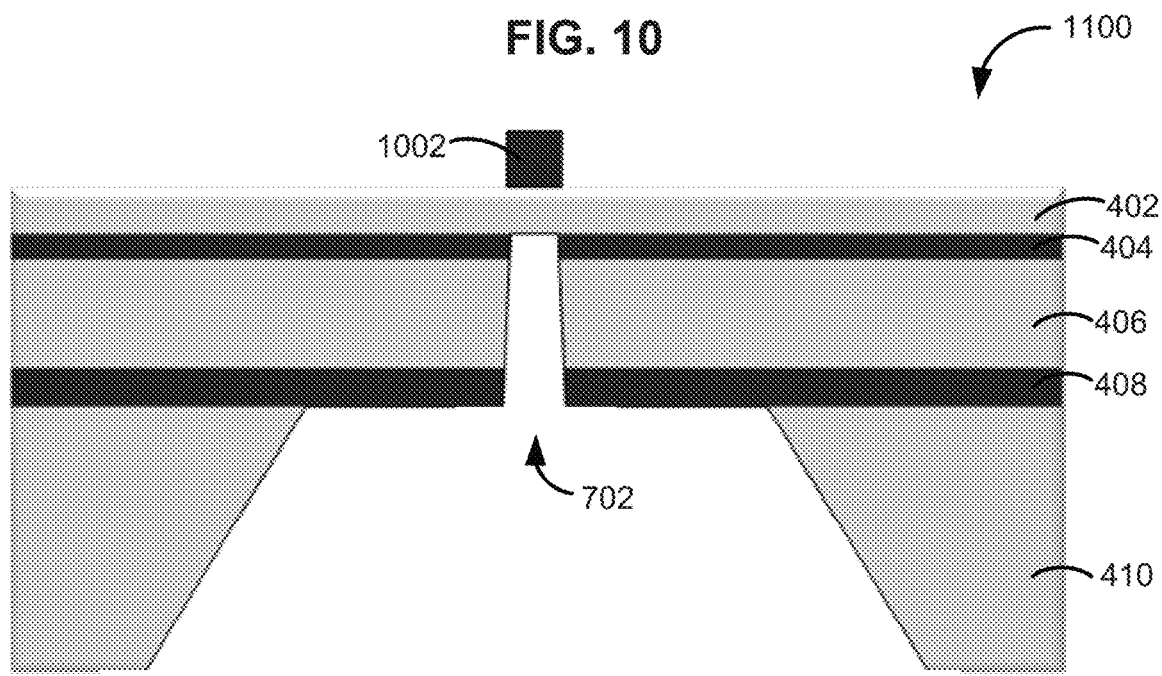

Next, an etch mask layer (e.g., an oxide) 1002, illustrated in FIG. 10, can be patterned using, for example, a negative photoresist layer or a infra-red sensitive layer 1004 to form structure 1100, where 1004 can be patterned using photolithography such as but not limited to UV, infra-red light or using ion-beams or electron beams—that are incident from the bottom side to pattern the layer 1004 on the top side using 702 as mask, which includes a structure 1102 that is aligned with via 702, as illustrated in FIG. 11.

Figure 12:
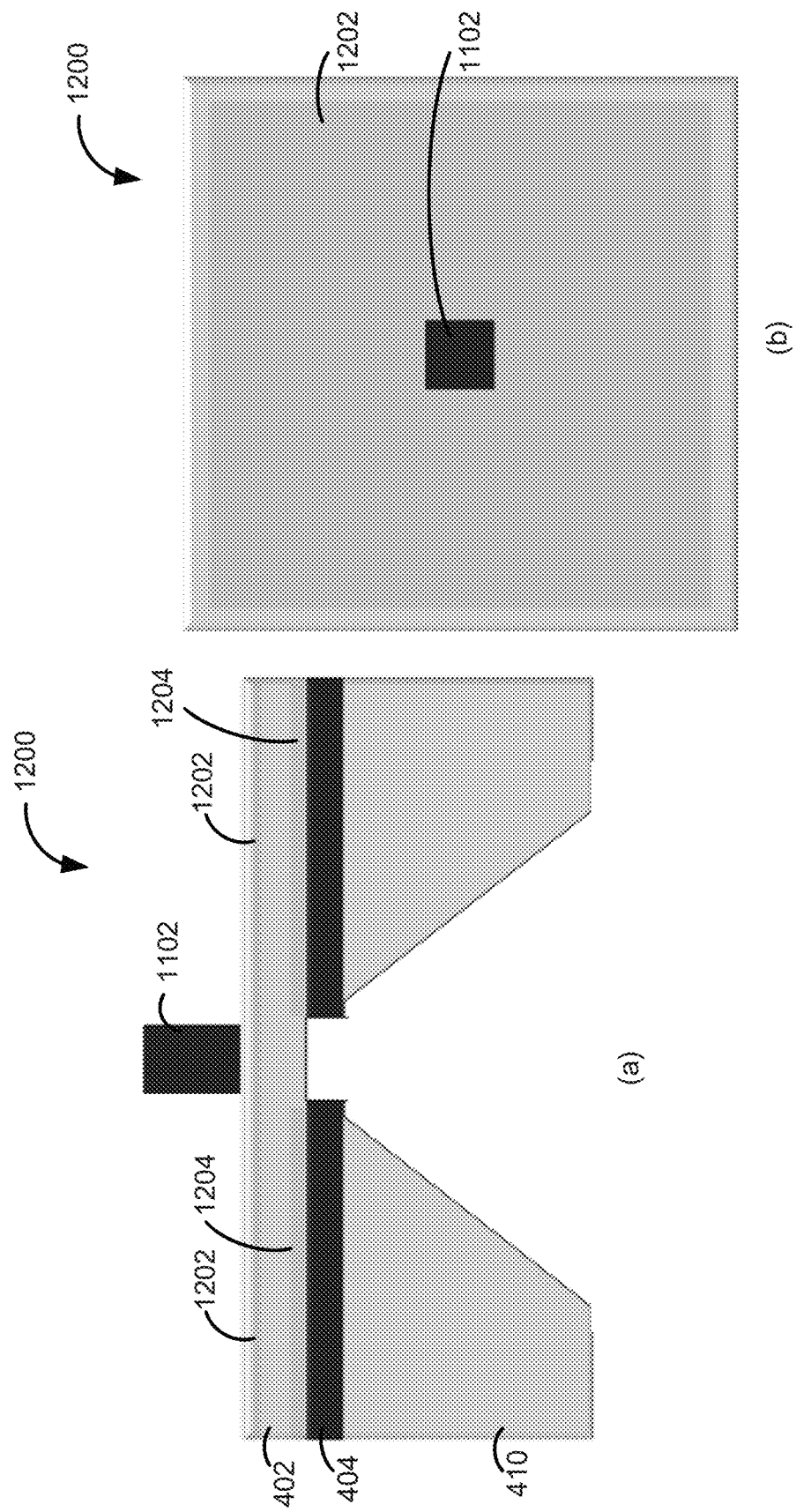

FIG. 12 illustrates a structure 1200 that is formed by forming doping regions 1202 (e.g., source) and 1204 (e.g., drain). In FIG. 12, (a) illustrates a cross-sectional view of structure 1200 and (b) illustrates a top view of structure 1200. Some of the layers of structure 1200 and subsequent structures are omitted from the figures for illustration purposes. For example, layers 406 and 408 may not be illustrated in some of the figures for clarity.

Figure 13:
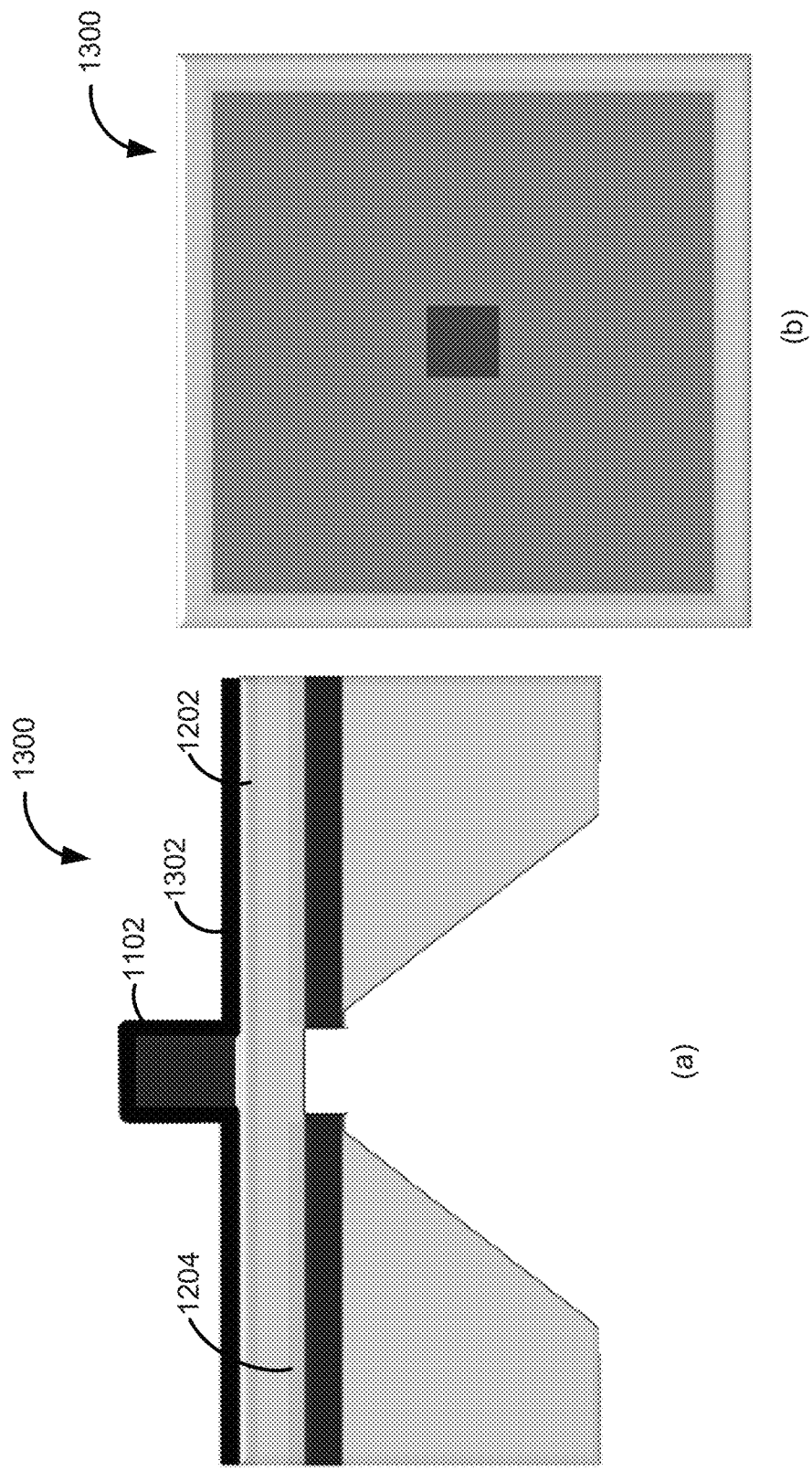

Next, spacers can be formed about structure 1102 by depositing a layer (e.g., nitride) 1302 overlying the top of structure 1200 to form a structure 1300. In FIG. 13, (a) illustrates a cross-sectional view of structure 1300 and (b) illustrates a top view of structure 1300.

Figure 14:
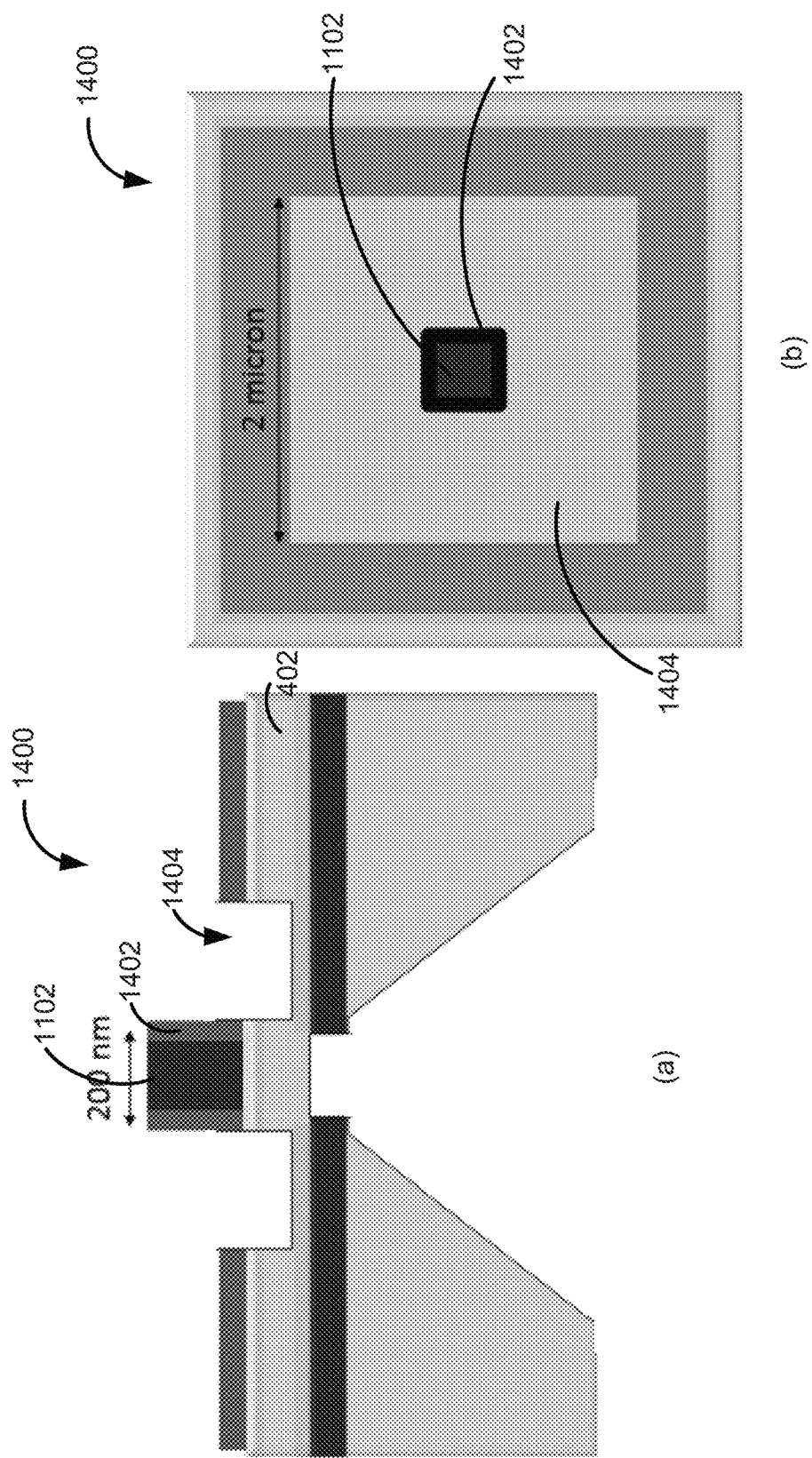

FIG. 14 illustrates a structure 1400, which includes a spacer 1402 formed about structure 1102 by etching 1302 using reactive ion etching. Lithography is used to pattern an etch moat about spacer 1402, using 1402 as mask, to etch a portion of layer 402 to form moat region 1404. In FIG. 14, (a) illustrates a cross-sectional view of structure 1400 and (b) illustrates a top view of structure 1400.

Figure 15:
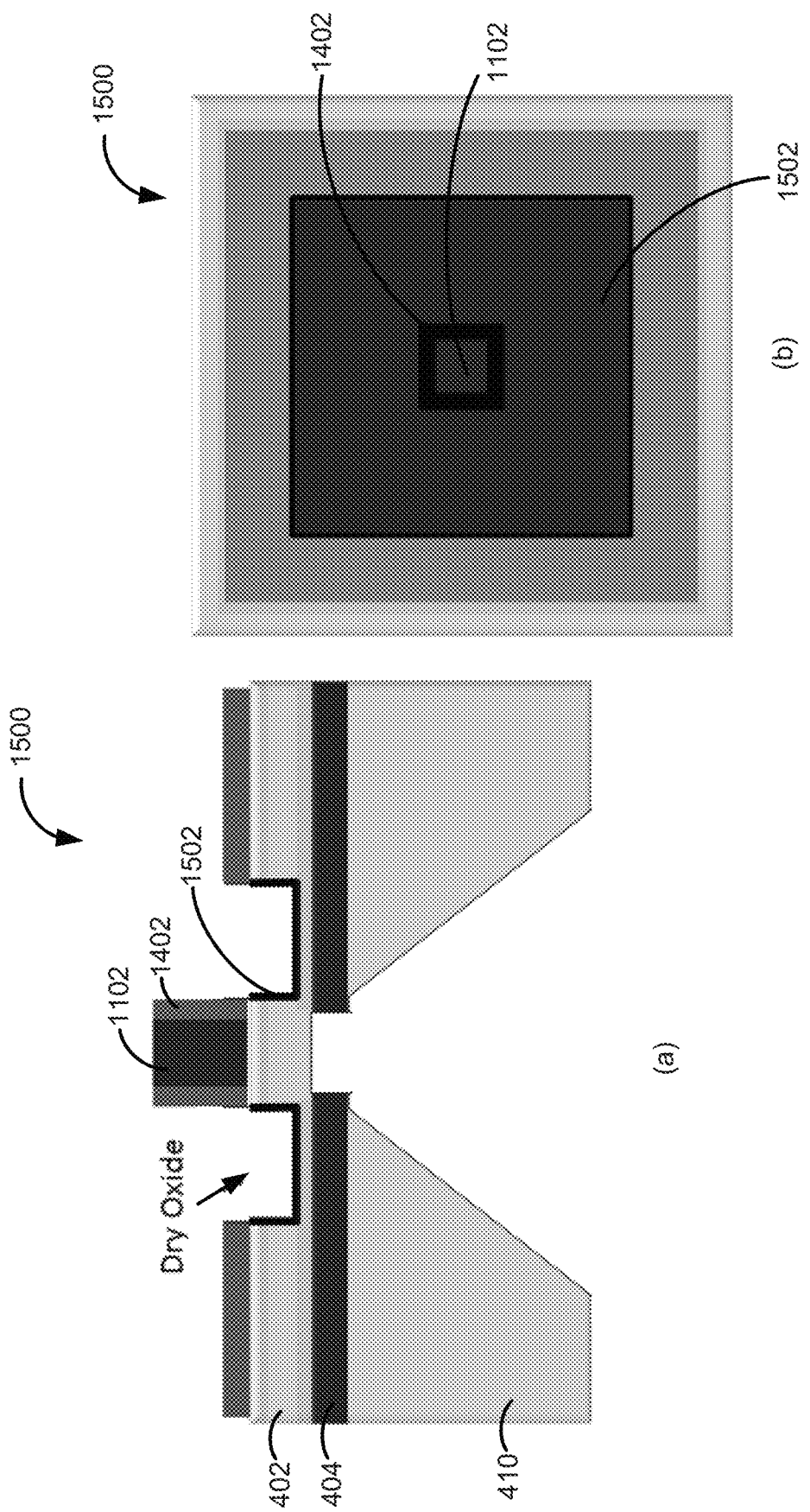

FIG. 15 illustrates a structure 1500 that includes a gate dielectric material 1502 grown or deposited within moat region 1404. Gate dielectric material can include for example silicon oxide or silicon nitride or hafnium oxide and can be grown by dry or wet oxidation or deposited using LPCVD, PECND or ALD deposition processes. In FIG. 15, (a) illustrates a cross-sectional view of structure 1500 and (b) illustrates a top view of structure 1500.

Figure 16:
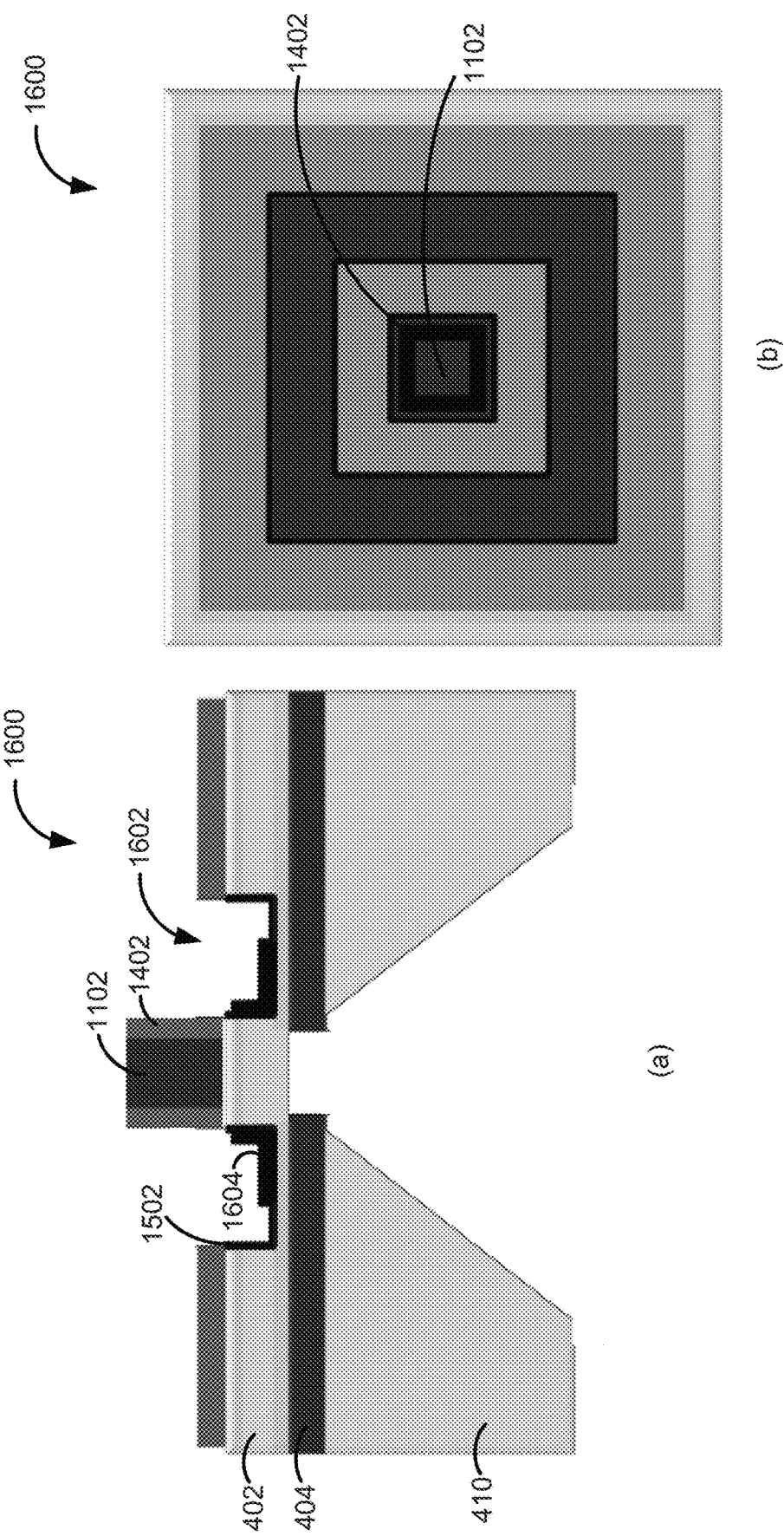

FIG. 16 illustrates (a) a cross-sectional view and (b) a top view of a structure 1600, which includes a gate structure 1602, including a gate oxide material 1502 and a gate metal 1604. Gate metal 1604 can include, for example, TiSi/NiSi/

CoSi, Al, Pd and can be deposited using any suitable deposition and optionally etch processes.

Figure 17:
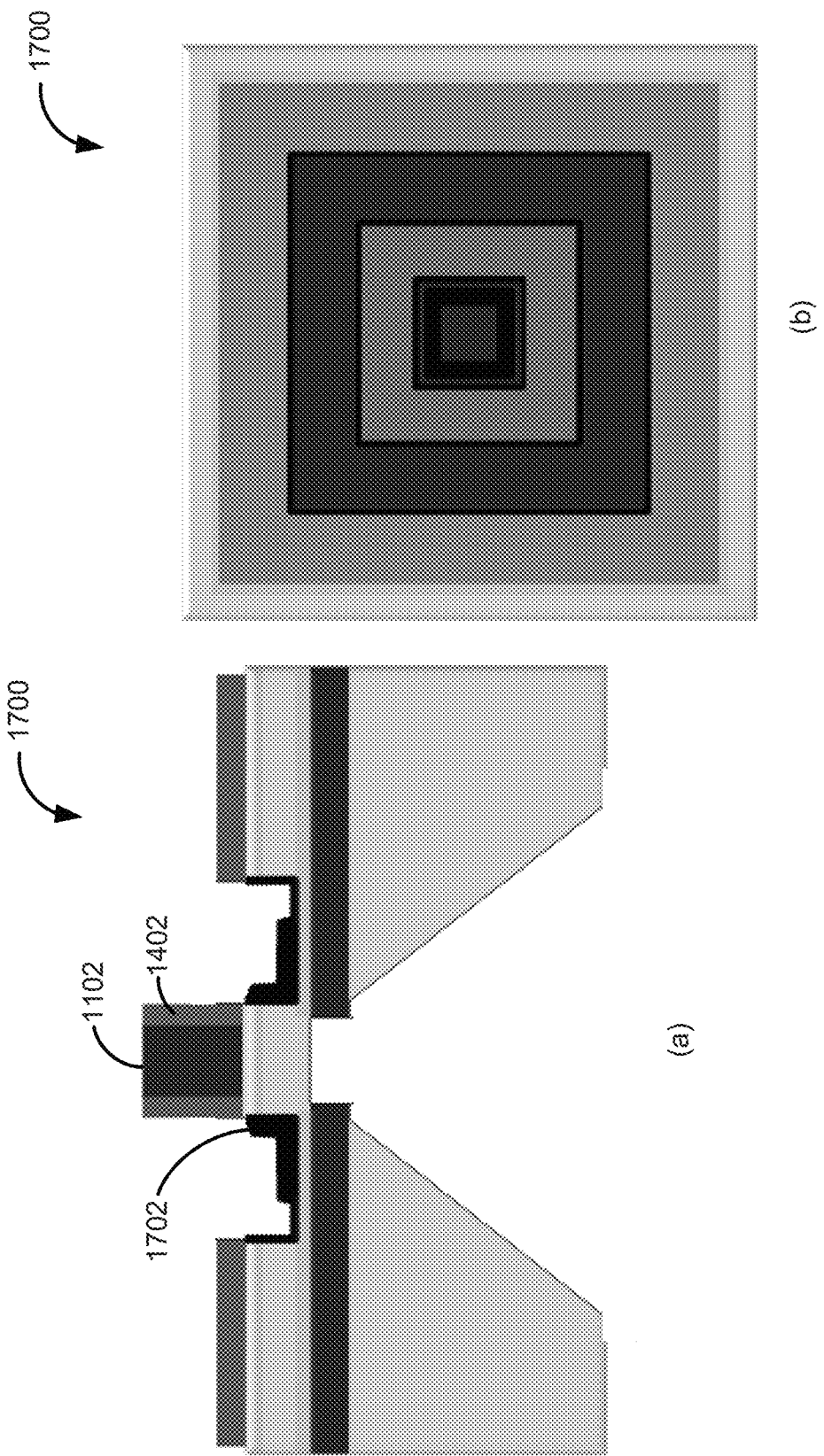

Next, an encapsulation layer 1702 for gate structure 1602 can be formed, as illustrated in FIG. 17, in which (a) illustrates a cross-sectional view and (b) illustrates a top view of a structure 1700 including encapsulation layer 1702. Encapsulation layer 1702 can be formed using, for example a dry oxidation process.

Figure 18:
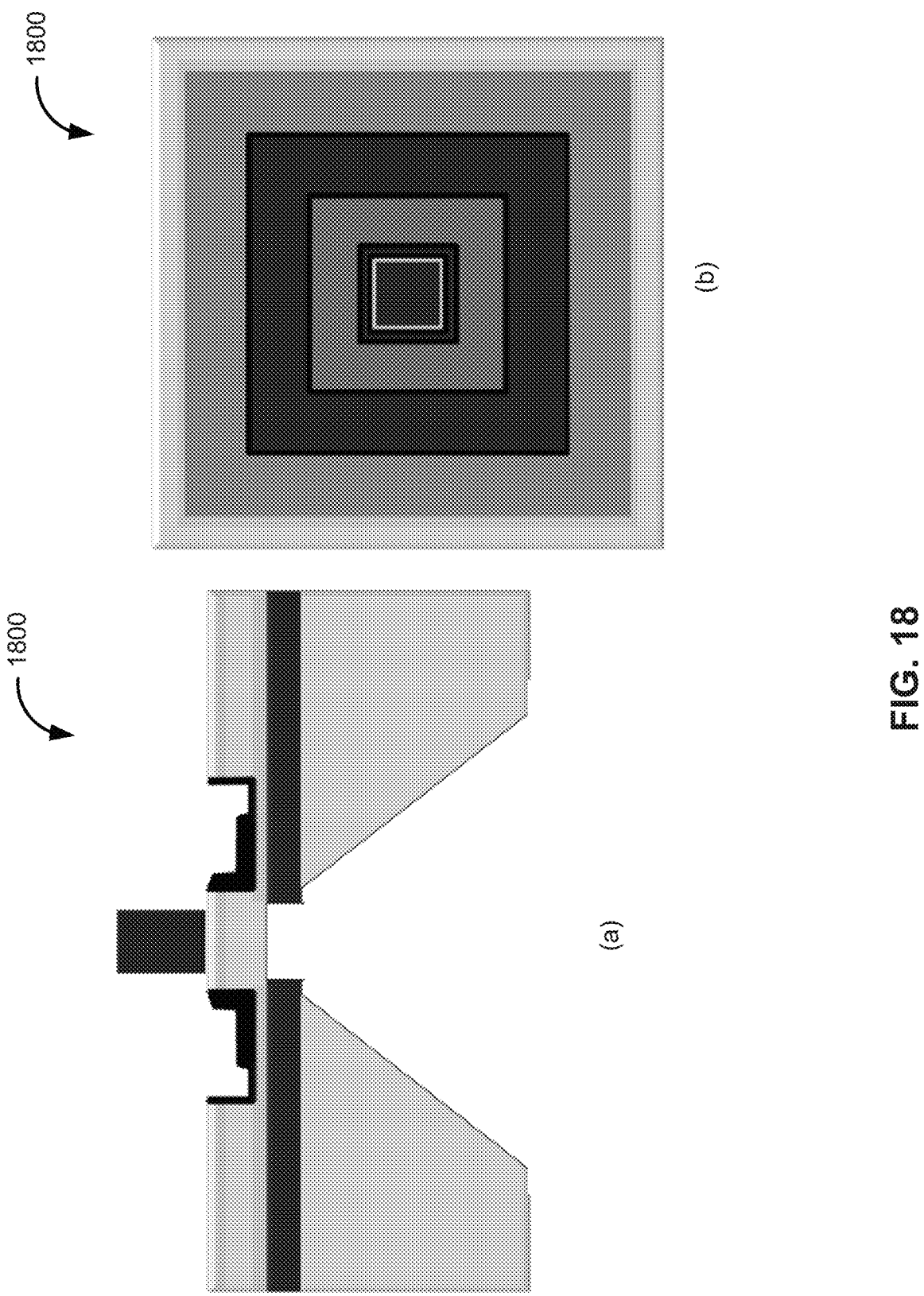

In FIG. 18, in which (a) illustrates a cross-sectional view and (b) illustrates a top view of a structure 1800, the remaining portions of layer 1302 can be removed using, for example, phosphoric acid etch or reactive ion etching to form structure 1800.

Figure 19:
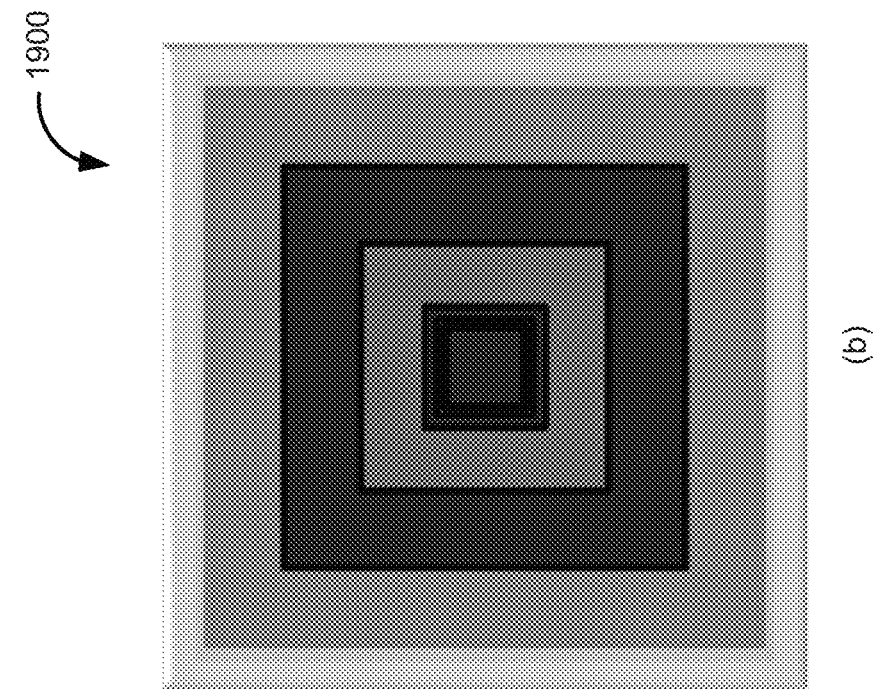
Figure 19:
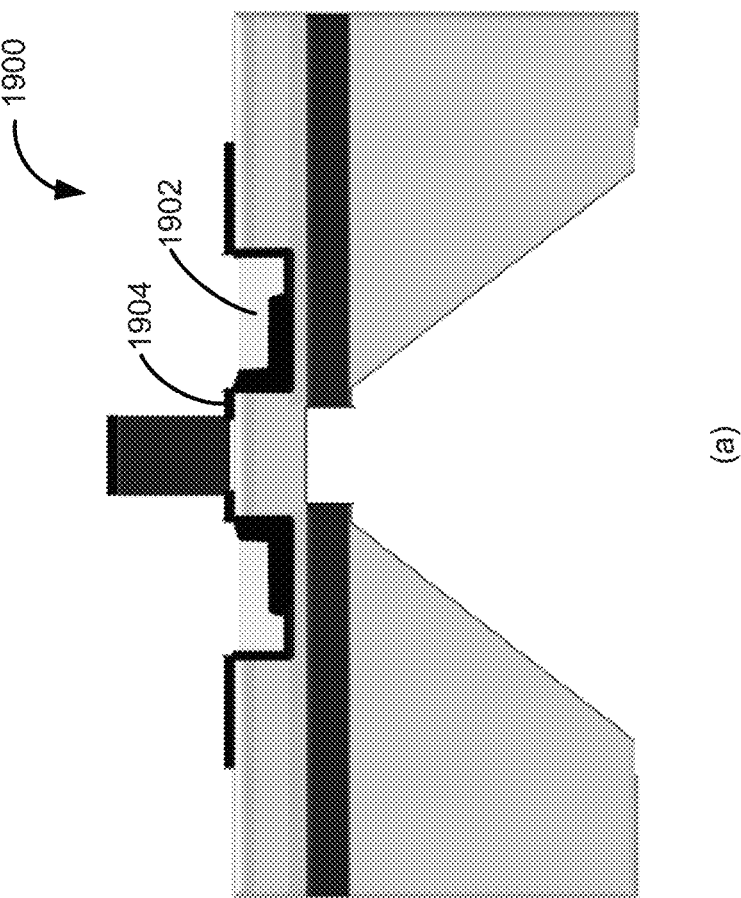

Structure 1800 can be patterned using resist fill 1902 and lithography patterning (not shown) and source metal contacts 1904 can be formed, as illustrated in FIG. 19, in which (a) illustrates a cross-sectional view and (b) illustrates a top view of a structure 1900. Source metal contacts can be formed using any suitable process, such as lift off of metal deposited using e-beam, thermal, ALD deposition.

Figure 20:
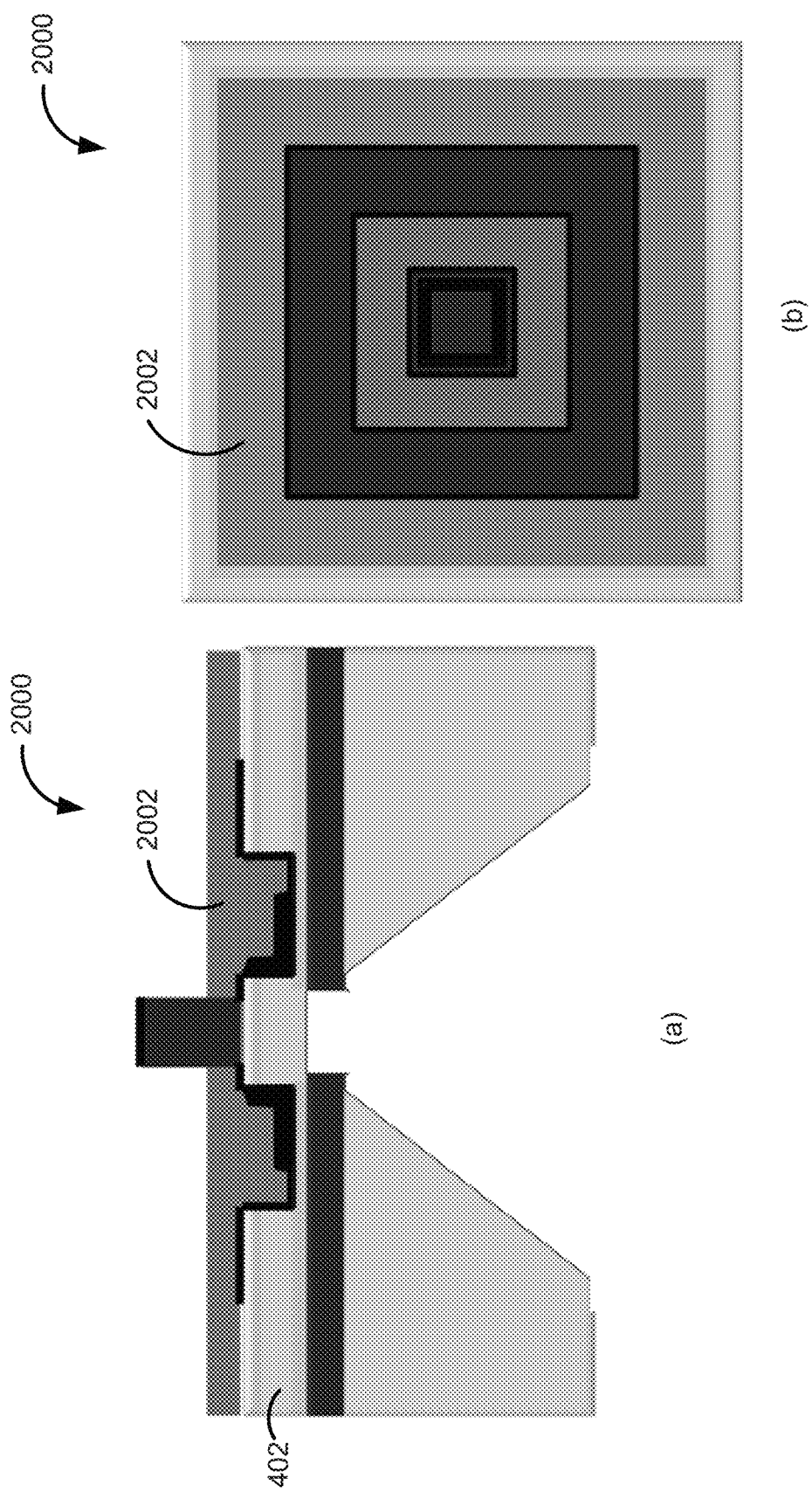

Next, an isolation layer 2002 (e.g., LPCVD silicon nitride) can be deposited to form structure 2000, illustrated in FIG. 20, in which (a) illustrates a cross-sectional view and (b) illustrates a top view of a structure 2000.

Figure 21:
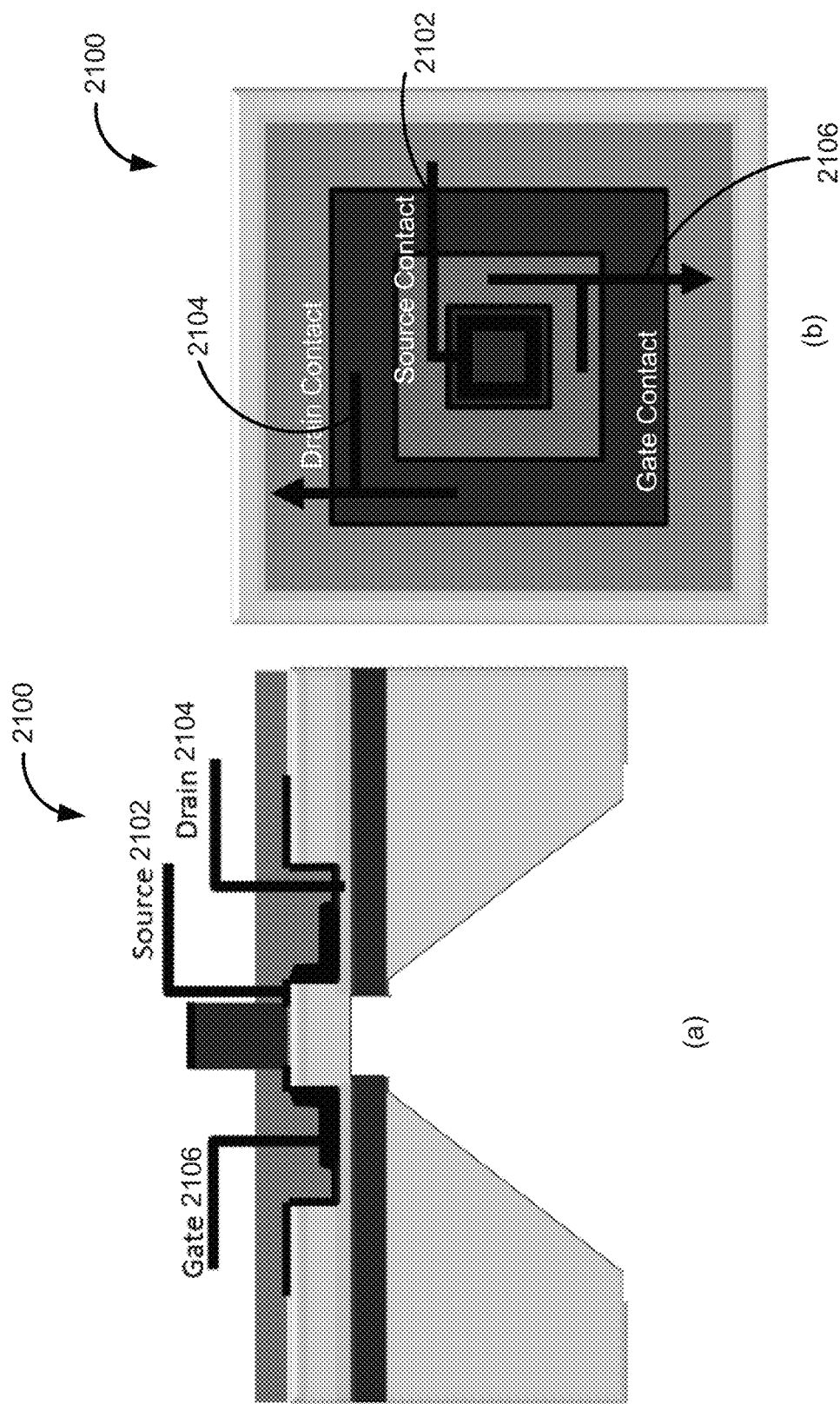

Next, contacts 2102, 2104, and 2106 to, respectively, the source, drain, and gate regions can be formed, as illustrated in FIG. 21, in which (a) illustrates a cross-sectional view and (b) illustrates a top view of a structure 2100.

Figure 22:
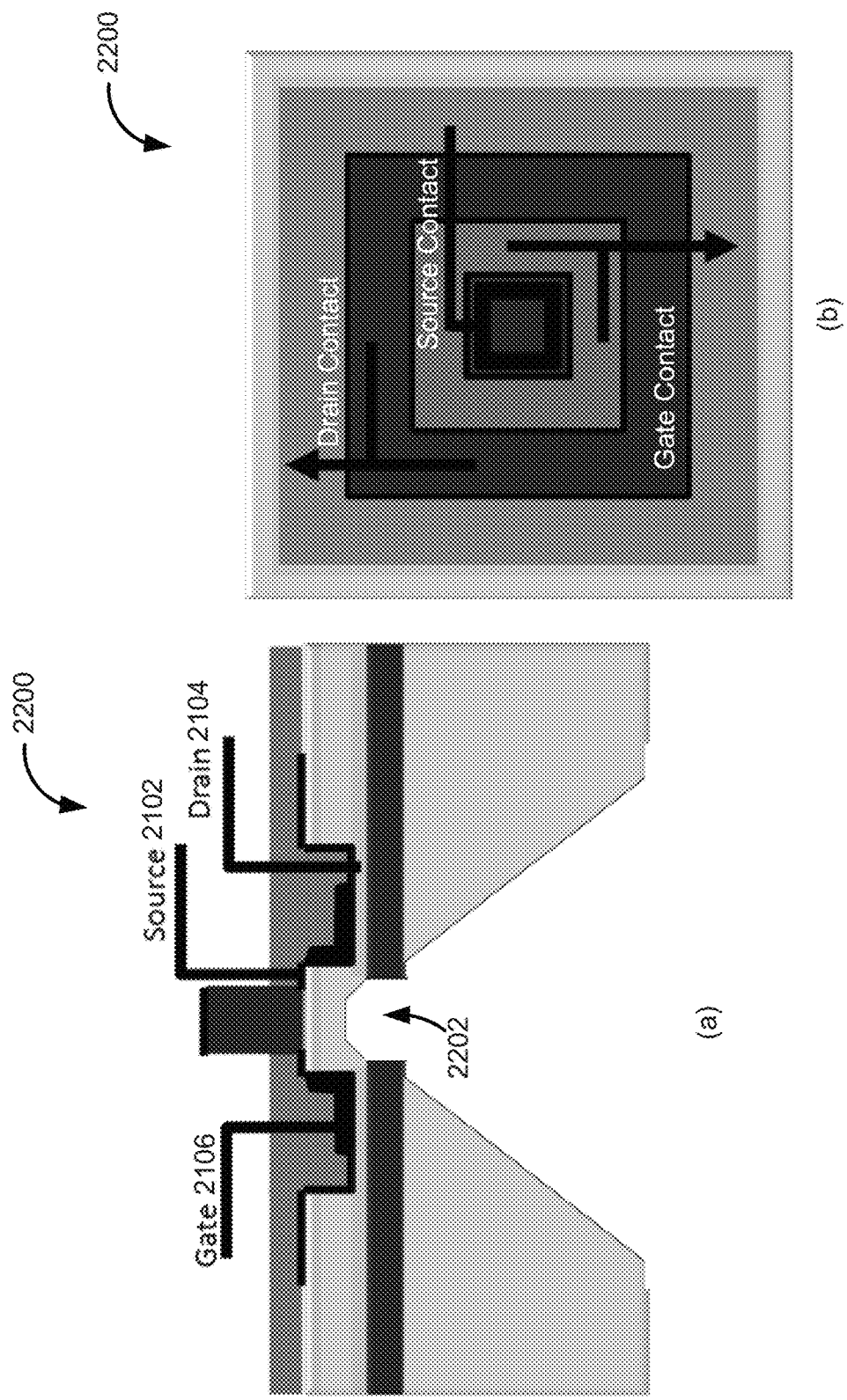
Figure 23:
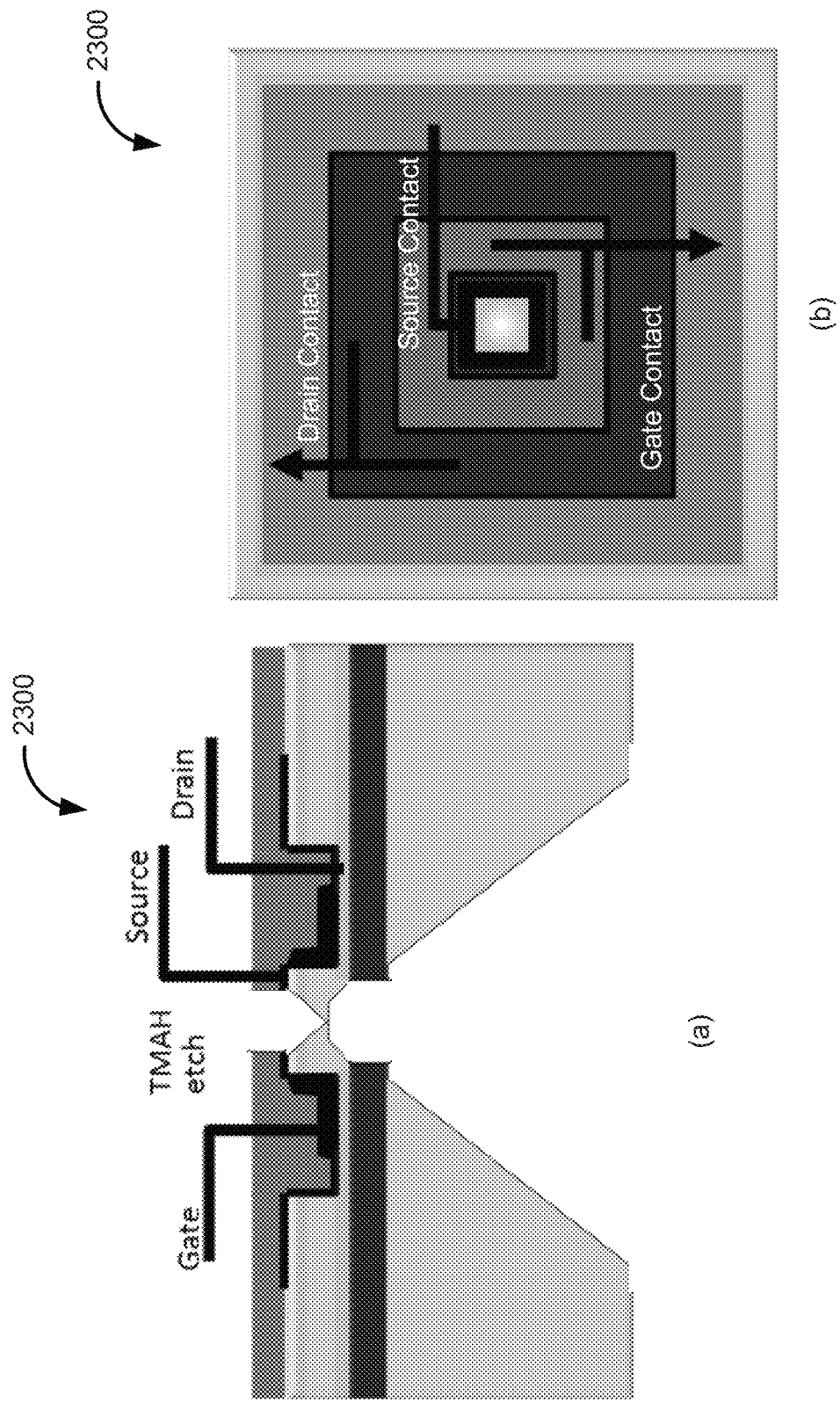

FIGS. 22 and 23 illustrate nanopore formation in accordance with exemplary embodiments of the disclosure, in which (a) illustrates a cross-sectional view and (b) illustrates a top view of a structures 2200 and 2300.

Structure 2200 includes an etch region 2202 that can be formed using a wet etch process, such as a time-controlled Tetramethylammonium hydroxide (TMAH) etch. Structure 2300 can similarly be formed by removing structure 1102 and etch a portion of semiconductor layer from the opposite side using electric feedback and/or chemical-stop etching and/or physical block formation etching to form structure 2200. FIGS. 22 and 23 illustrate structures that include a frusto-conical or frusto-pyramidal etch portion (bottom portion) and a conical or pyramidal etch portion (top portion).

Figure 41:
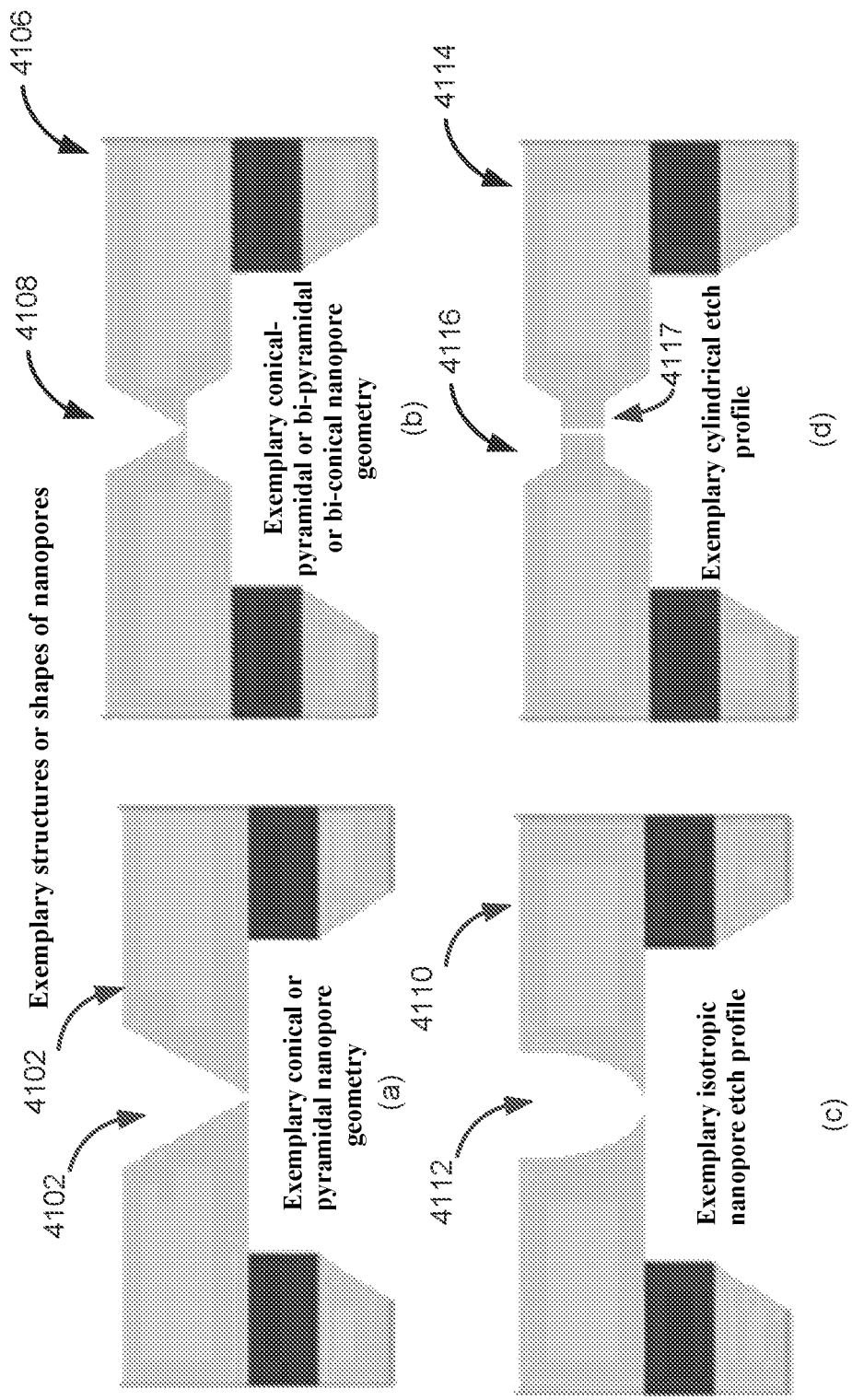
FIG. 41 illustrates exemplary configurations of etch sections in accordance with exemplary embodiments of the disclosure.

FIG. 41 illustrates additional structures, wherein (a) illustrates a structure 4102 that includes a conical or pyramidal etch section 4104, (b) illustrates a structure 4106 that includes a conical or pyramidal etch section 4109 and a frusto-conical or frusto-pyramidal etch section 4109, (c) illustrates a structure 4110 that includes an isotropic etch section 4112, and (d) illustrates a structure 4114 that includes a frusto-conical or frusto-pyramidal etch section 4116 and a frusto-conical or frusto-pyramidal or cylindrical etch section 4117.

Control of nanopore size during nanopore formation can be important for a variety of reasons. In accordance with various aspect of these embodiments, a nanopore size can be controlled by performing one or more of the following during the etch process: 1) electric current feedback monitoring (2) capacitance measurement monitoring (3) chemical-stop etching, wherein etchant-chemical mixes with another chemical, such as a buffer or an acidic solution, upon nanopore formation and loses etching activity and (4) formation of a material-aggregate such as salt or polymer when etching-chemical mixes with another chemical upon nanopore formation, wherein the material-aggregate physically stops further nanopore formation. In accordance with some examples of the disclosure, etching is stopped before the formation of the one or more nanopores based on a measurement of one or more of: electrical current measurement, capacitive measurement, and capacitive measurement, resistance measurement, conductance measurement, or by monitoring transmission and/or absorption and/or reflection of light, ion beam, UV light, infra-red light, electron beam in the residual film.

Below are some example methods of forming nanopores in accordance with the disclosure.

Chemical-Stop Nanopore Etching for Controlled Nanopore Diameter (100 nm to 1 nm) and/or for Stopping Etching Before Pore Formation Fabrication of nanopores in silicon by chemical etching using KOH and buffer solution with electrical feedback has been demonstrated to yield nanopores of controlled diameter. This process is based on the chemical-stop etching. Such techniques generally yield either pyramidal holes or circular-conical holes. The principle idea is to stop base-etching of the silicon nanopore at the nanopore-location, once nanopore etch-through has occurred, by way of using an acidic buffer solution (or weak acidic solutions) at the other end of the silicon film. When base-etchant (e.g., tetramethylammonium hydroxide (TMAH) or KOH) etches through the thin silicon membrane, forming a sub-10 nm nanopore, $OH^-$ radicals from base etchant instantly meet $H^+$ radicals from acidic buffer solutions on other side, forming water molecules and salt. Consumption of $OH^-$ radicals at the nanopore interface leads to instantaneous stopping of any further etching of nanopore. FIG. 47 illustrates a nanopore formed using this technique, which illustrates physical etch block formation which is salt formation blocking the nanopore to prevent or mitigate further etching of the nanopore. Using a feedback electrical sense circuit to measure conduction across the nanopore due to base-acid neutralization, any further etching of nanopore is stopped. This two-step and/or three etch-stop process: chemical etch-stop combined with electrical feedback etch-stop, and/or combined with physical salt/polymer/aggregate block formation is expected to yield much higher control of nanopore fabrication. This chemical-stop etch process can be used for fast, precise fabrication of controlled nanopores in many different kinds of substrate materials. Neutralization reaction at the nanopore is an exothermic process. Hence weak acidic buffer solutions (~pH from 2 to 6) are used, where acidic buffer pH value, its buffer capacity and TMAH concentration may be process variables.

Capacitance and Resistance Based Measurements for Residual Silicon Thickness

Using CV measurements in addition to resistance/conductance measurement can be used to monitor the residual thickness of silicon film while it is being etched. With decreasing silicon thickness, as it is etched, the capacitance of silicon at the nanopore location is expected to vary (increase), which can be measured and correlated, to stop etching at nanopore formation or prior to nanopore formation Another Method for Nanopore Fabrication Backside of the substrate can be coated with a metal or semiconducting conducting layer thin film, and the conductivity (or capacitance) between the solution on etching side and this back conducting film is monitored with time. When a nanopore is formed on the substrate, the etching fluid comes into contact with back metal or conductive film, which causes a large change in conductivity or capacitance or impedance. By measuring conductivity (or capacitance or impedance) at high frequency voltage bias, and stopping the etch reaction when the conductivity changes, very accurate nanopores (e.g., having defined features such an a size of an opening) can be formed. Alternately this method can be used to stop etching right before nanopore formation, wherein nanopore opening can be done later on or at the end of device fabrication.

Alternate Methods for Nanopore Fabrication

Alternatively, nanopores can be fabricated using methods and instruments such as electron beam milling, FIB (focused ion beam), ion beam sculpting, or other suitable technique.

Additionally, a nanopore (or a micro pore) once formed might be narrowed or shrunk down (i.e., its diameter at the opening reduced) further by growing an additional layer such as thermal silicon dioxide. Or, a nanopore can be shrunk/narrowed using electron beam techniques or ion beam/laser based or other local thermal heating based methods. Alternately nanopore diameter can be shrunk-down by depositing thin films using ALD, LPCVD, PECVD, e-beam deposition methods.

Methods of making nanopores, both solid state and biological nanopores, methods of under-etching or undercutting or scallop-etching using isotropic reactive ion etching or wet etching to form C-shaped or V-shaped gate, are listed in the following publications, which are included herein by their reference in their entirety, to the extent their contents do not conflict with the present disclosure.

Takulapalli, B. R. Molecular Sensing Using Monolayer Floating Gate, Fully Depleted SOI MOSFET Acting as an Exponential Transducer. Acs Nano 4, 999-1011 (2010).

53. Takulapalli, B. R. et al. Electrical detection of amine ligation to a metalloporphyrin via a hybrid SOI-MOSFET. Journal of the American Chemical Society 130, 2226-2233 (2008).

Nanopore sensors for nucleic acid analysis, Bala Murali Venkatesan & Rashid Bashir Nature Nanotechnology, 6, 615-624 (2011), doi: 10.1038/nnano.2011.129.

Disease Detection and Management via Single Nanopore-Based Sensors Reiner, Joseph E.; Balijepalli, Arvind; Robertson, Joseph W F.; et al. CHEMICAL REVIEWS Volume: 112 Issue: 12 Pages: 6431-6451 DOI: 10.1021/cr300381m December 2012.

Single molecule sensing with solid-state nanopores: novel materials, methods, and applications Miles, B N (Miles, Benjamin N) [1]; Ivanov, A P (Ivanov, Aleksandar P.) [1] et al. CHEMICAL SOCIETY REVIEWS Volume: 42 Issue: 1 Pages: 15-28 DOI: 10.1039/c2cs35286a 2013.

Electron-beam-induced deformations of SiO2 nanostructures Storm, A J (Storm, A J); Chen, J H (Chen, J H); Ling, X S (Ling, X S); Zandbergen, H W (Zandbergen, H W); Dekker, C (Dekker, C)

JOURNAL OF APPLIED PHYSICS Volume: 98 Issue: DOI: 10.1063/1.1947391 Jul. 1 2005.

Super-selective cryogenic etching for sub-10 nm features, Zuwei Liu et al, Nanotechnology, Volume 24, Number 1

Additional techniques for forming nanopores are described in PCT Application No. PCT/US13/35852, entitled FIELD EFFECT TRANSISTOR, DEVICE INCLUDING THE TRANSISTOR, AND METHODS OF FORMING AND USING SAME, filed Apr. 9, 2013, the contents of which are hereby incorporated herein by reference, to the extent such contents do not conflict with the present disclosure.

Figure 42:
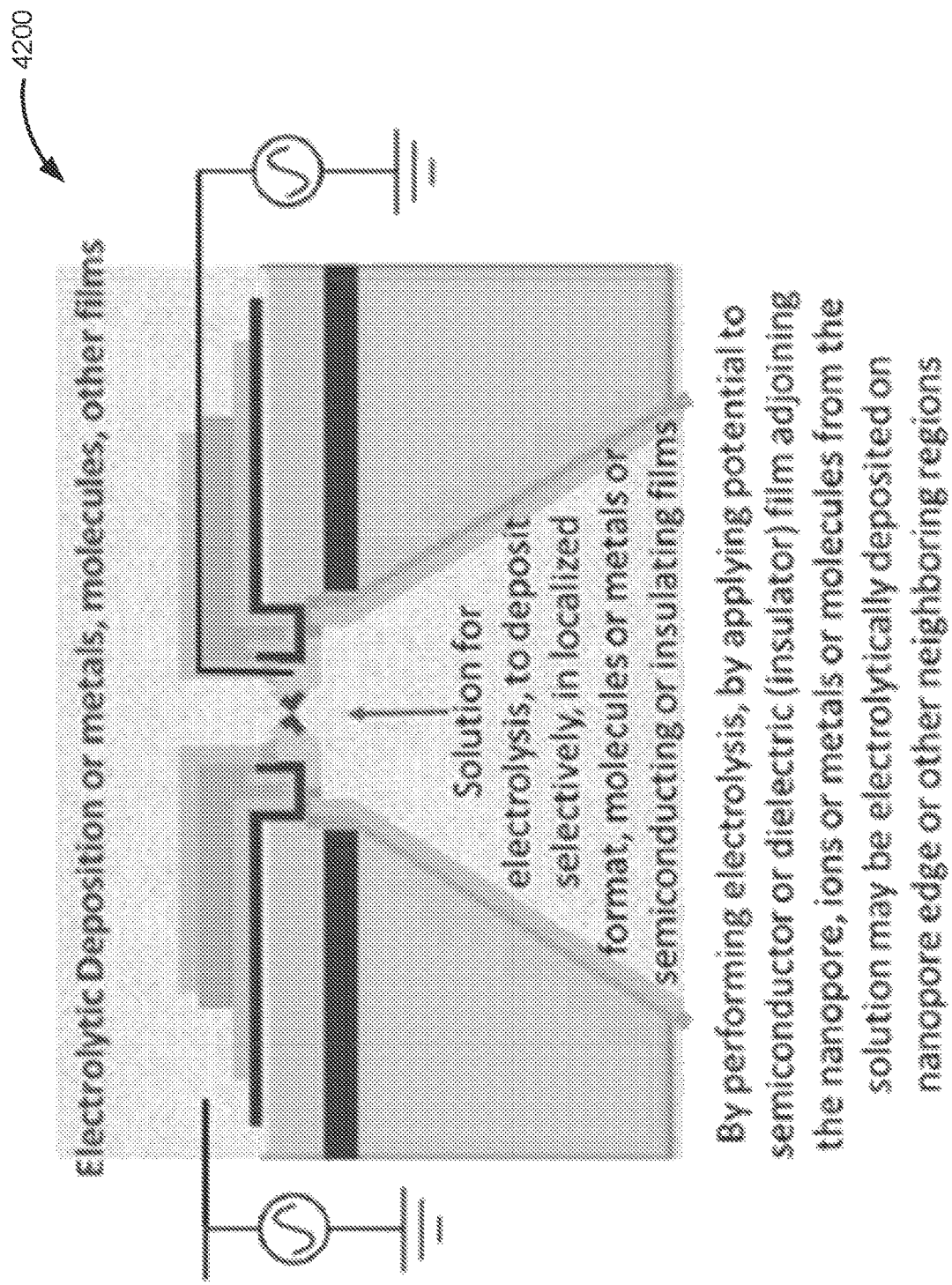
FIG. 42 illustrates a electrolytic based technique for selectively depositing material onto a nanopore or other portion of a device in accordance with exemplary embodiments of the disclosure.

The methods described herein may also include forming at least one lipid bilayer overlaying a nanopore and/or adding a biological and/or chemical substance or other layer as described herein to the structure to form a biological and/or chemical nanopore. FIG. 42 illustrates a technique for depositing material onto a surface of a nanopore. In the illustrated example, a structure 4200 or portion thereof can be placed in solution, a bias can be applied across a portion of the structure, and material can be selectively deposited onto a portion of the structure. One example method of deposition is electrolytic detection. In this case, material in solution can be selectively deposited onto a portion of structure 4200.

Figure 43:
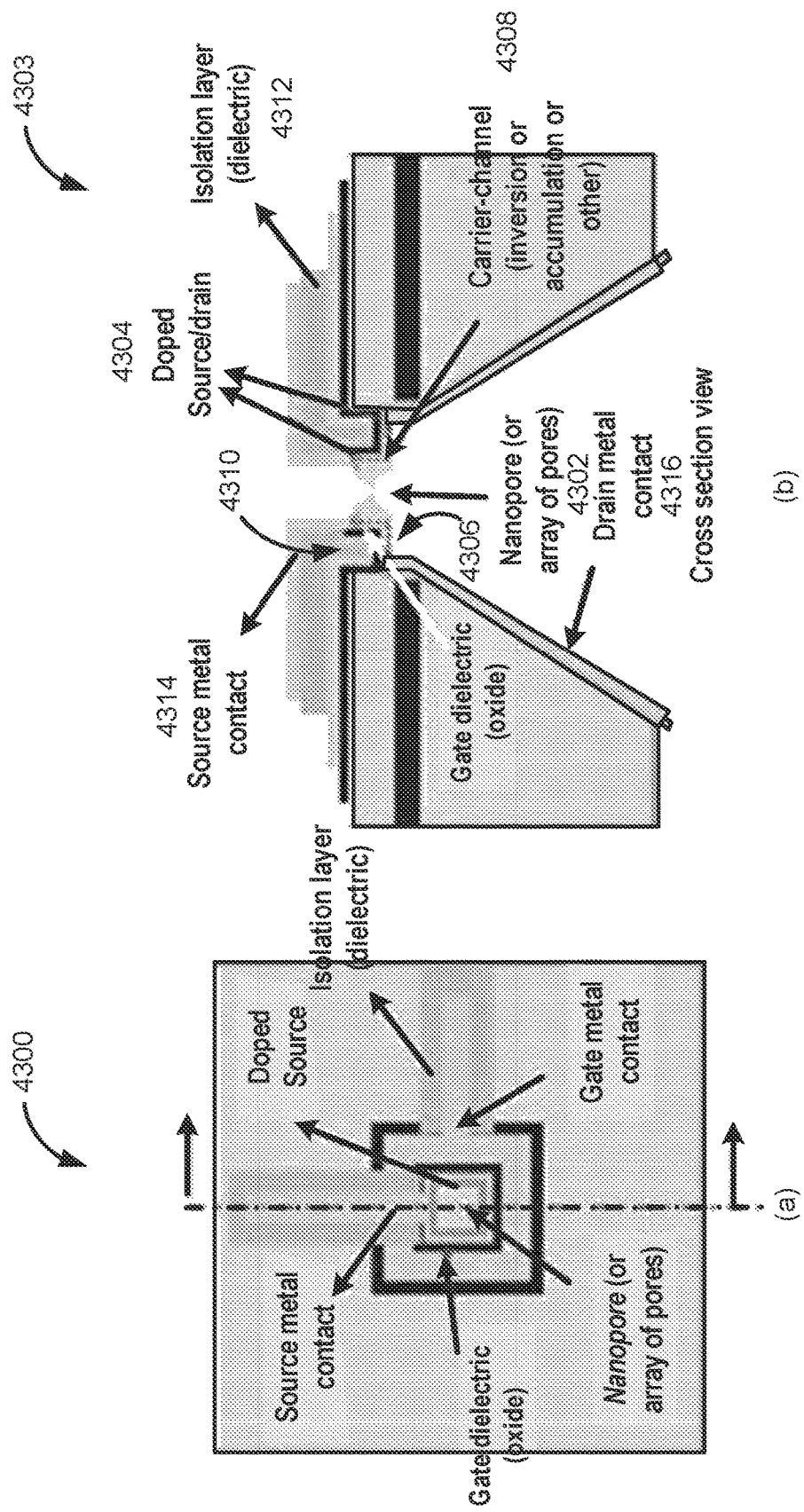
FIG. 43 illustrates (a) a top view and (b) a cross-sectional view another device in accordance with exemplary embodiments of the disclosure.

With reference to FIG. 43, another device 4300, which includes an isolation layer and contacts formed on two surface of a substrate is illustrated. Device 4300 includes one or more nanopores 4302, a source region 4304, a drain region 4306, a channel 4308, a gate region 4310, and an isolation layer 4312. Device 4300 also includes source contact 4314, and drain metal contact on an opposite side of the device.

Figure 24:
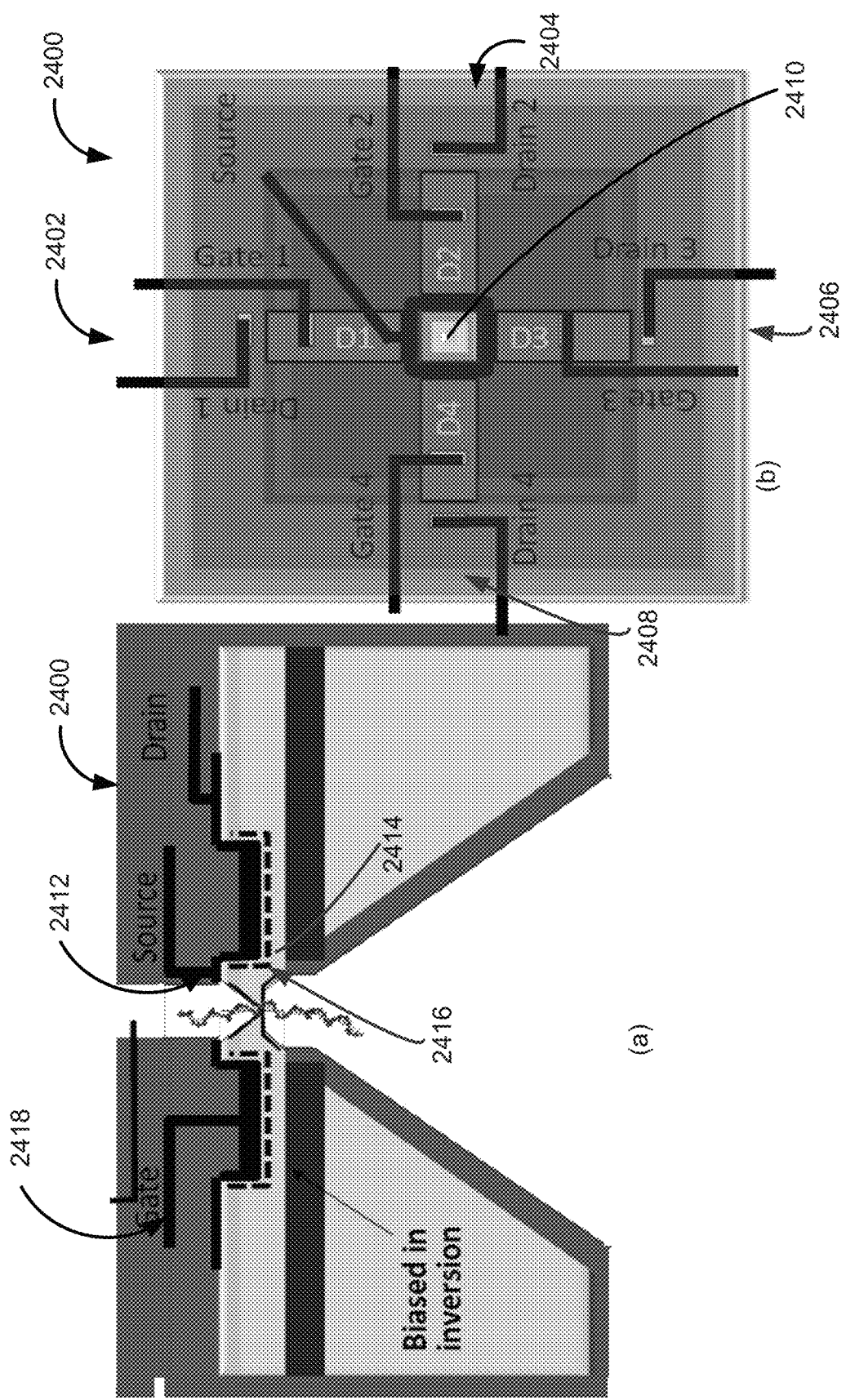
FIG. 24 illustrates a sensor device in accordance with additional exemplary embodiments of the disclosure.

Referring now to FIG. 24, in which (a) illustrates a cross-sectional view and (b) illustrates a top view, a sensor device 2400 including a nanopore and multiple devices surrounding the nanopore is illustrated. Sensor devices can include any suitable number of devices surround a nanopore, such as 1, 2, 3, 4, between 2 and 100, between 2 and 12, between 2 and 8 device, or between 4 and 8 devices. In the illustrated example, four devices 2402, 2404, 2406, and 2408 are formed about a nanopore 2410. Each of the four devices 2402-2408 can be operated independently of other, and each can produce a signal in response to detecting one or one or more ions, atoms, molecules, or particles traveling through the nanopore.

By way of examples, each of the four devices 2402-2408 can sense DNA translocation independently or other characteristic of a molecule as the molecule or material passes through nanopore 2410. Each of the devices can be operated with, for example, an AC signal with different frequencies, ranging between 1 Hz to 10 GHz. Each frequency can be further optimized to detect a specific molecule or discriminate and detect unique DNA base. By computational analysis of signal from multiple sensors, base discrimination for sequencing can be made with high accuracy. Additional exemplary uses of sensor device 3400 are described in more detail below.

In the illustrated example each of the devices is a field effect transistor including a source region 2412, a drain region 2414, a channel 2416, and a gate structure 2418, such as source regions, drain regions, channel, and gate structures described herein. Each of the plurality of devices comprises a channel region proximate the nanopore. Further, in the illustrated example, the source region is formed proximate a first surface of a layer including the nanopore and the drain region is formed proximate a second surface of the layer comprising the nanopore. Each of the plurality of devices 2402-2408 can include a vertical or C-shaped (concave or convex) or V-shape gate structure as described herein. Further, two or more (e.g., all three) of a source contact, a drain contact, and a gate contact are formed on the same surface of the substrate, as illustrated in FIG. 24.

Although illustrated as FET devices, each of the plurality of devices 2402-2408 can include one or more of: field effect sensor, plasmonic sensor, interferometric sensor, waveguide sensor, cantilever sensor, acoustic sensor, QCM sensor, ultrasonic sensor, mechanical sensor, thermal sensor, fluorimetric sensor, optical dye based sensor, calorimetric sensor, luminometric sensor, quantum dot sensor, quantum-well sensor, graphene sensor, MoS2 sensor, 2D material sensor, nanotube sensor, nanowire sensor, enzymatic sensor, electrochemical sensor, potentiometric sensor, and conductometric sensor or capacitive sensors or electron-spin sensor.

Figure 44:
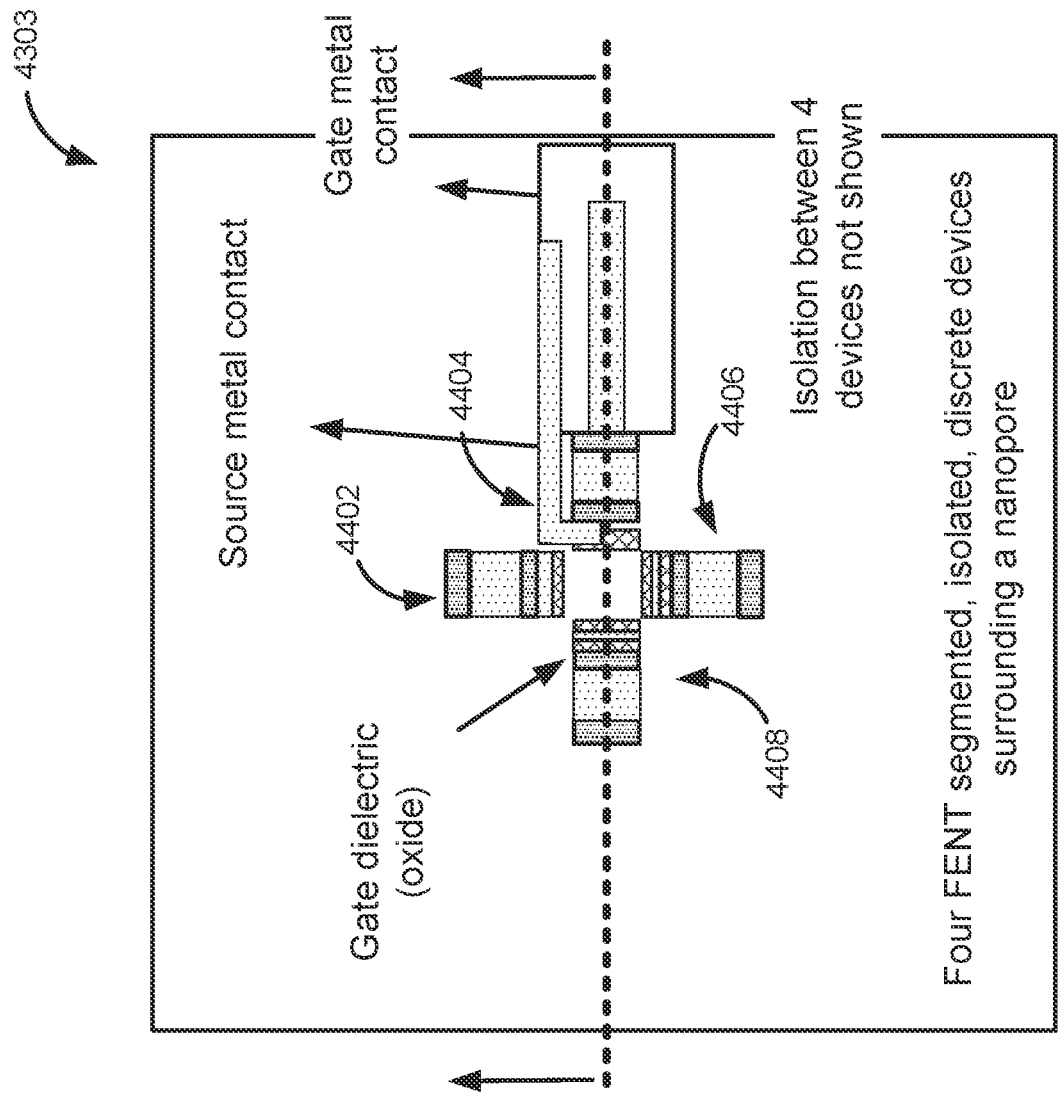
FIG. 44 illustrates another sensor device in accordance with additional exemplary embodiments of the disclosure.

FIG. 44 illustrates another sensor device 4400 that includes a plurality of devices 4402-4408 surrounding one or more nanopores 4410. Similar sensor device 2400, each of the plurality of devices 4402-4408 can include a source, drain, channel, gate, contacts, and other layers as described herein. In this case, as with sensor device 2400, the individual devices can be operated independently and in different modes (e.g., inversion, depletion, accumulation, and the like) to redundantly or combinationally characterize DNA, protein, or other biopolymer with speed and accuracy.

Figure 45:
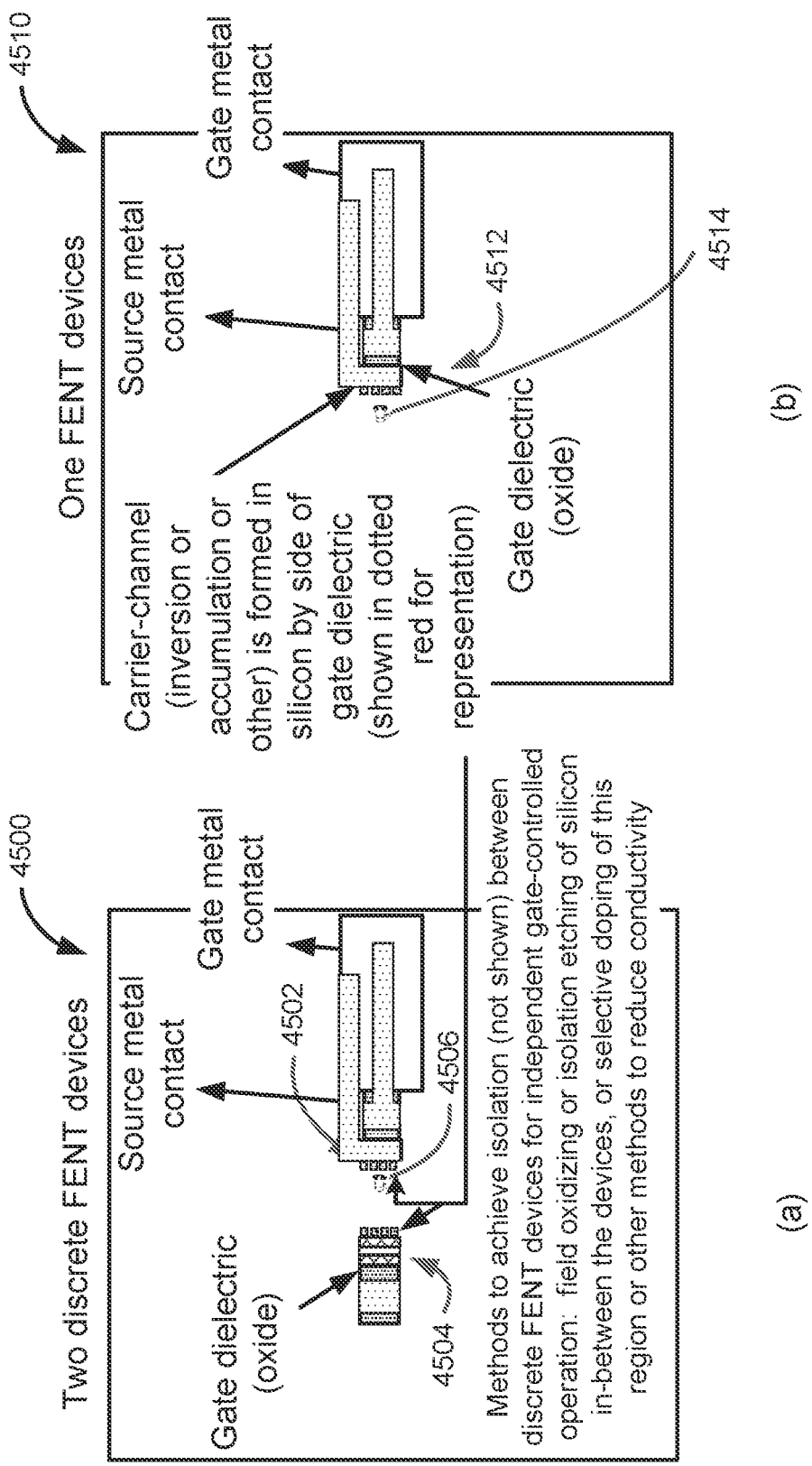
FIG. 45 illustrates (a) a two device and (b) a single device sensor device in accordance with additional exemplary embodiments of the disclosure.

FIG. 45(a) illustrates a sensor device 4500 two discrete devices 4502, 4504 formed about one or more nanopores 4506 and FIG. 45(b) illustrates a sensor device 4510, including one device 4512 formed about one or more nanopores 4514.

Figure 25:
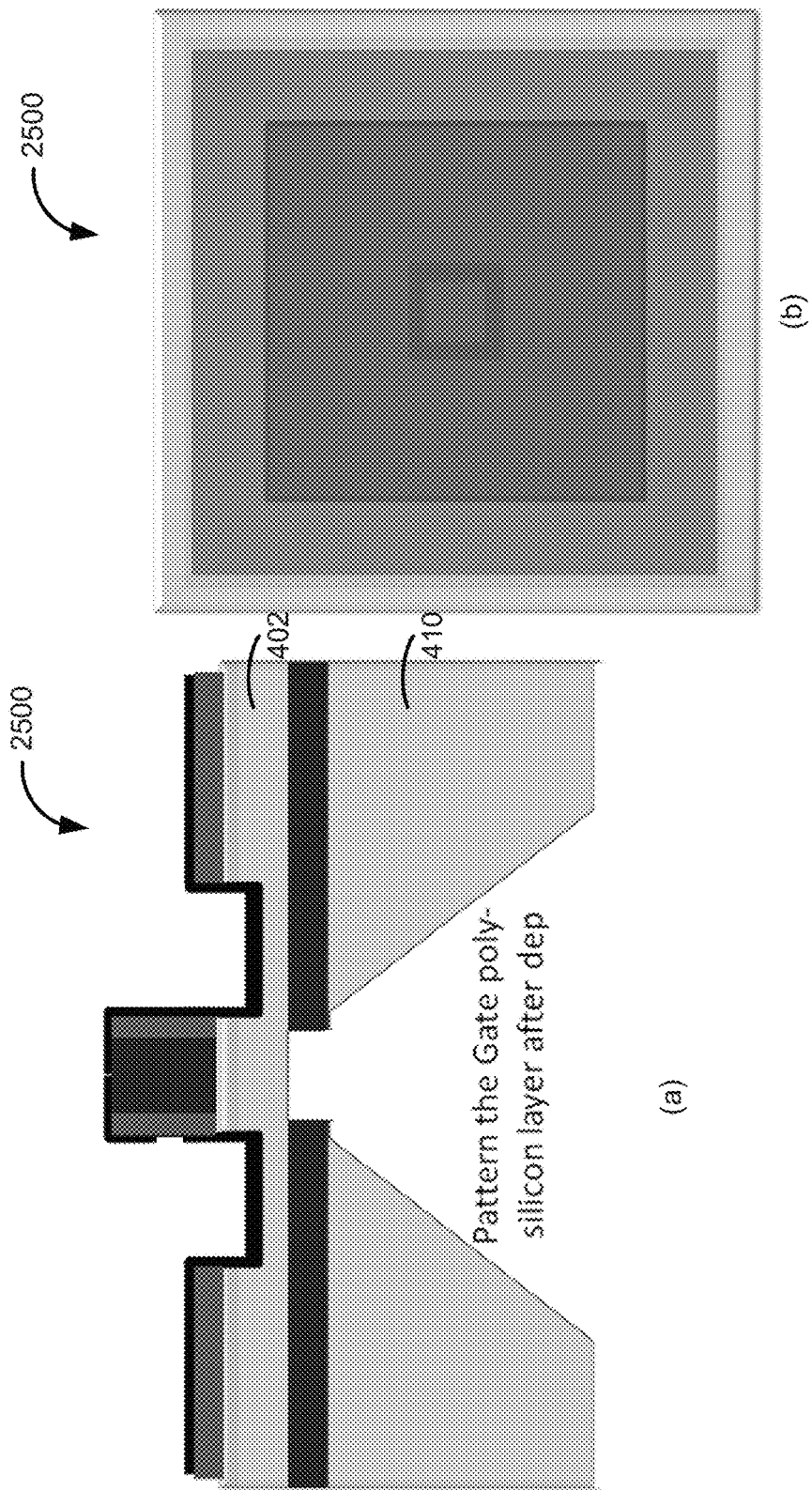
Figure 26:
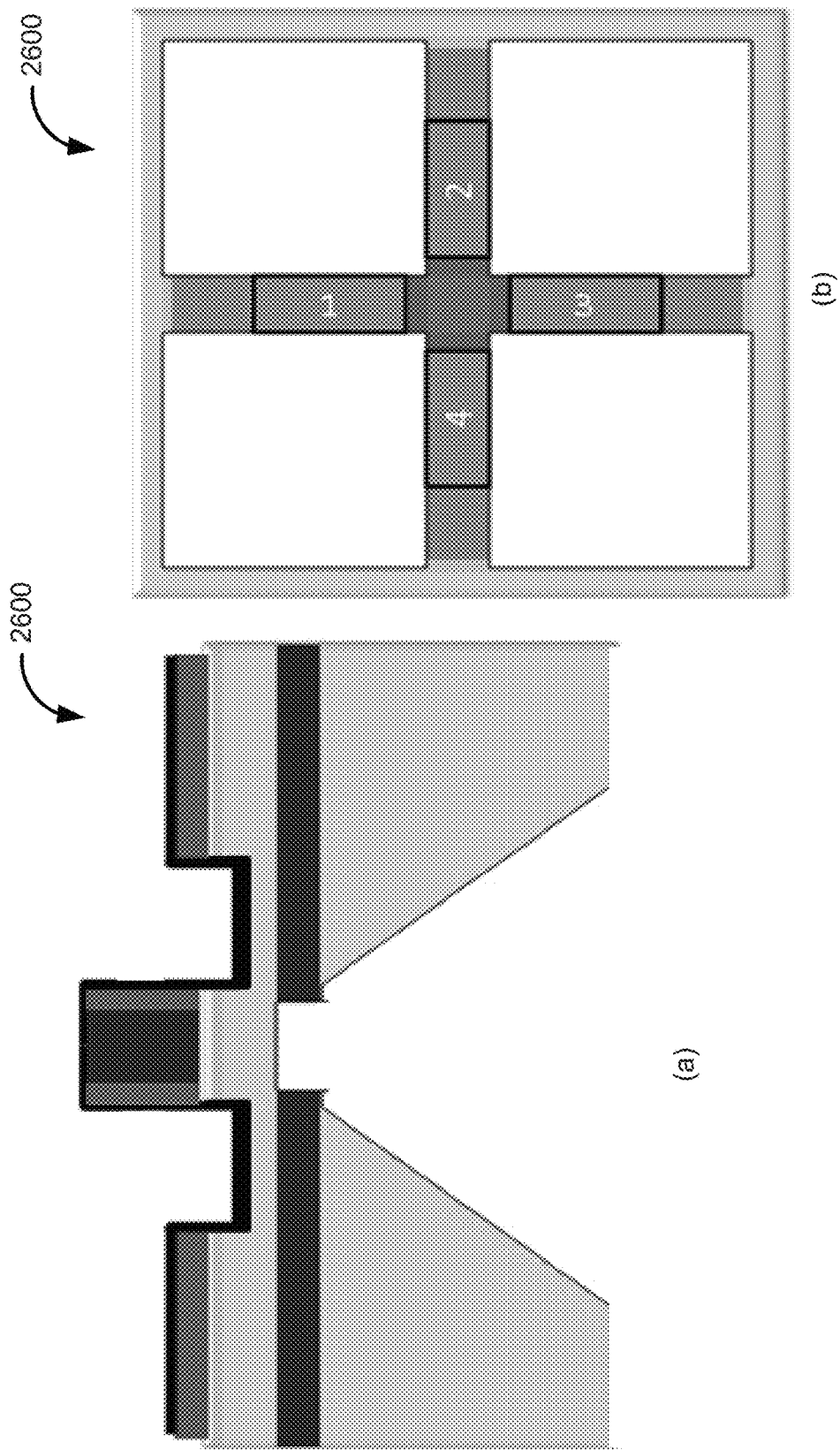

Turning now to FIGS. 25 and 26, in which (a) illustrates a cross-sectional view and (b) illustrates a top view of a structure 2500 and 2600, fabrication of sensor device can be similar to the fabrication steps described above in connection with structure 100, except after the gate material deposition (e.g., LPCVD poly silicon/metal deposition) step described above, the gate material (e.g., polysilicon) layer is patterned and etched into sections to form structure 2600, illustrated in FIG. 26. The patterning can be done by, for example, coating an EBL resist and aligning to central oxide square and pattern, to split into 4 devices, illustrated as 1, 2, 3, and 4 in FIG. 26. The remaining steps of the process to form sensor device 2400 are similar to those described above.

Method of Using the Device

The devices, including sensor devices, described herein can be used to detect and characterize a variety of materials, including organic molecules, ionic species, nanoparticles, molecular species, materials selected from the group consisting of a DNA molecule, a protein molecule, a peptide molecule, a polypeptide molecule, an RNA molecule, a synthetic oligo nucleotide molecule, and a synthetic peptide or polypeptide molecule, or a combination of these materials, and any of these materials modified with at least one tag selected from the group consisting of metal species, metal-organic species, chemical modifiers, biomolecular tags, complementary hybridizing chain molecules, peptides, polypeptides, oligonucleotides, zinc fingers, nano particles, quantum dots, organic dyes, beads, nanowires, and nanotubes.

Techniques useful in characterizing materials are provided in the following publications, which are included herein by their reference in their entirety, to the extent their contents do not conflict with the present disclosure.

Frequency Domain Detection of Biomolecules using Silicon Nanowire Biosensors Gengfeng Zheng,*† Xuan P. A. Gao,*‡ and Charles M. Lieber§ ||

Nano Lett. 2010 Aug. 11; 10(8): 3179-3183.

doi: 10.1021/nl1020975

Detection beyond the Debye Screening Length in a High-Frequency Nanoelectronic

Biosensor

Girish S. Kulkarni and Zhaohui Zhong*

Nano Lett., 2012, 12 (2), pp 719-723

DOI: 10.1021/nl203666a

Electrochemically Controlled Layer-by-Layer Deposition of Metal-Cluster Molecular Multilayers on Gold†

Masaaki Abe et al

Angewandte Chemie International Edition

Volume 42, Issue 25, June 2003

Molecular Self-Assembly at Metal-Electrolyte Interfaces

Int J Mol Sci. 2013 March; 14(3): 4498-4524.

Thanh Hai Phanl,* and Klaus Wandelt1,2,*

Method for electrochemical deposition of monolayers on metallic surfaces and objects coated with an organic monolayer US Publication No. 20100133107 A1

Figure 27:
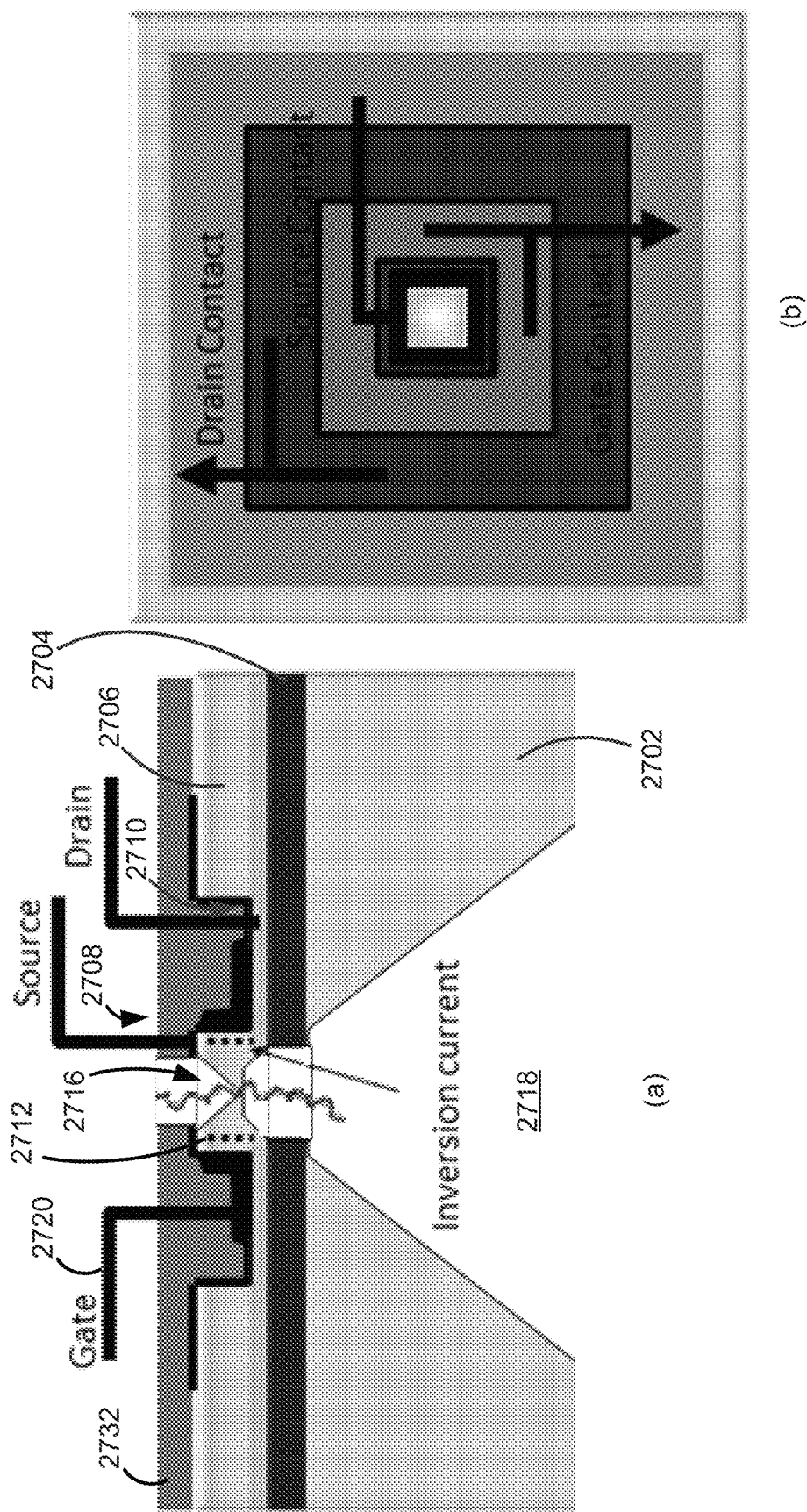
FIG. 27 illustrates a device in accordance with additional exemplary embodiments of the disclosure.

FIG. 27 illustrates a device 2700, including a substrate 2702, an etch region 2718 formed within a portion of substrate 2702, an insulating layer 2704 proximate etch region 2718, a semiconductor layer 2706 formed overlying insulating layer 2704, a source region 2708 formed using a first portion of the semiconductor layer 2706, a drain region 2710 formed using a second portion of the semiconductor layer 2706, a channel 2712 formed using a third portion of semiconductor layer 2706, wherein channel 2712 spans between source region 2708 and drain region 2710, and one or more nanopores 2716. As illustrated, channel 2712 surrounds one or more nanopores 2716. Device 2700 can also include a encapsulant 2732. Device 2700 may additionally include additional insulating, semiconductive, and conductive layers, such as those described herein and can be the same or similar to device 100. In the illustrated example, device 2700 is biased using gate 2720 to form an inversion current in channel 2712.

Figure 28:
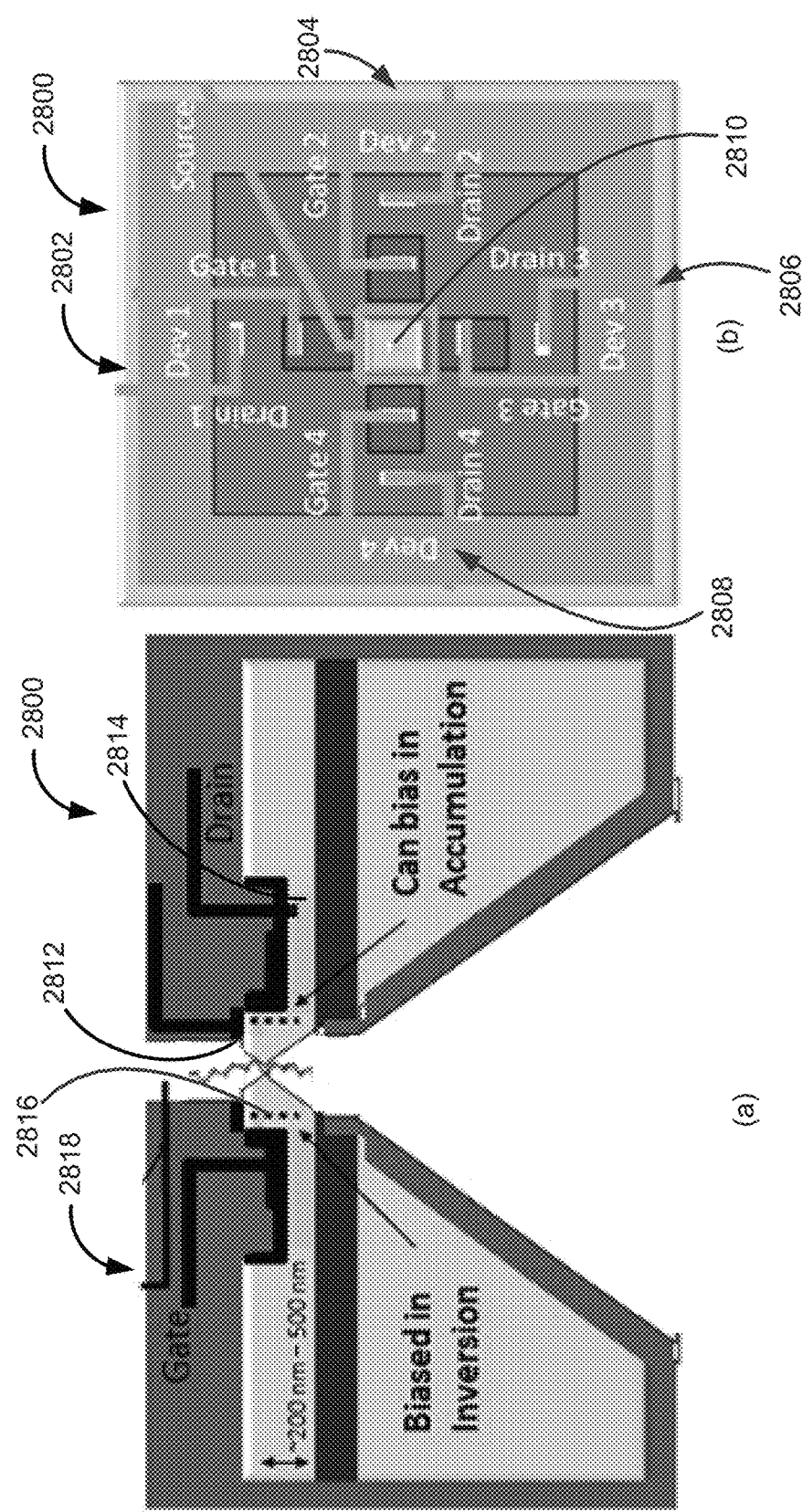
FIG. 28 illustrates a sensor device in accordance with additional exemplary embodiments of the disclosure comprising of plurality of sensors surrounding one or more nanopores.

FIG. 28 illustrates a sensor device 2800, including devices 2802-2808, surrounding a nanopore (or multiple nanopores) 2810. Sensor device 2800 includes a source region 2812, a drain region 2814, a channel 2816, and a gate structure 2818. Sensor device 2800 can be the same or similar to sensor device 2400. In the illustrated example, gate structure 2818 can be biased, such that a device (e.g. device 2802) operates in inversion or accumulation mode. As noted above, each device 2802-2808 can operate independently and each device can operate in the same or different modes.

Figure 29:
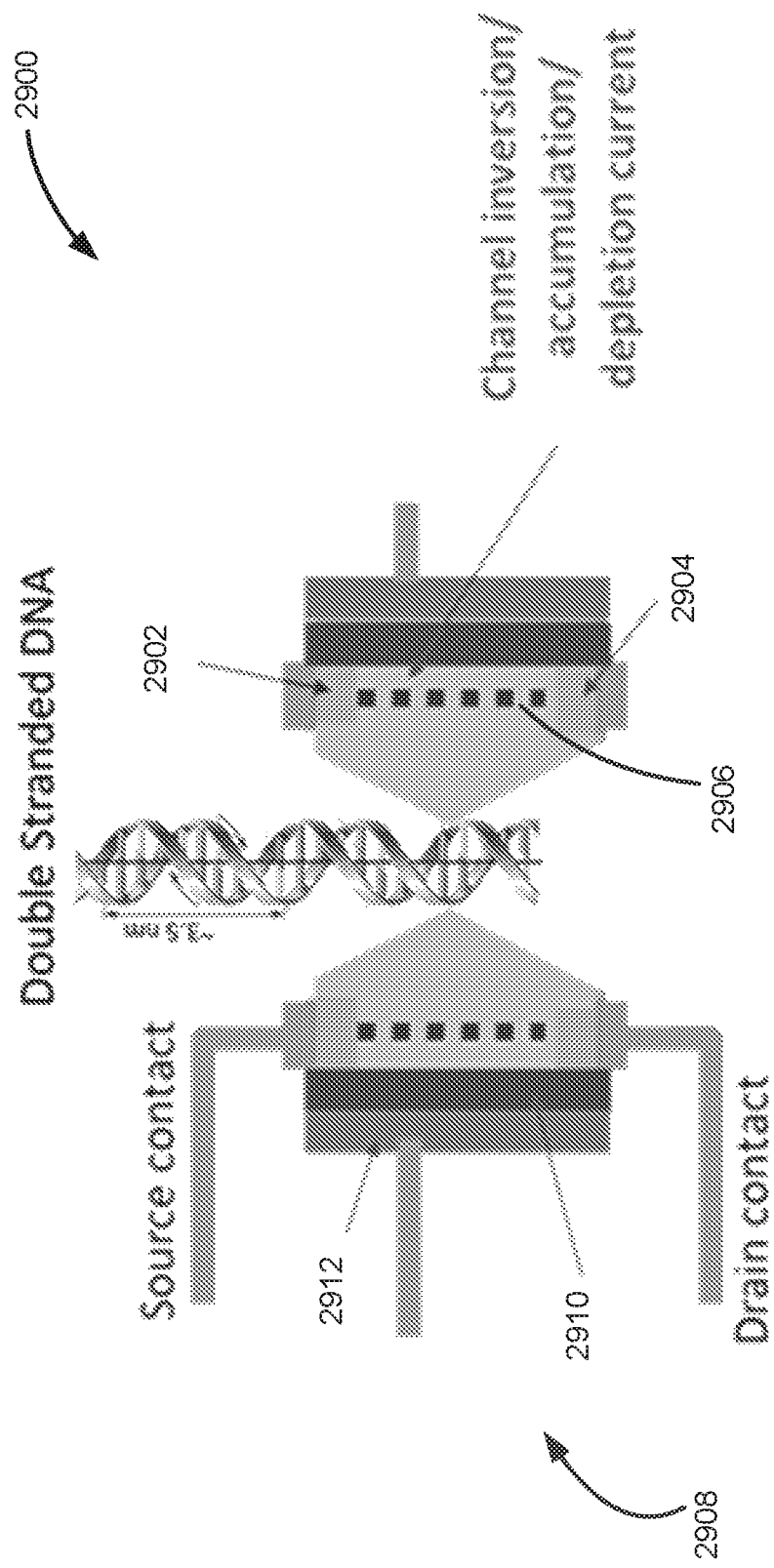
FIG. 29 illustrates operation of a device in accordance with exemplary embodiments of the disclosure.

FIG. 29 illustrates a device 2900, which may form part of a sensor device including multiple devices above one or more nanopores. In the illustrated example, device 2900 includes a source region 2902, a drain region 2904, and a channel 2906, and a gate region 2908, including a gate oxide 2910 and a gate metal 2912. With the multiple devices, multi-stranded DNA molecules as well as other molecules, such as protein post translational markers (PTMs) and/or protein mutations, pr other molecules can be characterized.

Detecting Protein PTMs and/or Protein Mutations for Disease Diagnostics

Figure 30:
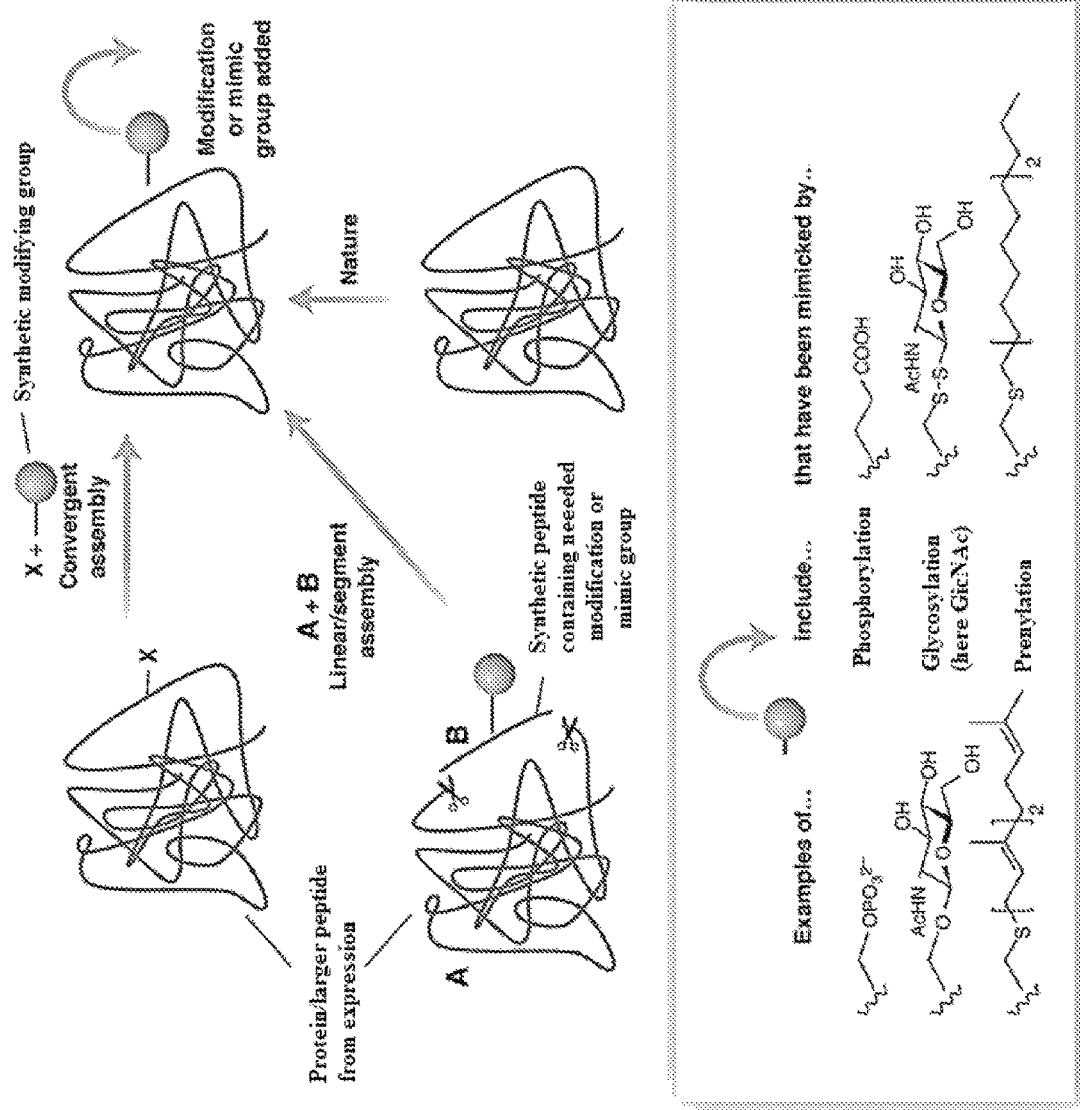
FIG. 30 illustrates modification of proteins in accordance with various embodiments of the disclosure.

Detecting protein post translational markers (PTMs) and/or protein mutations on test proteins acquired from a patient or test individual will enable disease diagnostics and prognostics and drug discovery. For detecting PTMs or protein mutations, we may use full proteins stretched from n to c terminals and/or fragment full proteins into smaller parts and then test the fragmented peptides or poly-peptides and/or the test proteins/peptides/poly-peptides can be modified with specific tags or modifications to aid detection and diagnosis, as illustrated in FIG. 30.

Detecting protein PTMs and mutations will enable early stage high accuracy diagnosis of diseases, as protein PTM characterization implies characterization of disease phenotype, hence will have very low false positives and false negatives in diagnosis and prognosis. It will also enable drug resistance testing, as specific protein mutations and/or protein PTMs are associated with specific disease sub-types that cause resistance to particular drug molecules. These protein mutations and/or protein PTMs can be detected directly using nanopore sensors, such as the sensors illustrated in FIGS. 28 and 29.

Figure 31:
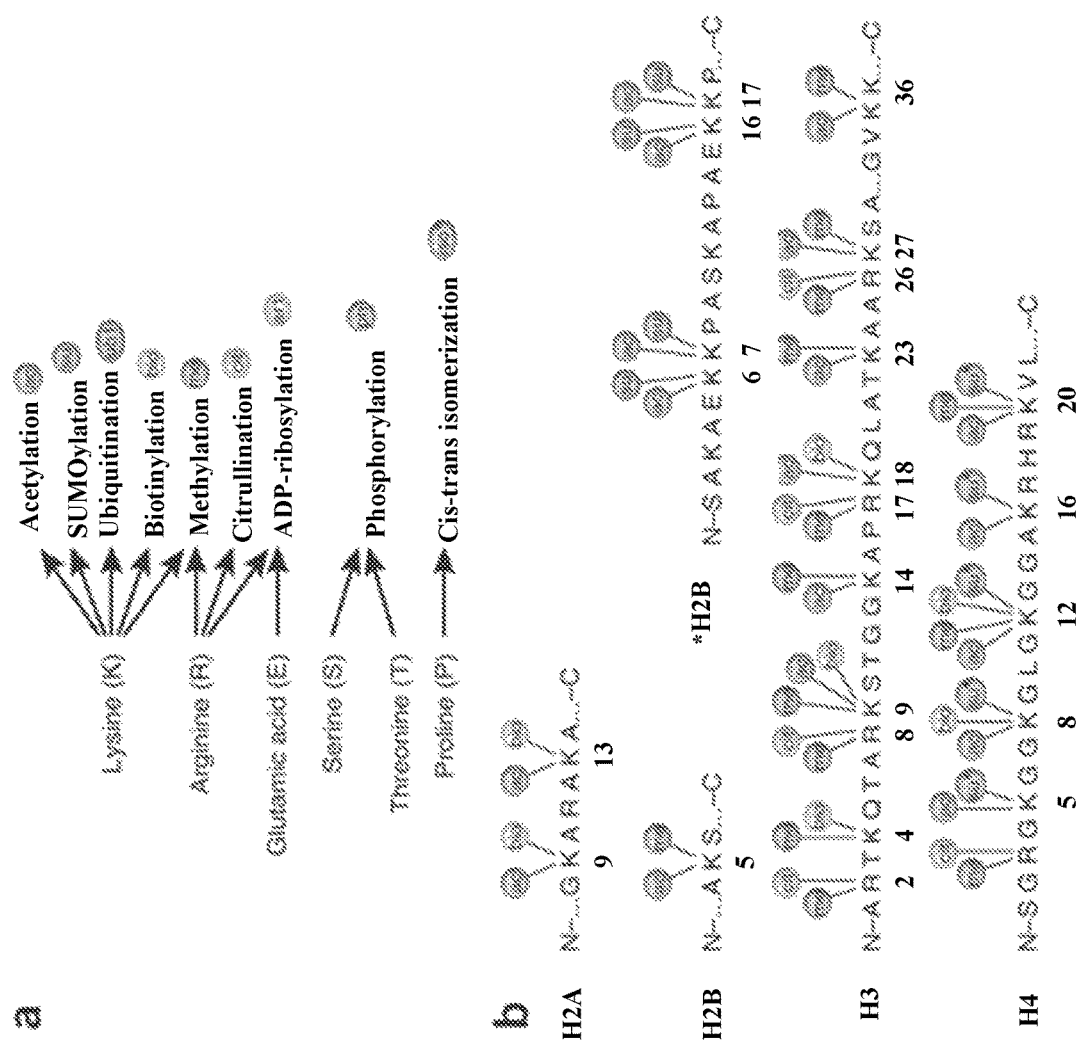
FIG. 31 illustrates PTM modifications in accordance with various embodiments of the disclosure.

Example PTMs of protein/poly-peptide/peptide include amino-acid markers produced by acylation, acetylation, deacetylation, formylation, alkylation, methylation, amidation, glycosylation, oxidation, glycation, phosphorylation, biotinylation, ubiquitination, SUMOylation, Neddylation, sulfation, pegylation, citrullination, dephosphorylation, deamidation, eliminylation, or nitration, Lipidation, biotinalation. Illustrative examples are shown in FIG. 31.

Figure 32:
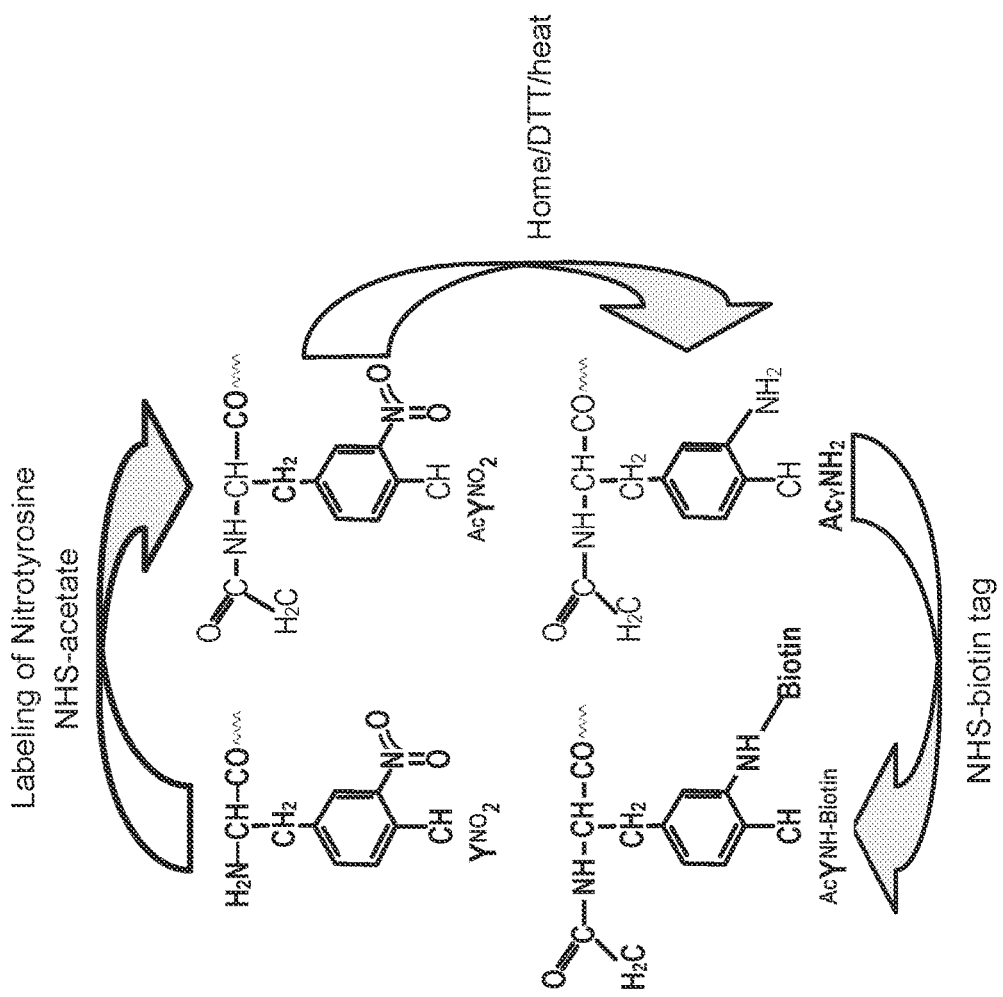
FIG. 32 illustrates labeling of Nitrotyrosine. in accordance with various embodiments of the disclosure.

Chemical modification of PTMs for detection: For example nitro-PTM detection can be achieved by labeling and then detecting with transistor-nanopore of present invention. Labeling of nitrotyrosine with biotin after reduction to aminotyrosine and subsequent acylation with an activated ester of biotin after initial blockage of all free amine groups with an activated ester of acetic acid can be characterized with the sensor devices described herein. FIG. 32 illustrates this process. Reference is made to Amino acids: Chemistry, functionality and selected non-enzymatic post-translational modifications, Rainer Bischoffa, Hartmut Schlüterb, Journal of Proteomics Volume 75, Issue 8, 18 Apr. 2012, Pages 2275-2296, the contents of which are hereby incorporated by reference, to the extent such contents do not conflict with the present disclosure.

Prior to detecting Protein PTMs or protein mutations or protein sequencing, proteins can be cleaved at specific locations using a enzymatic processes, and the resultant protein fragments—peptides or poly-peptides can be sequenced using nanopore—transistor sensor device of present disclosure. The term nanopore sensor includes any and all nanopore sensing or sequencing technology, including but not limited to devices and sensors described in present disclosure.

Figure 33:
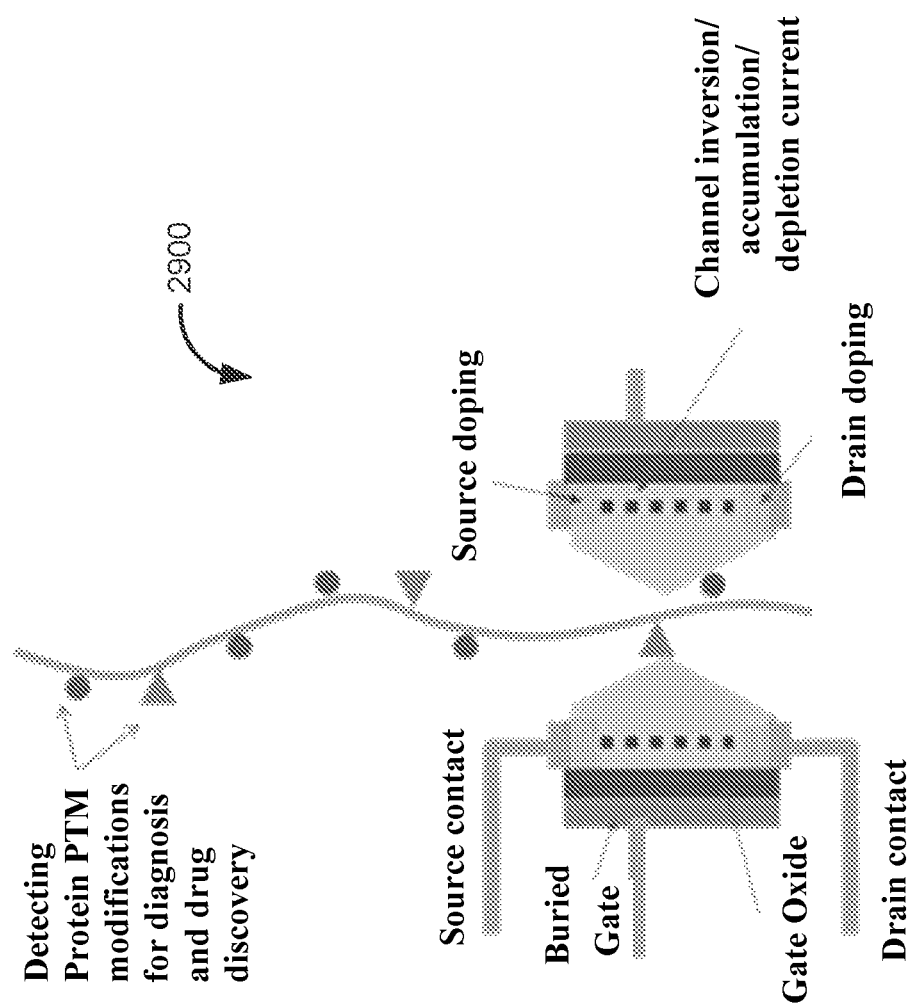
FIGS. 33-34, 36 illustrate use of devices in accordance with various exemplary embodiments of the disclosure for protein/polypeptide and/or modifications of proteins/polypeptides characterization or sequencing.
Figure 34:
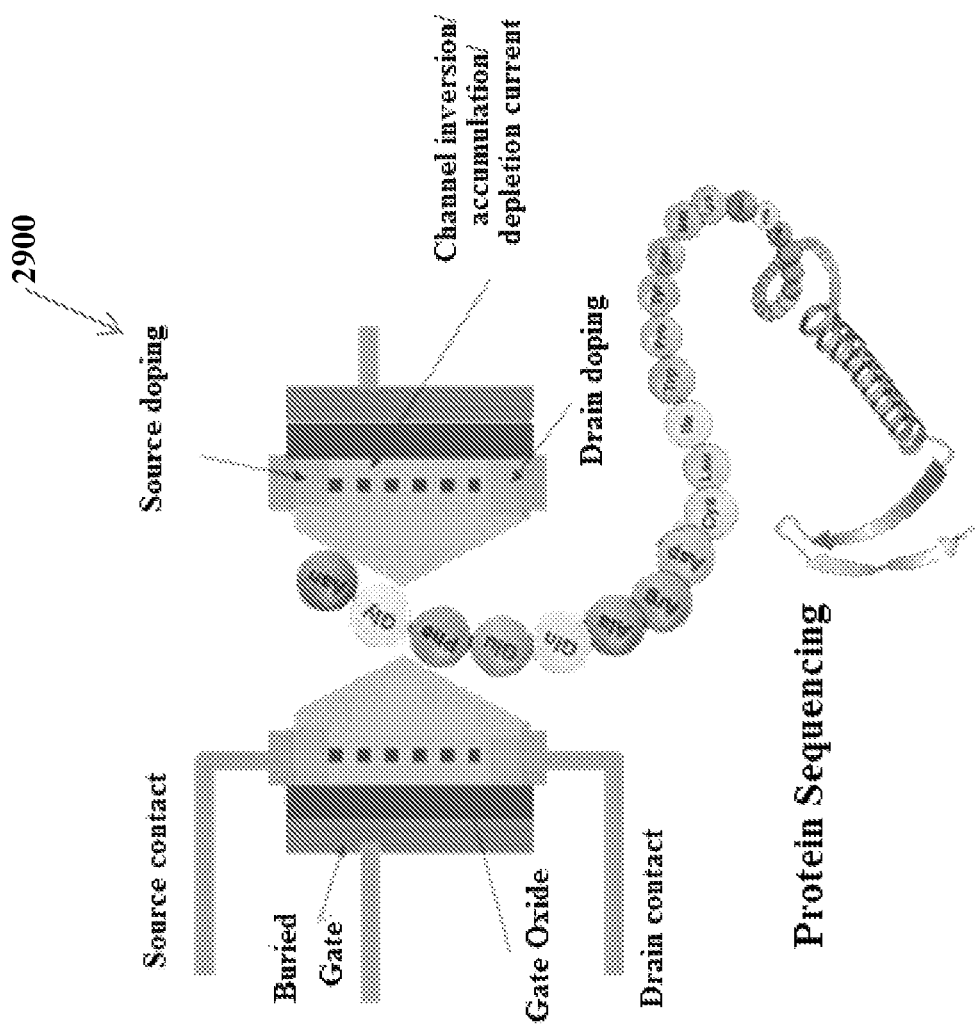
Figure 36:
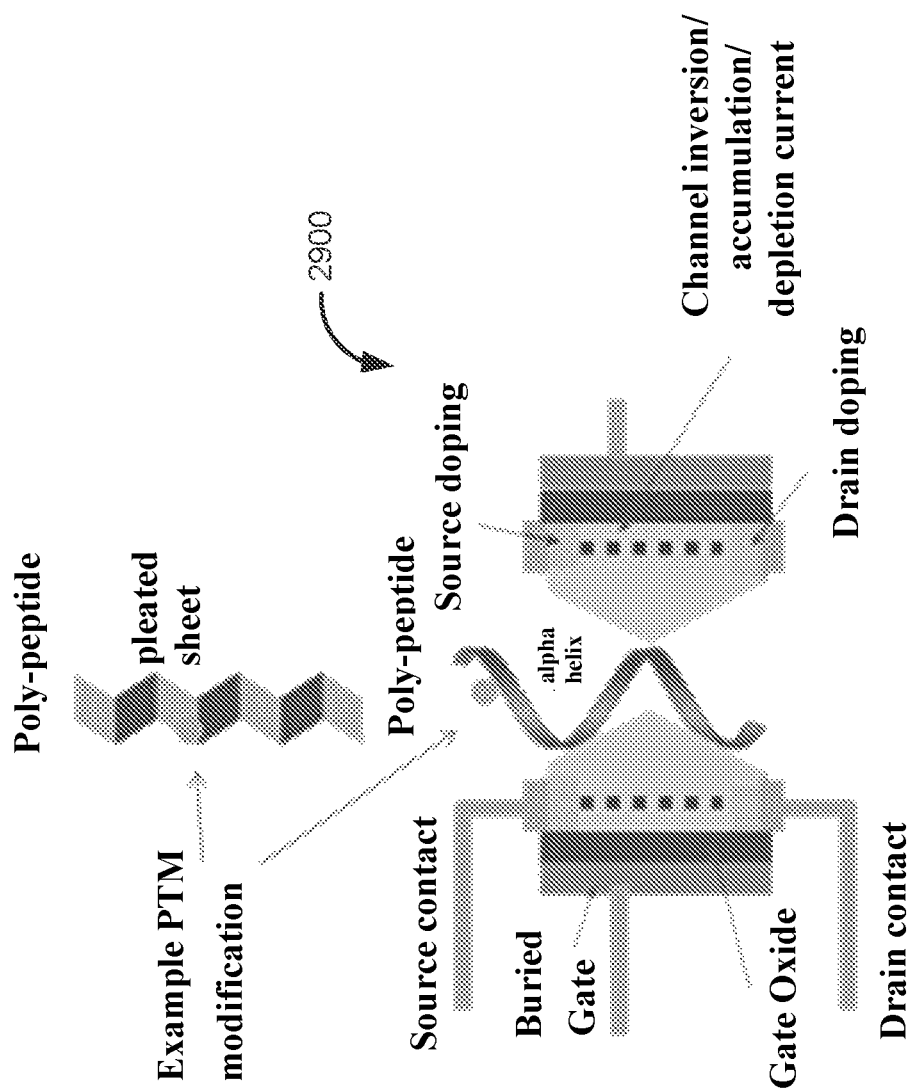

Protein fragmentation using enzymes, is described in the following article, the contents of which are hereby incorporated herein by reference to the extent such contents do not conflict with the present disclosure. https://www.thermofisher.com/us/en/home/life-science/protein-biology/protein-biology-learning-center/protein-biology-resource-library/pierce-protein-methods/overview-post-translational-modification.html FIG. 33 illustrates characterizing (detecting) PTM modifications using device 2900, which can form part of sensor device 2800. As noted in the illustration, this technique can be used for diagnosis of disease as well as for drug discovery. FIG. 34 illustrates protein sequencing using device 2900. FIG. 36 illustrates characterizing PTM modifications of a polypeptide using a device and sensor as described herein.

Detection and Sequencing of Epigenetic Modifications: Modifications on DNA/RNA and Modifications on Histones The following references are hereby incorporated by reference to the extent such references do not conflict with the present disclosure.

S. B. Rothbart, B. D. Strahl, Interpreting the language of histone and DNA modifications, Biochim. Biophys. Acta (2014), http://dx.doi.org/10.1016/j.bbagrm.2014.03.001

Epigenetic regulatory functions of DNA modifications: 5-methylcytosine and beyond, Achim Breiling and Frank Lyko, Epigenetics & Chromatin, 20158:24, DOI: 10.1186/s13072-015-0016-6

Epigenetic modulators, modifiers and mediators in cancer aetiology and progression, Andrew P. Feinberg, Michael A. Koldobskiy & Anita Göndör, Nature Reviews Genetics, 17, 284-299, (2016), doi:10.1038/nrg.2016.13

DNA Methylation and other DNA Epigenetic modifications detection:

The table below is from Reference: S. B. Rothbart, B. D. Strahl, Interpreting the language of histone and DNA modifications, Biochim. Biophys. Acta (2014), http://dx.doi.org/10.1016/j.bbagrm.2014.03.001

TABLE 1

Reading and interpreting DNA modifications.

| Modification type | Structure | Associated functions |
| --- | --- | --- |
| Cytosine (CpC) | 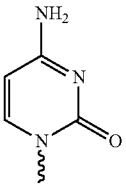 | Gene regulation |
| Methylation (5 mC) | 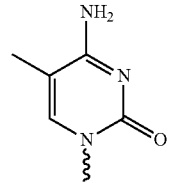 | X-inactivation, imprinting, long-term silencing, development, gene regulation |
| Hydroxymethylation (5 hmC) | 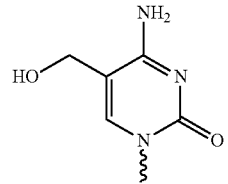 | ? |
| Formylation (5 fC) | 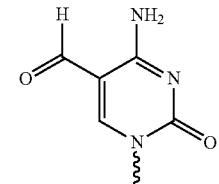 | ? |
| Carboxylation (5 caC) | 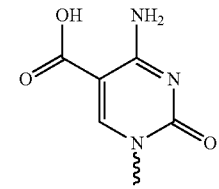 | ? |

Figure 35:
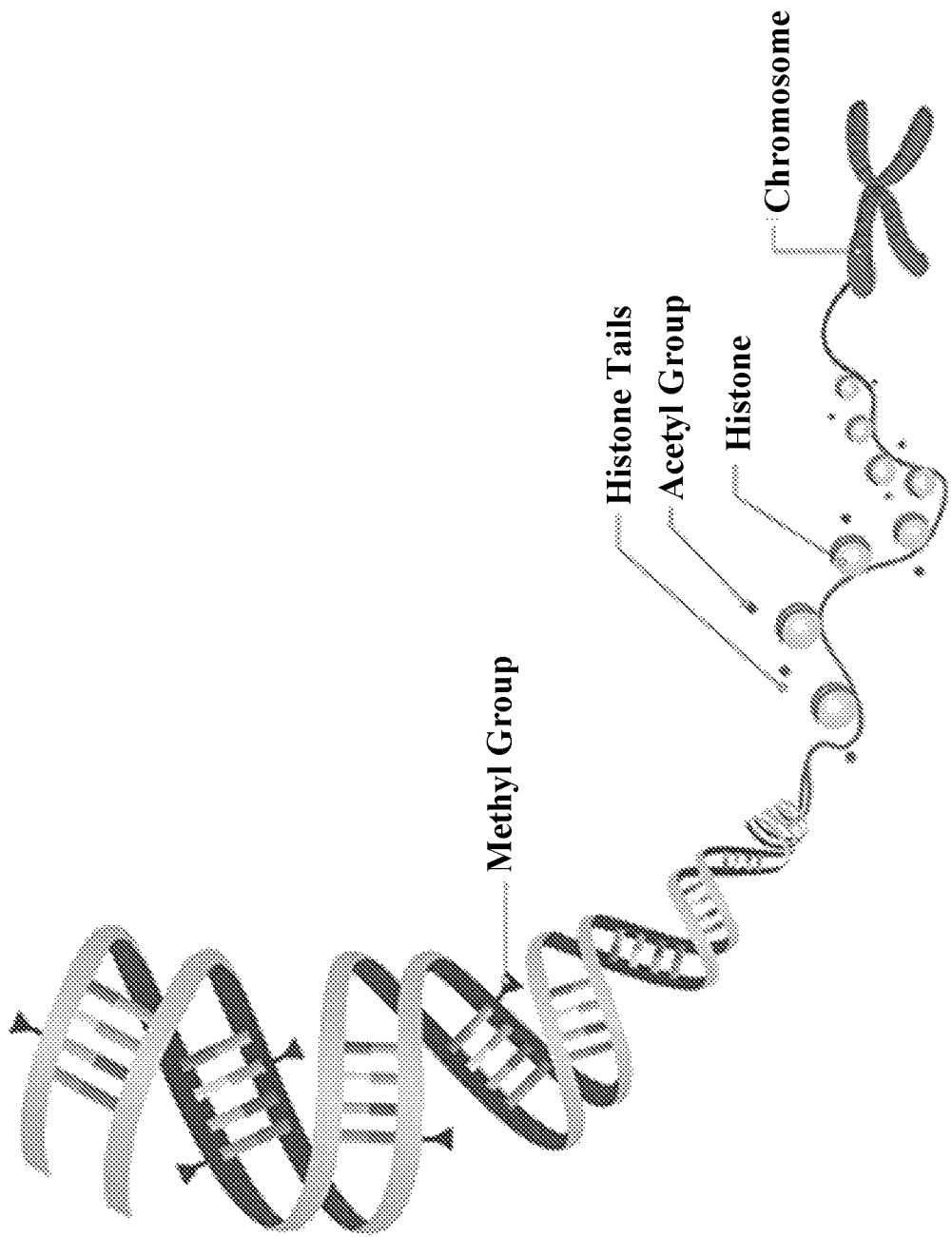
FIG. 35 illustrates a methyl group attached to DNA and acetyl group on histones, which can be characterized using devices and methods in accordance with the disclosure.

DNA methylation is an epigenetic mechanism used by cells to control gene expression. A number of mechanisms exist to control gene expression in eukaryotes, but DNA methylation is a commonly used epigenetic signaling tool that can fix genes in the "off" position. See, http://www.news-medical.net/life-sciences/What-is-DNA-Methylation.aspx: the contents of which are hereby incorporated herein by reference to the extent such contents do not conflict with the present disclosure. FIG. 35 illustrates a methyl group attached to DNA, which can be characterized using device 2900.

Figure 37:
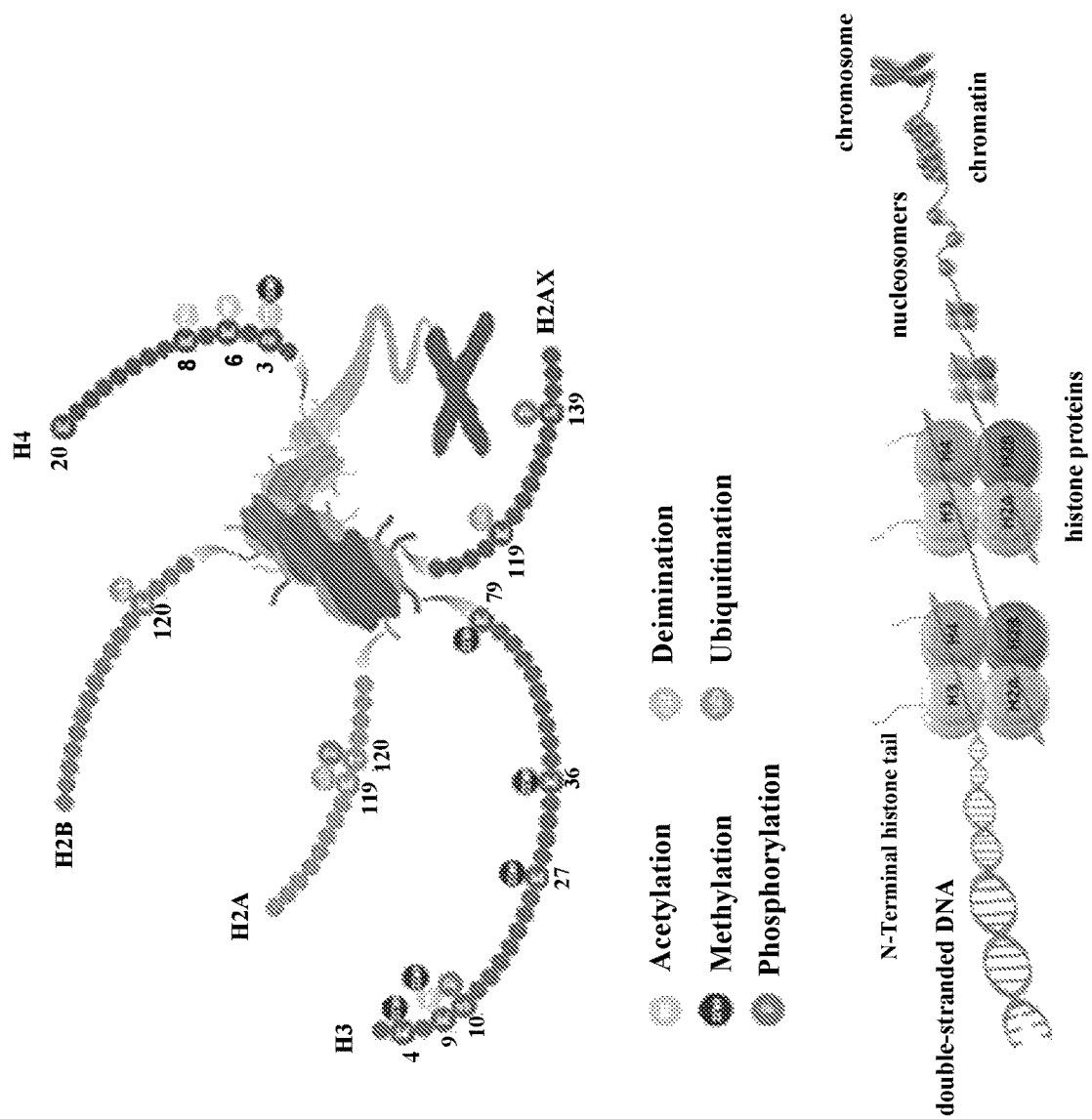
FIG. 37 illustrates double stranded DNA, histones, nucleosomes, chromatin, chromosomes, and epigenetic, post translational modifications on these, which can be characterized using devices and methods in accordance with the disclosure.

Histone modifications: Detection and Sequencing of Epigenetic Modifications on Histones and other DNA-packing proteins Histone modifications are post-translational modifications that regulate gene expression, with histone H3 being the most modified histone. See, http://www.abcam.com/epigenetics/histone-modifications-a-guide, the contents of which are hereby incorporated herein by reference, to the extent such contents do not conflict with the present disclosure. Sensor device 2800 and device 2900 can be used to characterize such modifications. FIG. 37 illustrates how markers using the sensor device of present invention will enable disease diagnosis and aid therapy.

Diagnosis of Alzheimers and Other Neurodegenerative Diseases by Detecting Protein PTMS and/or Protein Mutations (Tau, Amyloid, BASE, Alpha Synuclein)

Reference is made to the following articles, the contents of which are hereby incorporated herein by reference to the extent such contents do not conflict with the present disclosure.

Advances in blood-based protein biomarkers for Alzheimer's disease, Clark and Kodadek Alzheimer's Research & Therapy 2013, 5:18

Blood-Based Proteomic Biomarkers of Alzheimer's Disease Pathology, Frontiers in Neurology, November 2015|Volume 6|Article 236

Tau tangles, a hallmark of Alzheimers disease (AD): Hyper phosphorylation of microtubule associated protein Tau in neurons leads to Tau aggregation, formation of helical neurofibrillary tangles (NFT), and the density of NFT fibers in neocortex correlates directly with dementia, forming a hallmark of Alzheimer's disease (AD) pathology. Normal brain is expected to have an average of three phosphorylated residues per Tau protein, whereas this is expected to increase by three fold in Alzheimers disease. Tau protein is reported to have approximately 80 serine/threonine and 5 tyrosine phosphorylation sites, and dysregulation of tau phosphorylation (more specifically its hyper phosphorylation) leads to polymerization and NFT formation. The amount of total Tau protein in AD brain, comprising of regular Tau protein bound to microtubules, soluble hyper-phosphorylated Tau and insoluble hyper-phosphorylated NFT tangled Tau, is higher by a factor of 4 to 8 times compared to tau protein levels in healthy brain. Almost all of this increased Tau in diseased brain occurs in the hyper-phosphorylated form, further implicating Tau hyper-phosphorylation in AD.

Neuronal toxicity and synaptic dysfunction: While density of NFT in AD brain is a good indicator of the extant of neuronal damage, the NFT fibers themselves may not be the principal cause of dementia. Primary function of Tau and other MAP proteins is understood to be the binding and stabilization of microtubules, promotion of tubulin assembly in neurons. While majority of Tau in AD brain is hyper-phosphorylated, about 40% of it is reported to occur in cytosolic soluble hyper-phosphorylated Tau form, with rest being insoluble NFT tangled Tau form. Hyper phosphorylated Tau (and amyloid beta) proteins in AD brain are reported to occur in toxic cis isomeric forms (cis-Tau and cis-amyloid beta) that are immune to de-phosphorylation by phosphatases unlike the natural functional trans-forms. The cis isomer is kept in check by Pin1 prolyl isomerase activity that converts cis back to the healthy trans form, and Pin1 dysfunction has been implicated in AD pathology. In preliminary *drosophila* model studies it has been observed that it is this soluble cytosolic hyper phosphorylated Tau that mainly contributed to in vivo neuronal toxicity. It is therefore believed that hyper-phosphorylation of Tau prevents its interaction and binding with microtubules, in addition to sequestering other microtubule stabilizing MAP proteins into NFT filaments. This inhibits tubulin assembly and disrupts microtubular stability which leads to a total failure of axonal transport, synaptic function and internal communication within the nerve cell, eventually resulting in apoptosis.

Amyloid beta phosphorylation leads to formation of plaques in extra cellular spaces, another hallmark of AD. It has been reported that soluble amyloid beta dimers directly induce Tau hyper-phosphorylation, and tau interaction with amyloid beta and Fyn results in neurodegeneration. However it has been observed that in itself amyloid beta aggregation may not be a sufficient condition for loss of cognitive function, necessarily requiring Tau hyper-phosphorylation for loss of synaptic function. Recent reports indicate pathogenic infections and toxic pollution as possible insults that initiate innate immune response mechanisms which result in tau hyper-phosphorylation and neurodegeneration. Due to these reasons, Tau hyper-phosphorylation is accepted as a rational target for therapeutic discovery and disease diagnosis and is an area of increasing research interest. This is complemented by research on inhibiting phosphorylation initiated amyloid beta aggregation and promoting amyloid plaque clearance as other active therapeutic target areas in AD.

Dynamic hyper-phosphorylation of Tau in AD: Role of Tau hyper-phosphorylation in the formation of neurodegenerative tangles in Alzheimers has been known for a long time. However, notwithstanding decades of intense research, we do not yet have any successful outcomes either in terms of developing effective therapeutics or in developing high-accuracy early diagnostics for AD and other neurodegenerative diseases. While a major reason for this is the blood-brain-barrier drug development bottleneck, another critical reason for this is the complexity underling the Tau hyper-phosphorylation mechanisms, their role and relevance in AD pathogenesis. Almost one fourth of amino acid residues on Tau strands can be phosphorylated by a variety of kinases (proline and non-proline kinases), including PKA, PKB, PKC, PKN, AGC, MSK1, SGK1, p70S6K, ROCK, p110, CaMK II, AMPK, CAMK, MARK, CK1, CK1, TTBK, CDK5, ERK1/2, JNK, CMGC, GSK-3β, DYRK1A, SAPK, RSK, BRSK, CDC2, CK2, among others.

It has been found that not all hyper-phosphorylation sites on Tau are equally critical for neuronal toxicity, with phosphorylated residues in central region (e.g. T212, T231, S235, S202, S262) implicated in preventing Tau interaction with microtubules thus leading to acquiring of pathological function.

Devices and sensors as described herein can be used to detect PTMs and mutations on Tau protein, amyloid proteins, amyloid beta, Alpha synuclein and other proteins, for diagnosing Alzheimer's and other neurodegenerative diseases.

Example

Figure 38:
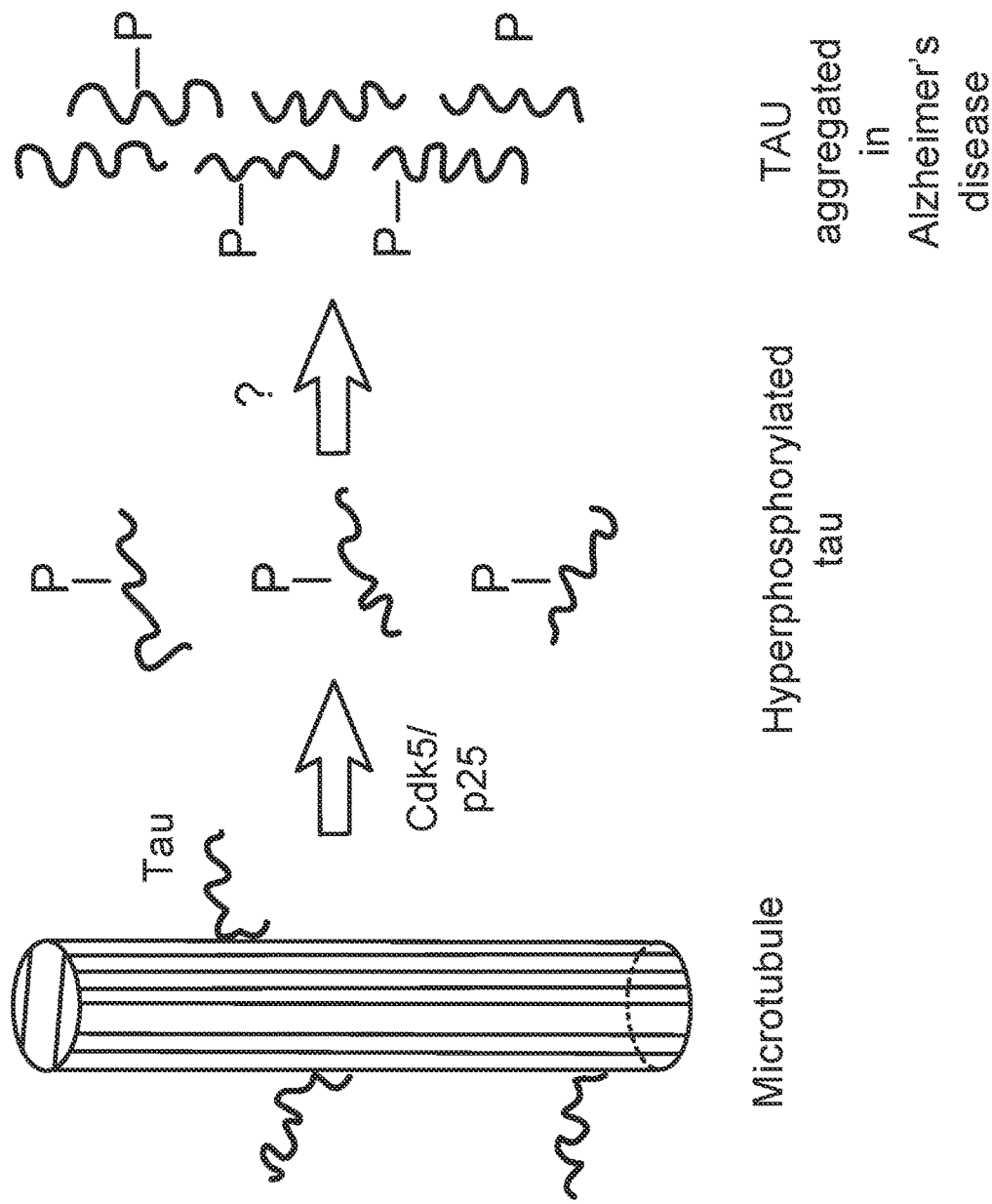
FIGS. 38 and 39 illustrate Tau that can be characterized in accordance with various embodiments of the disclosure.
Figure 39:
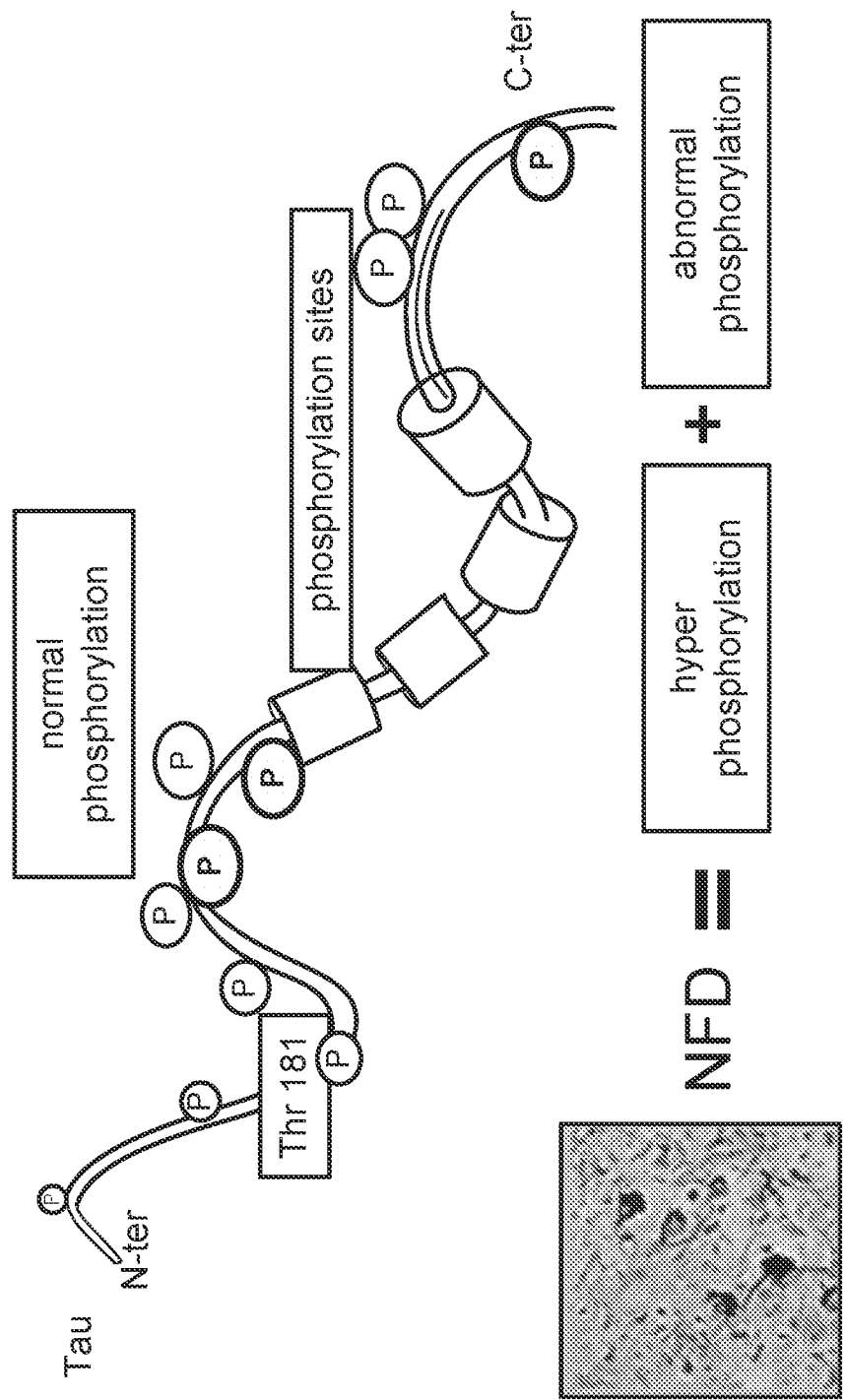

As illustrated in FIGS. 38 and 39, Tau is a strand like protein. It is phosphorylated (and also other PTMs involved) in Alzheimers, at many sites. Using a sensor device, such as device 2800, one can detect the locations of Tau phosphorylation, which is a very specific and sensitive biomarker detection method of Alzheimers diagnostic.

Additional Methods for Sequencing Include the following.

Sequencing of Unmodified ssDNA:

Devices as described herein can be operated as sensor in different modes of operations, viz potential coupled mode and charged coupled mode. Base charge induced potentials on nanopore capacitor electrodes on the order of a milli volt have been reported in literature, varying between bases in magnitude and spatial distribution, calculated in response to external applied fields in a nanopore capacitor. Potential variation on the order of few ten micro volts to milli volts should be detectable by operation of a device as described herein in potential coupled mode (device has very less defect states). A DNA nucleotide translocating at high speeds of microseconds per base through a nanopore constriction of few nm in diameters, sees an AC signal at 100 K to 1M Hz frequencies and an amplitude of few hundred micro volts. Such potential variation will be amplified at an edge of the nanopore, and further by the device coupling with the inversion channel. Device coupling with inversion or accumulation channel may be exponential in fully depleted films. A FET device operating at or above 10 MHz frequencies with internal amplification factor (combined amplification due to nanopore-curvature field and device coupling) is expected to be able to detect an unmodified DNA nucleotide passing at mega base per second speeds.

The above mentioned potential variation during translocation through a nanopore device is associated with charge variations, more specifically dipole variations between individual bases. Such charge, dipole variations can be read by a device in accordance with the present disclosure in charge coupled mode. We have demonstrated using a planar device charge, dipole coupling sensitivity up to few parts per trillion in gaseous phase detection of amine ligation. Using a device in accordance with the present disclosure, one expects charge coupling to be amplified further, with higher selectivity of base readout. But the read out speed in charge coupling mode is limited by interface trap state coupling speed which is in milli second time scales. Hence device charge coupling is slower than device potential coupling by orders of magnitude.

The present methods may be used on modified DNA nucleotides and on unmodified DNA.

Sequencing by Hybridization:

In accordance with various embodiments of the disclosure, a method uses ssDNA hybridized with 7-mer probe strands. As one example, the 7-mer probe strand will consist of a combination of 4-mer combinatorial base sequences and a 3-mer universal base common to all combinations. Using this approach, translocation of a lengthy DNA strand with discrete probe hybridized regions, passing through the nanopore at mega base per second speeds, is detectable with much higher sensitivity compared to a unmodified DNA strand. This would then need a total of 44 (256) separate probe hybridized translocation experiments for sequencing of a full genome.

Sequencing of Chemically Modified ssDNA:

Another method of investigation for optimized potential and charge transduction using a device in accordance with the present disclosure is chemical modification of DNA strands in base selective fashion. Chemical modifications can use charged species or bulk moieties such as base selective DNA, organic molecule, peptide, protein molecules or metal or metal-organic moieties. Such base specific modification on single stranded DNA enables sequencing via translocation through use of devices of the present disclosure. Examples of chemical modification of bases are: Translocation of RecA-coated double-stranded DNA through solid-state nanopores; chemical modification of thymine-osmium oxidation of thymine; detection of methylated cytosine as one approach to cytosine sequencing; or cytosine can be chemically labeled and sequencing by sulphonation followed by deamination; chemical modification of guanine-methylene-blue sensitized photo-oxidation of guanine can be used to selective sequence guanine occurrence in the DNA strand.

High Fidelity DNA Sequencing Using RCDAs:

Devices in accordance with exemplary embodiments of the disclosure can be designed, fabricated and operated as n-channel devices or as a p-channel devices with a hole inversion layer formed at, for example, the oxide-silicon channel interface. Since fabrication of these devices may be based on CMOS VLSI technology, it is possible to fabricate both re-channel and p-channel devices side-by-side with a few hundred micron spacing between them.

A purpose of having both n-channel and p-channel device nanopores is that their respective responses to potential and charge variations at the point nanopore location will be in opposite directions. A small increase in potential applied to sensitive surface of an n-channel device sensor produces an increase in inversion current (decrease in threshold voltage). Similar increase in potential produces a decrease in p-channel FDEC FET sensor. A time varying potential due to high speed molecular transport events through the nanopore, or equivalently, a small ($\mu$V to nV)) oscillating A.C signal produces an amplified oscillating signal measured across source and drain, with opposite responses (i.e., 180 phase shifts) from n-channel and p-channel FDEC devices.

Furthermore amplified sensing along similar lines is expected to happen when the semiconductor channel is biased into accumulation. An n-channel FET nanopore can be operated in FDEC inversion coupled mode or in amplified accumulation coupled mode, by simply biasing the gate at either ends of the Id-Vg curve. Alternately inversion or accumulation can be formed at the top surface of semiconductor film at the interface with solution, and the conductivity in this case can be modulated by changing the solution bias.

Each device can be fabricated in parallel with complementary p-channel and accumulation biased devices (along with few other possible variations). Each DNA segment may be sequenced simultaneously, with integrated microfluidics, using each of these different FET nanopore device transduction mechanisms. This will provide robust redundancy for attaining ultra-high fidelity DNA sequencing. Such arrays are termed redundant combinatorial detection arrays (RCDA).

Figure 40:
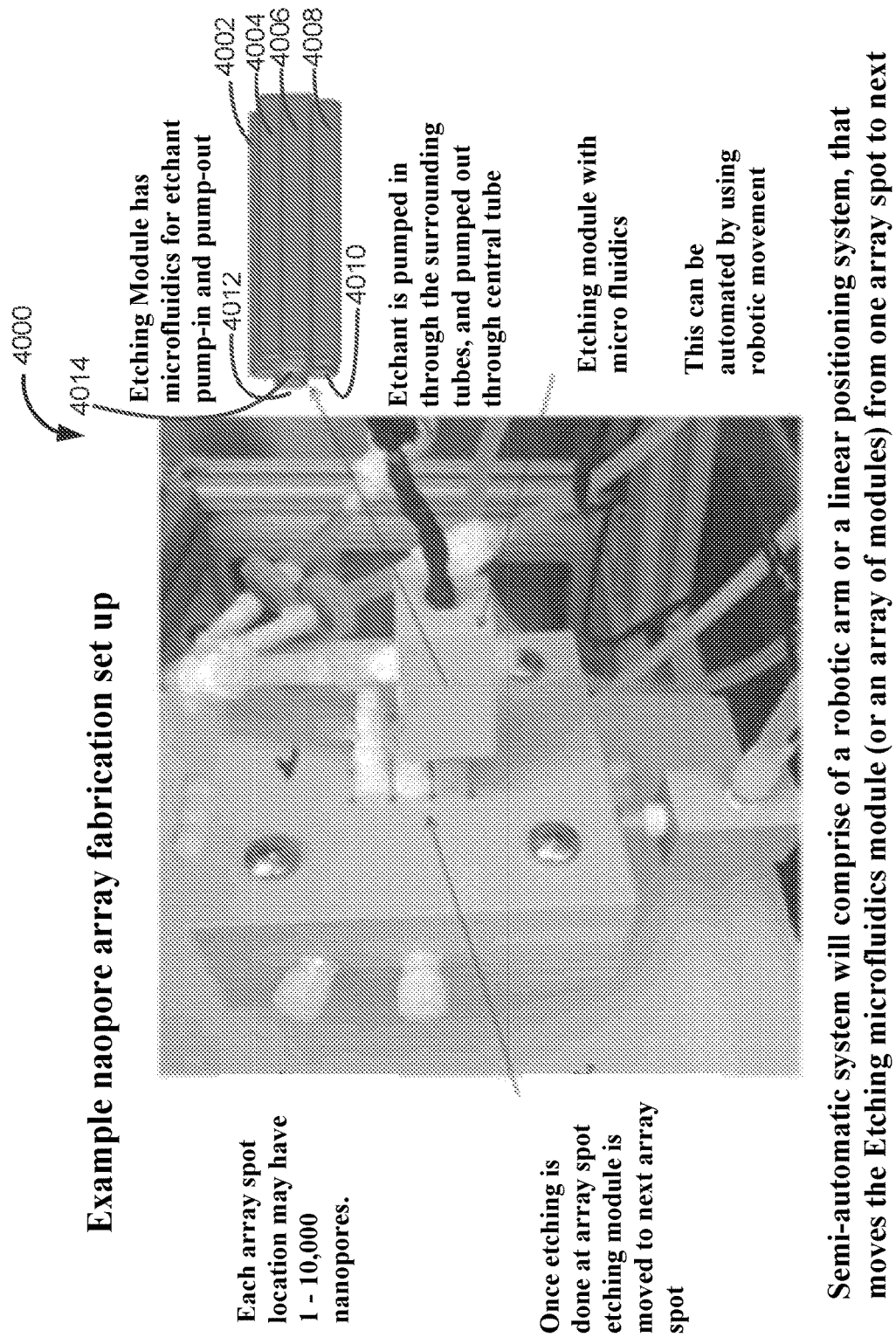
FIG. 40 illustrates an apparatus for forming nanopores in accordance with exemplary embodiments of the disclosure.

Turning now to FIG. 40, an apparatus 4000 for forming nanopores in accordance with various embodiments of the disclosure is illustrated. Apparatus 4000 includes one or more pumps to pump an etchant to a surface of a substrate, a plurality of tubes 4002-4012 coupled to the pump to provide etchant to the surface, and at least one tube 4014 to remove etchant from the surface, wherein the plurality of tubes provide the etchant to a portion of the surface. As illustrated, the plurality of tubes surround the at least one tube. Apparatus 4000 can further include a positioning system (not illustrated) to move the plurality of tubes and the at least one tube from one array area to another array area. Each array area may include 1 to 10,000 nanopores.

Every formulation or combination of components described or exemplified can be used to practice the invention, unless otherwise stated. Specific names of compounds are intended to be exemplary, as it is known that one of ordinary skill in the art can name the same compounds differently. One will appreciate that methods, device elements, starting materials, and synthetic methods, other than those specifically exemplified can be employed in the practice of the invention without resort to undue experimentation. All art-known functional equivalents, of any such methods, device elements, starting materials, and synthetic methods, and are intended to be included in this invention. Whenever a range is given in the specification, for example, a temperature range, a time range, or a composition range, all intermediate ranges and sub ranges, as well as all individual values included in the ranges given are intended to be included in the disclosure. When a Markush group or other grouping is used herein, all individual members of the group and all combinations and subcombinations possible of the group are intended to be individually included in the disclosure.

The present invention has been described above with reference to a number of exemplary embodiments and examples. It should be appreciated that the particular embodiments shown and described herein are illustrative of the invention and its best mode and are not intended to limit in any way the scope of the invention. It will be recognized that changes and modifications may be made to the exemplary embodiments without departing from the scope of the present invention. These and other changes or modifications are intended to be included within the scope of the present invention.

What is claimed is:

1. A method of forming a device, the method comprising the steps of:
    providing a substrate comprising a semiconductor layer having a source region proximate a first surface of the semiconductor layer using a first portion of the semiconductor layer and a drain region proximate a second surface of the semiconductor layer using a second portion of the semiconductor layer;
    etching a portion of the substrate to form a substrate etch region;
    forming a channel within a third portion of the semiconductor layer;
    forming a structure on the semiconductor layer;
    forming a spacer about the structure;
    using the spacer, forming a moat region about the spacer and within the semiconductor layer;
    depositing or growing a gate dielectric material within the moat region; and
    forming one or more nanopores within the semiconductor layer.

2. The method of claim 1, wherein the step of providing the substrate comprises providing a semiconductor-on-insulator substrate.

3. The method of claim 1, wherein the substrate comprises a plurality of semiconductor-on-insulator layers.

4. The method of claim 1, wherein the one or more nanopores comprise an opening between about 1 nm and about 100 nm.

5. The method of claim 1, wherein the one or more nanopores are formed using a wet etchant, and wherein nanopore formation is controlled by one or more of: (1) electric current feedback monitoring, (2) capacitance measurement monitoring, (3) chemical-stop etching, wherein an etching-chemical mixes with another chemical upon the nanopore formation and loses etching activity, and (4) formation of a material-aggregate when etching-chemical mixes with another chemical upon nanopore formation, wherein the material-aggregate physically stops further nanopore formation.

6. The method of claim 1, wherein during formation of the one or more nanopores, etching is stopped before the formation of the one or more nanopores based on a measurement of one or more of: electrical current measurement, capacitive measurement, and conductance measurement.

7. The method of claim 1, further comprising a step of forming an etch region within the semiconductor layer.

8. The method of claim 1, wherein a plurality of independently-controlled transistors is formed using the semiconductor layer and about the one or more nanopores.

9. The method of claim 1, wherein the step of forming the one or more nanopores within the semiconductor layer comprises forming a plurality of nanopores.

10. The method of claim 1, wherein the structure is a self-aligned structure overlying and aligned with the substrate etch region.

11. The method of claim 10, wherein the spacer is used as a mask to form the moat region.

12. The method of claim 1, wherein the gate dielectric material comprises a gate oxide.

13. The method of claim 12, further comprising a step of forming a gate layer.

14. The method of claim 1, further comprising:
    forming a contact to the source region;
    forming a contact to the drain region; and
    forming a contact to a gate region comprising the gate dielectric material.

15. The method of claim 14, wherein at least two of the contact to the source region, the contact to the drain region, and the contact to the gate region are formed on a same side of the substrate.

16. The method of claim 15, wherein the contact to the source region, the contact to the drain region, and the contact to the gate region are formed on the same side of the substrate.

17. The method of claim 14, wherein the gate region is C-shaped or V-shaped.

18. The method of claim 1, wherein the channel is C-shaped or V-shaped.

19. The method of claim 1, further comprising a step of forming one or more additional layers over the channel.

20. The method of claim 19, wherein the one or more additional layers comprise organic molecules or biomolecules, semiconducting materials, metals, semi metals, insulators, dielectric materials, or meta-materials.

* * * * *